(12) United States Patent
Hlubek et al.

(10) Patent No.: US 9,404,099 B2
(45) Date of Patent: Aug. 2, 2016

(54) OPTIMIZED ENDONUCLEASES AND USES THEREOF

(75) Inventors: Andrea Hlubek, Quedlinburg (DE); Christian Biesgen, Quedlinburg (DE)

(73) Assignee: BASF Plant Science Company GmbH, Ludwigshafen (DE)

( * ) Notice: Subject to any disclaimer, the term of this patent is extended or adjusted under 35 U.S.C. 154(b) by 1105 days.

(21) Appl. No.: 13/512,219

(22) PCT Filed: Nov. 25, 2010

(86) PCT No.: PCT/IB2010/055428
§ 371 (c)(1),
(2), (4) Date: May 25, 2012

(87) PCT Pub. No.: WO2011/064736
PCT Pub. Date: Jun. 3, 2011

(65) Prior Publication Data
US 2012/0246764 A1 Sep. 27, 2012

Related U.S. Application Data

(60) Provisional application No. 61/264,715, filed on Nov. 27, 2009, provisional application No. 61/365,836, filed on Jul. 20, 2010.

(30) Foreign Application Priority Data

Nov. 27, 2009 (EP) ..................................... 09177375
Jul. 20, 2010 (EP) ..................................... 10170199

(51) Int. Cl.
*C12N 9/22* (2006.01)
*C12N 5/14* (2006.01)
*C12N 15/82* (2006.01)

(52) U.S. Cl.
CPC ... *C12N 9/22* (2013.01); *C12N 5/14* (2013.01); *C12N 15/82* (2013.01)

(58) Field of Classification Search
None
See application file for complete search history.

(56) References Cited

U.S. PATENT DOCUMENTS

| 5,962,327 | A | 10/1999 | Dujon et al. |
| 2010/0071083 | A1 | 3/2010 | Smith et al. |

FOREIGN PATENT DOCUMENTS

| WO | WO-96/14408 A2 | 5/1996 |
| WO | WO-96/20951 A1 | 7/1996 |
| WO | WO-99/45132 A1 | 9/1999 |
| WO | WO-00/02996 A2 | 1/2000 |
| WO | WO-00/27878 A1 | 5/2000 |
| WO | WO-01/38504 A2 | 5/2001 |
| WO | WO-01/89283 A1 | 11/2001 |
| WO | WO-02/099105 A2 | 12/2002 |
| WO | WO-03/060133 A2 | 7/2003 |
| WO | WO-03/062455 A2 | 7/2003 |
| WO | WO-03/089452 A2 | 10/2003 |
| WO | WO-2004/015134 A2 | 2/2004 |
| WO | WO-2005/105989 A1 | 11/2005 |
| WO | WO-2006/032426 A2 | 3/2006 |
| WO | WO-2007/034262 A1 | 3/2007 |
| WO | WO-2007/047859 A2 | 4/2007 |
| WO | WO-2007/093918 A2 | 8/2007 |
| WO | WO-2007/135022 A1 | 11/2007 |
| WO | WO-2008/076290 A2 | 6/2008 |
| WO | WO-2008/093249 A2 | 8/2008 |
| WO | WO-2008/102198 A1 | 8/2008 |
| WO | WO-2008/130629 A2 | 10/2008 |
| WO | WO-2008/152524 A2 | 12/2008 |
| WO | WO-2009/001159 A1 | 12/2008 |
| WO | WO-2009/009105 A2 | 1/2009 |
| WO | WO-2009/042163 A2 | 4/2009 |
| WO | WO-2009/059195 A2 | 5/2009 |
| WO | WO-2009/076292 A2 | 6/2009 |
| WO | WO-2009/114321 A2 | 9/2009 |
| WO | WO-2009/130695 A2 | 10/2009 |
| WO | WO-2009/131632 A1 | 10/2009 |
| WO | WO-2009/134714 A2 | 11/2009 |
| WO | WO-2010/001189 A1 | 1/2010 |
| WO | WO-2010/079430 A1 | 7/2010 |
| WO | WO-2011/064750 A1 | 6/2011 |
| WO | WO-2011/064751 A1 | 6/2011 |

OTHER PUBLICATIONS

Colleaux et al 1993 (Genbank Accession # AAA32167.1).*
"RecName: Full=Probable intron-encoded endonuclease 1", UniProt Database, Accession No. Q34807, Mar. 1, 2001.
International Preliminary Report on Patentability for PCT/IB2010/055428 dated May 30, 2012.
Mori, T., et al., "Sandwiched zinc-finger nucleases harboring a single-chain FokI dimer as a DNA-cleavage domain", Biochemical and Biophysical Research Communications, 2009, vol. 390, No. 3, pp. 694-697.
Paques, F., et al., "Meganucleases and DNA double-strand break-induced recombination: perspectives for gene therapy", Current Gene Therapy, 2007, vol. 7, No. 1, pp. 49-66.
Supplementary European Search Report for EP10832738 dated May 14, 2013.
Bachmair, A., et al., "In Vivo Half-Life of a Protein is a Function of its Amino-Terminal Residue", Science, 1986, vol. 234, pp. 179-186.
Rechsteiner, M., et al., "Pest Sequences and Regulation by Proteolysis", Trends in Biochem. Sci., 1996, vol. 21, No. 7, pp. 267-271.
"DNA Endonuclease (Mitochondrion) [Saccharomyces cerevisiae YJM789]", GenBank Database Accession No. ABS28696, Aug. 3, 2007.

(Continued)

*Primary Examiner* — Brent Page
*Assistant Examiner* — Matthew Keogh
(74) *Attorney, Agent, or Firm* — Drinker Biddle & Reath LLP

(57) ABSTRACT

Provided are optimized endonucleases, as well as methods of targeted integration, targeted deletion or targeted mutation of [polynucleotides using optimized endonucleases.

17 Claims, 2 Drawing Sheets

(56) References Cited

OTHER PUBLICATIONS

Boch, J., et al., "Breaking the Code of DNA Binding Specificity of TAL-Type III Effectors", Science, 2009, vol. 326, pp. 1509-1512.
Lippow, S. M., et al., "Creation of a Type IIS Restriction Endonuclease with a Long Recognition Sequence", Nucleic Acids Research, 2009, vol. 37, No. 9, pp. 3061-3073.
"Yeast (S. cerevisiae) MT 21S RRNA Gene Intron R1 Containing ORF", Accession No. Q36760, EMBL Database, Nov. 1, 1996.
"DNA endonuclease", Accession No. A7LCP1, EMBL Database, Sep. 11, 2007.
"Hypothetical 21S RRNA Intron Protein", Accession No. P03882, EMBL Database, Jul. 21, 1986.
International Search Report for PCT/IB2010/055428, mailed Apr. 21, 2011.

* cited by examiner

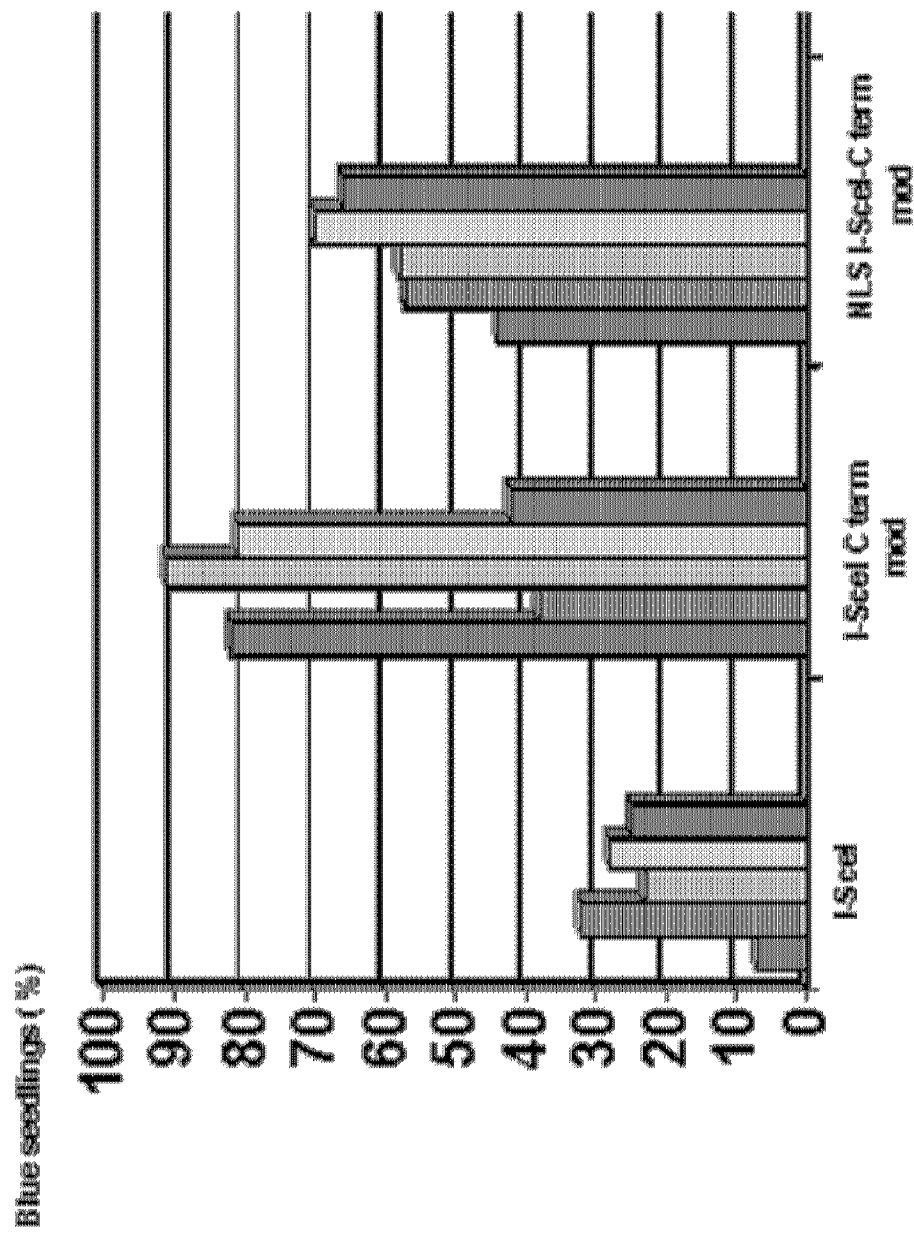
Figure 1: Frequency of homologous Recombination Events

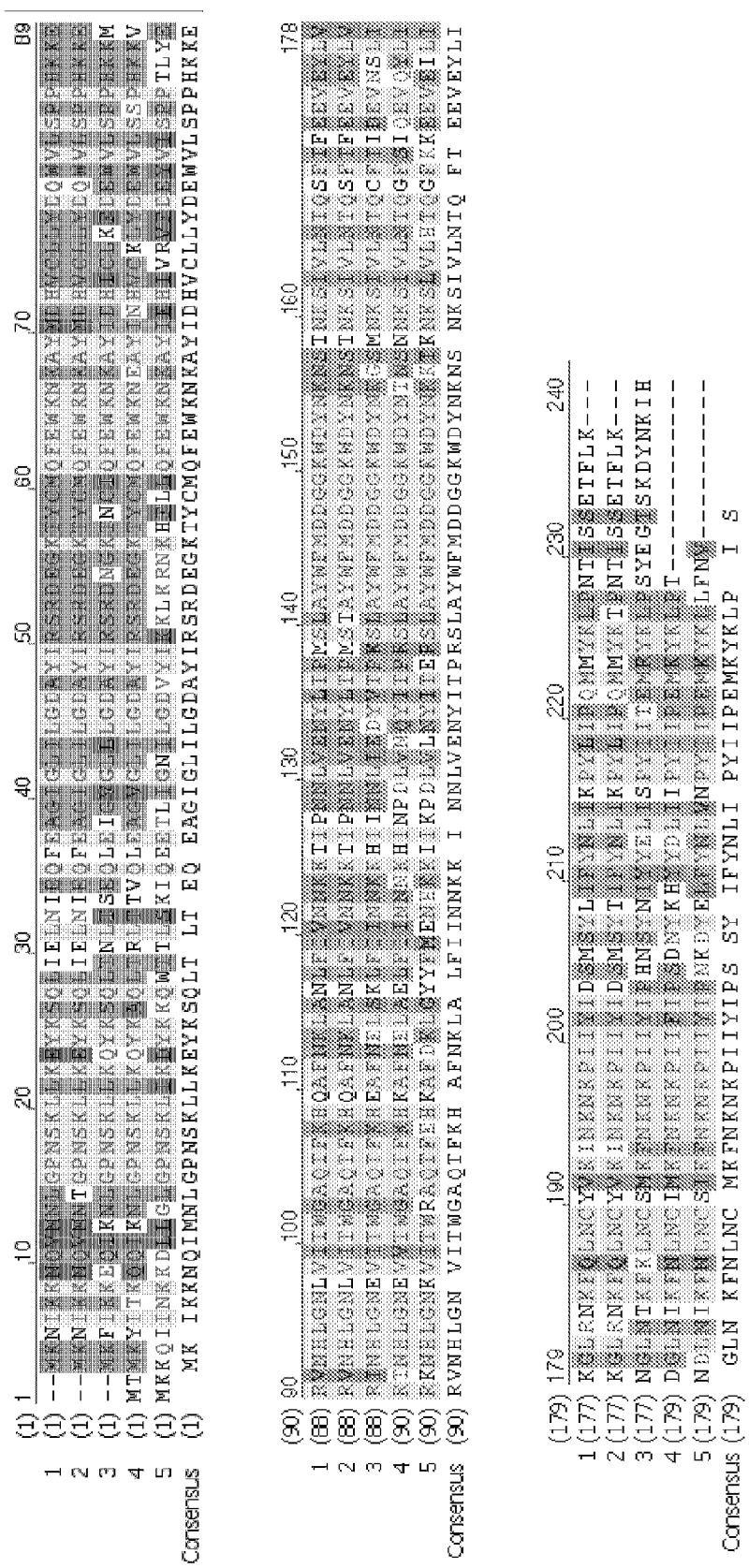
Figure 2: Sequence alignment of different I-SceI homologs

OPTIMIZED ENDONUCLEASES AND USES THEREOF

RELATED APPLICATIONS

This application is a national stage application (under 35 U.S.C. §371) of PCT/AB2010/055428, filed Nov. 25, 2010 which claims benefit of U.S. Provisional Application No. 61/264,715, filed Nov. 27, 2009, European Application No. 09177375.4, filed Nov. 27, 2009; U.S. Provisional Application No. 61/365,836, filed Jul. 20, 2010, and European Application No. 10170199.3, filed Jul. 20, 2010.

SUBMISSION OF SEQUENCE LISTING

The Sequence Listing associated with this application is filed in electronic format via EFS-Web and hereby incorporated by reference into the specification in its entirety. The name of the text file containing the Sequence Listing is Revised Sequence Listing 13987 00192 US. The size of the text file is 108 KB and the text file was created on Apr. 10, 2013.

FIELD OF THE INVENTION

The invention relates to optimized endonucleases, as well as methods of targeted integration, targeted deletion or targeted mutation of polynucleotides using optimized endonucleases.

BACKGROUND OF THE INVENTION

Genome engineering is a common term to summarize different techniques to insert, delete, substitute or otherwise manipulate specific genetic sequences within a genome and has numerous therapeutic and biotechnological applications. More or less all genome engineering techniques use recombinases, integrases or endonucleases to create DNA double strand breaks at predetermined sites in order to promote homologous recombination.

In spite of the fact that numerous methods have been employed to create DNA double strand breaks, the development of effective means to create DNA double strand breaks at higly specific sites in a genome remains a major goal in gene therapy, agrotechnology, and synthetic biology.

One approach to achieve this goal is to use nucleases with specificity for a sequence that is sufficiently large to be present at only a single site within a genome. Nucleases recognizing such large DNA sequences of about 15 to 30 nucleotides are therefore called "meganucleases" or "homing endonucleases" and are frequently associated with parasitic or selfish DNA elements, such as group 1 self-splicing introns and inteins commonly found in the genomes of plants and fungi. Meganucleases are commonly grouped into four families: the LAGLIDADG family, the GIY-YIG family, the His-Cys box family and the HNH family. These families are characterized by structural motifs, which affect catalytic activity and the sequence of their DNA recognition sequences.

Natural meganucleases from the LAGLIDADG family have been used to effectively promote site-specific genome modifications in insect and mammalian cell cultures, as well as in many organisms, such as plants, yeast or mice, but this approach has been limited to the modification of either homologous genes that conserve the DNA recognition sequence or to preengineered genomes into which a recognition sequence has been introduced. In order to avoid these limitations and to promote the systematic implementation of DNA double strand break stimulated gene modification new types of nucleases have been created.

One type of new nucleases consists of artificial combinations of unspecific nucleases to a higly specific DNA binding domain. The effectiveness of this strategy has been demonstrated in a variety of organisms using chimeric fusions between an engineered zinc finger DNA-binding domain and the non-specific nuclease domain of the FokI restriction enzyme (e.g. WO03/089452) a variation of this approach is to use an inactive variant of a meganuclease as DNA binding domain fused to an unspecific nuclease like FokI as disclosed in Lippow et al., "Creation of a type IIS restriction endonuclease with a long recognition sequence", Nucleic Acid Research (2009), Vol. 37, No. 9, pages 3061 to 3073.

An alternative approach is to genetically engineer natural meganucleases in order to customize their DNA binding regions to bind existing sites in a genome, thereby creating engineered meganucleases having new specificities (e.g WO07093918, WO2008/093249, WO09114321). However, many meganucleases which have been engineered with respect to DNA cleavage specificity have decreased cleavage activity relative to the naturally occurring meganucleases from which they are derived (US2010/0071083). Most meganucleases do also act on sequences similar to their optimal binding site, which may lead to unintended or even detrimental off-target effects. Several approaches have already been taken to enhance the efficiency of meganuclease induced homologous recombination e.g. by fusing nucleases to the ligand binding domain of the rat Glucocorticoid Receptor in order to promote or even induce the transport of this modified nuclease to the cell nucleus and therefore its target sites by the addition of dexamethasone or similar compounds (WO2007/135022). Despite that fact, there is still a need in the art to develop meganucleases having high induction rates of homologous recombination and/or a high specificity for their binding site, thereby limiting the risk of off-target effects.

BRIEF SUMMARY OF THE INVENTION

The invention provides optimized versions of endonucleases of the LAGLIDADG endonuclease family. In particular optimized endonucleases comprising an amino acid sequence having at least 80% amino acid sequence identity to a polypeptide described by SEQ ID NO: 1, 15, 16, 17 or 19. In one embodiment of the invention, the optimized endonucleases are wildtype or engineered versions of I-SceI, as described by SEQ ID NO: 1 or one of its homologs having at least 55%, 58%, 60%, 70%, 80%, 85%, 90%, 92%, 93%, 94%, 95%, 96%, 97%, 98% or 99% sequence identity on amino acid level, having one or more mutations selected from the groups of:

a) I-SceI-1, I-SceI-2, I-SceI-3, I-SceI-4, I-SceI-5, I-SceI-6, I-SceI-7, I-SceI-8 and I-SceI-9;

b) S229K, S229A, S229P, S229G, S229E, S229Q, S229D, S229N, S229C, S229Y, S229T, M203K, M203H, M203R, Q77K, Q77H, Q77R, E130K, E130H, E130R, Y199K, Y199H and Y199R;

c) a methionine, valine, glycine, threonin, serine, alanine, cysteine, glutamic acid, glutamine, aspartic acid, asparagine, isoleucine or histidine after the start methionine of their amino acid sequence; or d) a combination of one or more mutations selected from a) and b), a) and c), b) and c) or a) b) and c) above.

In one embodiment of the invention, the optimized endonuclease comprises an amino acid sequence described by SEQ ID NO 2, 3 or 5.

In a further embodiment of the invention, the optimized endonucleases is an engineered version of an endonuclease comprising an amino acid sequence having at least 80% amino acid sequence identity to a polypeptide described by SEQ ID NO: 1, 15, 16, 17 or 19.

In another embodiment, the invention provides an endonuclease having at least 80% amino acid sequence identity to a polypeptide described by SEQ ID NO: 1, or an engineered version of an endonuclease having at least 80% amino acid sequence identity to a polypeptide described by SEQ ID NO: 1, wherein the amino acid sequence TISSETFLK is removed by deletion or mutation of any one of the amino acids of the amino acid sequence TISSETFLK. Another preferred embodiment of the invention is an optimized endonuclease as claimed in any of claims 1 to 4 comprising an amino acid sequence having at least 80% amino acid sequence identity to a polypeptide described by SEQ ID NO: 1 or 2 and comprising a mutation of serine Nr 229 of SEQ ID NO: 1. In a further embodiment of the invention, the optimized endonuclease is fused to at least one zinc finger domain, or a at least one repeat units derived from a transcription activator-like (TAL) effector, or at least one zinc finger domain and at least one repeat units derived from a transcription activator-like (TAL) effector. Preferably the optimized endonucleases comprise an SceIII or SecIV secretion signal. The invention does also provide isolated polynucleotides comprising a polynucleotide sequence, which codes for an optimized endonuclease.

Preferably this polynucleotide is codon opitimized or has a low content RNA instability motives or has a low content of codon repeats, or has a low content of cryptic splice sites, or has a low content of alternative start codons, has a low content of restriction sites, or has a low content of RNA secondary structures or has any combination of the features described above. Another embodiment of the invention is an expression cassette comprising an isolated polynucleotide as described above in functional combination with a promoter and a terminator sequence. Other embodiments of the invention are vectors, host cells or non human organisms comprising a polynucleotide coding for an optimized endonuclease, or an isolated polynucleotide coding for an optimized endonuclease, or an expression cassette comprising a polynucleotide coding for an optimized endonuclease, and vectors, host cells or non human organisms comprising a combination of the endonucleoases, polynucleotides and expression cassettes described above. Preferably the non human organism is a plant.

The invention provides methods of using the endonucleases described herein to induce homologous recombination or end joining events. Preferably in methods for targeted integration of excision of sequences. Preferably the sequences being excised are marker genes. The invention does further provide a method for homologous recombination of polynucleotides comprising the following steps: a) providing a cell competent for homologous recombination, b) providing a polynucleotide comprising a DNA recognition site of an optimized endonuclease flanked by a sequence A and a sequence B, c) providing a polynucleotide comprising sequences A' and B', which are sufficiently long and homologous to sequence A and sequence B, to allow for homologous recombination in said cell and d) providing an optimized endonuclease as described herein or an expression cassette as described herein, e) combining b), c) and d) in said cell and f) detecting recombined polynucleotides of b) and c), or selecting for or growing cells comprising recombined polynucleotides of b) and c). Preferably the method for homologous recombination of polynucleotides leads to a homologous recombination, wherein a polynucleotide sequence comprised in the competent cell of step a) is deleted from the genome of the growing cells of step f). A further method of the invention is a method for targeted mutation comprising the following steps: a) providing a cell comprising a polynucleotide comprising a DNA recognition site of an optimized endonuclease, b) providing an optimized endonuclease as claimed in any one of claims 1 to 7 or an expression cassette as claimed in claim 10 and being able to cleave the DNA recognition site of step a), c) combining a) and b) in said cell and d) detecting mutated polynucleotides, or selecting for or growing cells comprising mutated polynucleotides.

In another preferred embodiment of the invention, the methods described above comprise a step, wherein the optimized endonuclease and the DNA recogntition site are combined in at least one cell via crossing of organisms, via transformation or via transport mediated via a Sec III or SecIV peptide fused to the optimized endonuclease.

BRIEF DESCRIPTION OF THE FIGURES

FIG. 1 shows a comparison of the frequency of homologous recombination, measured by restoration of beta glucuronidase activity (% blue seedlings), after induced recombination by three different I-SceI variants. Each I-SceI variant was tested in five different plant lines, carrying the test construct. For each combination 96 seedlings of the T2 generation were analyzed for beta glucuronidase activity ("I-SceI", having the amino acid sequence described by SEQ ID NO: 1; "I-SceI c-term mod" having the amino acid sequence described by SEQ ID NO: 3; "NLS I-SceI c-term mod", having the amino acid sequence described by SEQ ID NO: 5), see also Example 10b.

FIG. 2 depicts a sequence alignment of different I-SceI homologs, wherein 1 is SEQ ID NO: 1, 2 is SEQ ID NO: 15, 3 is SEQ ID NO: 16, 4 is SEQ ID NO: 17, 5 is SEQ ID NO: 18 and Consensus is SEQ ID NO: 43).

DESCRIPTION OF THE INVENTION

The invention provides optimized endonucleases, which can be used as alternative DNA double strand break inducing enzymes. The invention does also provide methods of using these optimized endonucleases.

Optimized endonucleases are variants of I-Sce-I (described by SEQ ID NO: 1) and homologs of I-Sce I having at least 55%, 58%, 60%, 70%, 80%, 85%, 90%, 92%, 93%, 94%, 95%, 96%, 97%, 98% or 99% sequence identity on amino acid level. Optimized versions of I-SceI are also called optimized I-SceI.

Homologs of I SceI endonucleases can be cloned from other organisms or can be created by mutating LAGLIDADG endonucleases, e.g. by replacing, adding or deleting amino acids of the amino acid sequence of a given LAGLIDADG endonuclease.

For example, it is possible to add nuclear localization signals to the amino acid sequence of a LAGLIDADG endonuclease and/or change one or more amino acids and/or to delete parts of its sequence, e.g. parts of the N-terminus or parts of its C-terminus.

TABLE 1

Exemplary homologs of I-SceI, which can be cloned from other organisms are described in Table 1;

| Uni-Prot Accession Nr. | Organism | SEQ ID NO: | Amino Acid Sequence Identity to I-SceI |
|---|---|---|---|
| A7LCP1 | S. cerevisiae | 1 | 100 |
| Q36760 | S. cerevisiae | 15 | 98 |
| O63264 | Z. bisporus | 16 | 72 |
| Q34839 | K. thermotolerans | 17 | 71 |
| Q34807 | P. canadensis | 18 | 58 |

LAGLIDADG endonucleases usefull in the invention can be found in the genomes of algae, fungi, yeasts, protozoan, chloroplasts, mitochondria, bacteria and archaea. LAGLIDADG endonucleases comprise at least one conserved LAGLIDADG motif (SEQ ID NO: 32). The name of the LAGLIDADG motif (SEQ ID NO: 32) is based on a characteristic amino acid sequence appearing in all LAGLIDADG endonucleases. The term LAGLIDADG is an acronym of this amino acid sequence according to the one-letter-code as described in the STANDARD ST.25 i.e. the standard adopted by the PCIPI Executive Coordination Committee for the presentation of nucleotide and amino acid sequence listings in patent applications.

However, the LAGLIDADG motif SEQ ID NO: 32 is not fully conserved in all LAGLIDADG endonucleases, (see for example Chevalier et al. (2001), Nucleic Acids Res. 29(18): 3757 to 3774, or Dalgaard et al. (1997), Nucleic Acids Res. 25(22): 4626 to 4638), so that some LAGLIDADG endonucleases comprise some one or several amino acid changes in their LAGLIDADG motif (SEQ ID NO: 32). LAGLIDADG endonucleases comprising only one LAGLIDADG motif (SEQ ID NO: 32) act usually as homo- or heterodimers. LAGLIDADG endonucleases comprising two LAGLIDADG motifs (SEQ ID NO: 32) act as monomers and comprise usually a pseudo-dimeric structure.

LAGLIDADG endonucleases can be isolated from polynucleotides of organisms mentioned as examples in Table 1, or de novo synthesized by techniques known in the art, e.g. using sequence information available in public databases known to the person skilled in the art, for example Genbank (Benson (2010)), Nucleic Acids Res 38:D46-51 or Swissprot (Boeckmann (2003), Nucleic Acids Res 31:365-70)

A collection of LAGLIDADG endonucleases can be found in the PFAM-Database for protein families. The PFAM-Database accession number PF00961 describes the LAGLIDADG 1 protein family, which comprises about 800 protein sequences. PFAM-Database accession number PF03161 describes members of the LAGLIDADG 2 protein family, comprising about 150 protein sequences. An alternative collection of LAGLIDADG endonucleases can be found in the InterPro data base, e.g. InterPro accession number IPR004860.

Another way to create homologs of LAGLIDADG endonucleases is to mutate the amino acid sequence of an LAGLIDADG endonuclease in order to modify its DNA binding affinity, its dimer formation affinity or to change its DNA recognition sequence. The determination of protein structure as well as sequence alignments of homologs of LAGLIDADG endonucleases allows for rational choices concerning the amino acids that can be changed to affect its DNA binding affinity, its enzymatic activity, or to change its DNA recognition sequence.

As used herein, the term "DNA-binding affinity" means the tendency of a meganuclease or LAGLIDADG endonuclease to non-covalently associate with a reference DNA molecule (e.g., a DNA recognition sequence or an arbitrary sequence). Binding affinity is measured by a dissociation constant, KD (e.g., the KD of I-SceI for the WT DNA recognition sequence is approximately 0.1 nM). As used herein, a meganuclease has "altered" binding affinity if the $K_D$ of the recombinant meganuclease for a reference DNA recognition sequence is increased or decreased by a statistically significant ($p<0.05$) amount relative to a reference meganuclease or or LAGLIDADG endonuclease.

As used herein, the term "enzymatic activity" refers to the rate at which a meganuclease e.g. a LAGLIDADG endonuclease cleaves a particular DNA recognition sequence. Such activity is a measurable enzymatic reaction, involving the hydrolysis of phospho-diester-bonds of double-stranded DNA. The activity of a meganuclease acting on a particular DNA substrate is affected by the affinity or avidity of the meganuclease for that particular DNA substrate which is, in turn, affected by both sequence-specific and non-sequence-specific interactions with the DNA.

Nucleases may further be optimized by deleting 50, 40, 30, 20, 10, 9, 8, 7, 6, 5, 4, 3, 2, or 1 amino acids of its amino acid sequence, without destroying its endonuclease activity. For example, in case parts of the amino acid sequence of a LAGLIDADG endonuclease is deleted, it is important to retain the LAGLIDADG endonuclease motif described above.

It is preferred to delete PEST sequences or other destabilizing motifs like KEN-box, D-box and A-box. Those motifs can also be destroyed by indroduction of single amino acid exchanges, e.g introduction of a positively charged aminoacid (arginine, histidine and lysine) into the PEST sequence.

LAGLIDADG endonucleases, which have been mutated in order to modify their DNA binding affinity, or to change its DNA recognition sites are called engineered endonucleases. I-SceI as well as homologs of I-Sce I having at least 55%, 58%, 60%, 70%, 80%, 85%, 90%, 92%, 93%, 94%, 95%, 96%, 97%, 98% or 99% sequence identity on amino acid level can be engineered like other LAGLIDADG endonucleases in order to change its DNA binding affinity, its enzymatic activity, or to change its DNA recognition sequence. Engineered versions of I-SceI and homologs of I-Sce I having at least 55%, 58%, 60%, 70%, 80%, 85%, 90%, 92%, 93%, 94%, 95%, 96%, 97%, 98% or 99% sequence identity on amino acid level.

Accordingly in one embodiment of the invention, the optimized endonucleases are engineered version of I-SceI or its homologs having at least 55%, 58%, 60%, 70%, 80%, 85%, 90%, 92%, 93%, 94%, 95%, 96%, 97%, 98% or 99% sequence identity on amino acid level and having a changed DNA binding affinity, a changed enzymatic activity, or a changed DNA recognition sequence, when compared to its non engineered form, meaning the respective LAGLIDADG endonuclease at it occurs in nature.

In another embodiment of the invention, the optimized endonucleases are variants of I-SceI as described by SEQ ID NO: 1 or its homologs having at least 55%, 58%, 60%, 70%, 80%, 85%, 90%, 92%, 93%, 94%, 95%, 96%, 97%, 98% or 99% sequence identity on amino acid level like they occure in nature.

Homologs, which do not occure in nature, but have at least one of the mutations A36G, L40M, L40V, I41S, I41N, L43A, H91A and I123L, which have little effect on the DNA binding affinity of I-SceI, or will change its DNA recognition sequence will also be considered to be homologs occurring in nature, as long as they do not comprise other mutations, which change their DNA binding affinity, their enzymatic activity, or their DNA recognition sequence, when compared to I-SceI as described by SEQ ID NO: 1 or the respective homolog having at least 55%, 58%, 60%, 70%, 80%, 85%, 90%, 92%, 93%, 94%, 95%, 96%, 97%, 98% or 99% sequence identity on amino acid level like it occures in nature.

Engineered versions of I-SceI, having an increased or decreased DNA-binding affinity are for example disclosed in WO07/047859 and WO09/076292 herein included by reference.

If not explicitly mentioned otherwise, all mutants will be named according to the amino acid numbers of the wildtype amino acid sequences of the respective endonuclease, e.g. the mutant L19 of I-SceI will have an amino acid exchange of leucine at position 19 of the wildtype I-SceI amino acid sequence, as described by SEQ ID NO: 1. The L19H mutant of I-SceI, will have a replacement of the amino acid leucine at position 19 of the wildtype I-SceI amino acid sequence with hystidine.

For example, the DNA-binding affinity of I-SceI can be increased by at least one modification corresponding to a substitution selected from the group consisting of:
(a) substitution of D201, L19, L80, L92, Y151, Y188, I191, Y199 or Y222 with H, N, Q, S, T, K or R; or
(b) substitution of N15, N17, S81, H84, N94, N120, T156, N157, S159, N163, Q165, S166, N194 or S202 with K or R.

DNA-binding affinity of I-SceI can be decreased by at least one mutation corresponding to a substitution selected from the group consisting of:
(a) substitution of K20, K23, K63, K122, K148, K153, K190, K193, K195 or K223 with H, N, Q, S, T, D or E; or
(b) substitution of L19, L80, L92, Y151, Y188, I191, Y199, Y222, N15, N17, S81, H84, N94, N120, T156, N157, S159, N163, Q165, S166, N194 or S202 with D or E.

Engineered versions of I-SceI, I-CreI, I-MsoI and I-CeuI having a changed DNA recognition sequence are disclosed for example in WO007/047859 and WO09/076292.

For example, an important DNA recognition site of I-SceI has the following sequence:

```
sense:          5'-T T A C C C T G T T A T C C C T A G-3'
                (SEQ ID NO: 44)
base position:     1 2 3 4 5 6 7 8 9 10 11 12 13 14 15 16 17 18
antisense       3'-A A T G G G A C A A T A G G G A T C-5'
                (SEQ ID NO: 45)
```

The following mutations of I-SceI will change the preference for C at position 4 to A: K50

The following mutations of I-SceI will keep the preference for C at position 4: K50, CE57

The following mutations of I-SceI will change the preference for C at position 4 to G: E50, R57, K57.

The following mutations of I-SceI will change the preference for C at position 4 to T: K57, M57, Q50.

The following mutations of I-SceI will change the preference for C at position 5 to A: K48, Q102.

The following mutations of I-SceI will keep the preference for C at position 5: R48, K48, E102, E59

The following mutations of I-SceI will change the preference for C at position 5 to G: E48, K102, R102.

The following mutations of I-SceI will change the preference for C at position 5 to T: Q48, C102, L102, V102.

The following mutations of I-SceI will change the preference for C at position 6 to A: K59.

The following mutations of I-SceI will keep the preference for C at position 6: R59, K59.

The following mutations of I-SceI will change the preference for C at position 6 to G: K84, E59.

The following mutations of I-SceI will change the preference for C at position 6 to T: Q59, Y46.

The following mutations of I-SceI will change the preference for T at position 7 to A: C46, L46, V46.

The following mutations of I-SceI will change the preference for T at position 7 to C: R46, K46, E86.

The following mutations of I-SceI will change the preference for T at position 7 to G: K86, R86, E46.

The following mutations of I-SceI will keep the preference for T at position 7: K68, C86, L86, Q46*.

The following mutations of I-SceI will change the preference for G at position 8 to A: K61, S61, V61, A61, L61.

The following mutations of I-SceI will change the preference for G at position 8: E88, R61, H61.

The following mutations of I-SceI will keep the preference for G at position 8: E61, R88, K88.

The following mutations of I-SceI will change the preference for G at position 8 to T: K88, Q61, H61.

The following mutations of I-SceI will change the preference for T at position 9 to A: T98, C98, V98, L9B.

The following mutations of I-SceI will change the preference for T at position 9 to C: R98, K98.

The following mutations of I-SceI will change the preference for T at position 9 to G: E98, D98.

The following mutations of I-SceI will keep the preference for T at position 9: Q98.

The following mutations of I-SceI will change the preference for T at position 10 to A: V96, C96, A96.

The following mutations of I-SceI will change the preference for T at position 10 to C: K96, R96.

The following mutations of I-SceI will change the preference for T at position 10 to G: D96, E96.

The following mutations of I-SceI will keep the preference for T at position 10: Q96.

The following mutations of I-SceI will keep the preference for A at position 11: C90, L90.

The following mutations of I-SceI will change the preference for A at position 11 to C: K90, R90.

The following mutations of I-SceI will change the preference for A at position 11 to G: E90.

The following mutations of I-SceI will change the preference for A at position 11 to T: Q90.

The following mutations of I-SceI will change the preference for T at position 12 to A: 0193.

The following mutations of I-SceI will change the preference for T at position 12 to C: E165, E193, D193.

The following mutations of I-SceI will change the preference for T at position 12 to G: K165, R165.

The following mutations of I-SceI will keep the preference for T at position 12: C165, L165, C193, V193, A193, T193, S193.

The following mutations of I-SceI will change the preference for C at position 13 to A: C193, L193.

The following mutations of I-SceI will keep the preference for C at position 13: K193, R193, D192.

The following mutations of I-SceI will change the preference for C at position 13 to G: E193, D193, K163, R192.

The following mutations of I-SceI will change the preference for C at position 13 to T: Q193, C163, L163.

The following mutations of I-SceI will change the preference for C at position 14 to A: L192, C192.

The following mutations of I-SceI will keep the preference for C at position 14: E161, R192, K192.

The following mutations of I-SceI will change the preference for C at position 14 to G: K147, K161, R161, R197, D192, E192.

The following mutations of I-SceI will change the preference for C at position 14 to T: K161, Q192.

The following mutations of I-SceI will keep the preference for C at position 15: E151.

The following mutations of I-SceI will change the preference for C at position 15 to G: K151.

The following mutations of I-SceI will change the preference for C at position 15 to T: C151, L151, K151.

The following mutations of I-SceI will keep the preference for A at position 17: N152, S152, C150, L150, V150, T150.

The following mutations of I-SceI will change the preference for A at position 17 to C: K152, K150.

The following mutations of I-SceI will change the preference for A at position 17 to G: N152, S152, D152, D150, E150.

The following mutations of I-SceI will change the preference for A at position 17 to T: Q152, Q150.

The following mutations of I-SceI will change the preference for G at position 18 to A: K155, C155.

The following mutations of I-SceI will change the preference for G at position 18: R155, K155.

The following mutations of I-SceI will keep the preference for G at position 18: E155.

The following mutations of I-SceI will change the preference for G at position 18 to T: H155, Y155.

Combinations of several mutations may enhance the effect. One example is the triple mutant W149G, D150C and N152K, which will change the preference of I-SceI for A at position 17 to G.

In order to preserve the enzymatic activity the mutations 138S, 138N, G39D, G39R, L40Q, L42R, D44E, D44G, D44H, D44S, A45E, A45D, Y46D, 147R, 147N, D144E, D145E, D145N and G146E of I-SceI or its homolog having at least 55%, 58%, 60%, 70%, 80%, 85%, 90%, 92%, 93%, 94%, 95%, 96%, 97%, 98% or 99% sequence identity on amino acid level, should be avoided.

Mutations which alter the enzymatic activity, the DNA-binding-affinity, the DNA recognition sequence of I-SceI or its homolog having at least 55%, 58%, 60%, 70%, 80%, 85%, 90%, 92%, 93%, 94%, 95%, 96%, 97%, 98% or 99% sequence identity on amino acid level may be combined to create an engineered endonuclease, e.g. an engineered endonuclease based on I-SceI and having an altered DNA-binding-affinity and/or a changed DNA recognition sequence, when compared to I-SceI as described by SEQ ID NO: 1.

Besides rational engineering of I-SceI, it is also possible to alter the enzymatic activity, the DNA-binding-affinity, the DNA recognition sequence of I-SceI or its homolog having at least 55%, 58%, 60%, 70%, 80%, 85%, 90%, 92%, 93%, 94%, 95%, 96%, 97%, 98% or 99% sequence identity on amino acid level, by employing molecular evolution. Polynucleotides encoding a candidate endonuclease enzyme can, for example, be modulated with DNA shuffling protocols. DNA shuffling is a process of recursive recombination and mutation, performed by random fragmentation of a pool of related genes, followed by reassembly of the fragments by a polymerase chain reaction-like process. See, e.g., Stemmer (1994) Proc Natl Acad Sci USA 91:10747-10751; Stemmer (1994) Nature 370:389-391; and U.S. Pat. Nos. 5,605,793, 5,837,458, 5,830,721 and 5,811,238. Engineered endonucleases can also be created by using rational design, based on further knowledge of the crystal structure of a given endonuclease see for example Fajardo-Sanchez et al., Computer design of obligate heterodimer meganucleases allows efficient cutting of custom DNA sequences, Nucleic Acids Research, 2008, Vol. 36, No. 7 2163-2173.

Numerous examples of engineered endonucleases, as well as their respective DNA recognition sites are known in the art and are disclosed for example in: WO 2005/105989, WO 2007/034262, WO 2007/047859, WO 2007/093918, WO 2008/093249, WO 2008/102198, WO 2008/152524, WO 2009/001159, WO 2009/059195, WO 2009/076292, WO 2009/114321, or WO 2009/134714, WO 10/001189 herein included by reference.

Mutations and changes in order to create optimized nucleases may be combined with the mutations used to create engineered endonucleases, for example, a homologue of I-SceI may be an optimized nuclease as described herein, but may also comprise mutations used to alter its DNA-binding-affinity and/or change its DNA recognition sequence.

The amino acid sequence of I-SceI or its homologs having at least 55%, 58%, 60%, 70%, 80%, 85%, 90%, 92%, 93%, 94%, 95%, 96%, 97%, 98% or 99% sequence identity on amino acid level, as well as the polynucletides coding for I-SceI or its homologs having at least 55%, 58%, 60%, 70%, 80%, 85%, 90%, 92%, 93%, 94%, 95%, 96%, 97%, 98% or 99% sequence identity on amino acid level, can be improved by adapting the polynucleotide sequence to the codon usage of the organism, in which I-SceI or its homologs having at least 55%, 58%, 60%, 70%, 80%, 85%, 90%, 92%, 93%, 94%, 95%, 96%, 97%, 98% or 99% sequence identity on amino acid level is intended to be expressed, or by deleting alternative start codons, or by deleting cryptic polyadenylation signals from the polynucleotide sequence coding for the endonuclease Mutations Used to Create Optimized Nucleases:

Optimized nucleases like optimized versions of I-SceI or its homologs having at least 55%, 58%, 60%, 70%, 80%, 85%, 90%, 92%, 93%, 94%, 95%, 96%, 97%, 98% or 99% sequence identity on amino acid level can be optimized by changing the amino acid sequence of the respective LAGLIDADG endonuclease to enhance protein stability. Accordingly optimized nucleases do not comprise or have a reduced number compared to the amino acid sequence of the non optimized nuclease of:

a) PEST-Sequences,
b) KEN-boxes
c) A-boxes,
d) D-boxes, or
e) do comprise an optimized N-terminal end for stability according to the N-end rule,
f) comprise a glycin as the second N-terminal amino acid, or
g) any combination of a), b), c) d), e) and f).

PEST Sequences are sequences of about 12 amino acids, comprising at least one prolin, one glutamate or aspartate and at least one serin or threonine. PEST Sequences are for example described in Rechsteiner M, Rogers SW. "PEST sequences and regulation by proteolysis."Trends Biochem, Sci. 1996; 21(7), pages 267 to 271.

The amino acid consensus sequence of a KEN-box is: KENXXX(N/D)

The amino acid consensus sequence of a A-box is: AQRXLXXSXXXQRVL (SEQ ID NO: 33)

The amino acid consensus sequence of a D-box is: RXXL

A further way to stabilize nucleases against degradation is to optimize the amino acid sequence of the N-terminus of the respective endonuclease according to the N-end rule. Nucleases which are optimized for the expression in eucaryotes comprise either methionine, valine, glycine, threonine, serine, alanine or cysteine after the start methionine of their amino acid sequence. Nucleases which are optimized for the expression in procaryotes comprise either methionine, valine, glycine, threonine, serine, alanine, cysteine, glutamic acid, glutamine, aspartic acid, asparagine, isoleucine or histidine after the start methionine of their amino acid sequence.

Nucleases may further be optimized by deleting 50, 40, 30, 20, 10, 9, 8, 7, 6, 5, 4, 3, 2, or 1 amino acids of its amino acid sequence, without destroying its endonuclease activity. For example, in case parts of the amino acid sequence of a LAGLIDADG endonuclease is deleted, it is important to retain the LAGLIDADG endonuclease motif (SEQ ID NO: 32) described above.

Another way to optimize nucleases is to add nuclear localization signals to the amino acid sequence of the nuclease. For example a nuclear localization signal as described by SEQ ID NO: 4.

Optimized nucleases may comprise a combination of the methods and features described above, e.g. they may comprise a nuclear localization signal, comprise a glycin as the second N-terminal amino acid or a deletion at the C-terminus or a combination of these features. Examples of optimized nucleases having a combination of the methods and features described above are for example described by SEQ ID NOs: 2, 3 and 5.

Optimized nucleases do not comprise an amino acid sequence described by the sequence:
HVCLLYDQWVLSPPH (SEQ ID NO: 25), LAYWFMDDGGK (SEQ ID NO: 26), KTIPNNLVENYLTPMSLAYWFMDDGGK (SEQ ID NO: 27), KPIIYIDSMSYLIFYNLIK (SEQ ID NO: 28), KLPNTISSETFLK (SEQ ID NO: 29), or TISSETFLK (SEQ ID NO: 31), or which does not comprise an amino acid sequence described by the sequence: HVCLLYDQWVLSPPH (SEQ ID NO: 25), LAYWFMDDGGK (SEQ ID NO: 26), KPIIYIDSMSYLIFYNLIK (SEQ ID NO: 28), KLPNTISSETFLK (SEQ ID NO: 29) or TISSETFLK (SEQ ID NO: 31), or which does not comprise an amino acid sequence described by the sequence: HVCLLYDQWVLSPPH (SEQ ID NO: 25), LAYWFMDDGGK (SEQ ID NO: 26), KLPNTISSETFLK (SEQ ID NO: 28) or TISSETFLK (SEQ ID NO: 31), or which does not comprise an amino acid sequence described by the sequence: LAYWFMDDGGK (SEQ ID NO: 26), KLPNTISSETFLK (SEQ ID NO: 28) or TISSETFLK (SEQ ID NO: 31), or which does not comprise an amino acid sequence described by the sequence: KLPNTISSETFLK (SEQ ID NO: 28) or TISSETFLK (SEQ ID NO: 31).

In one embodiment the optimized nuclease is I-SceI, or its homologs having at least 55%, 58%, 60%, 70%, 80%, 85%, 90%, 92%, 93%, 94%, 95%, 96%, 97%, 98% or 99% sequence identity on amino acid level in which the amino acid sequence TISSETFLK at the C-terminus of wildtype I-SceI or its homologs having at least 55%, 58%, 60%, 70%, 80%, 85%, 90%, 92%, 93%, 94%, 95%, 96%, 97%, 98% or 99% sequence identity on amino acid level and having an amino acid sequence TISSETFLK (SEQ ID NO: 31) at the C-terminus is deleted or mutated.

The amino acid sequence TISSETFLK (SEQ ID NO: 31) may be deleted or mutated, by deleting or mutating at least 1, 2, 3, 4, 5, 6. 7, 8 or 9 amino acids of the C-terminus of wildtype I-SceI or its homologs having at least 55%, 58%, 60%, 70%, 80%, 85%, 90%, 92%, 93%, 94%, 95%, 96%, 97%, 98% or 99% sequence identity on amino acid level and having an amino acid sequence TISSETFLK (SEQ ID NO: 31) at the C-terminus.

TABLE 2

Different examples for deletions of the TISSETFLK (SEQ ID NO: 31) amino acid sequence in wildtype I-SceI

| Wildtype and optimized I-SceI | amino acid sequence on C-terminus |
|---|---|
| I-SceI wildtype | TISSETFLK (SEQ ID NO: 31) |
| I-SceI -1 | TISSETFL (SEQ ID NO: 34) |
| I-SceI -2 | TISSETF (SEQ ID NO: 35) |
| I-SceI -3 | TISSET (SEQ ID NO: 36) |
| I-SceI -4 | TISSE (SEQ ID NO: 37) |
| I-SceI -5 | TISS (SEQ ID NO: 38) |
| I-SceI -6 | TIS |
| I-SceI -7 | TI |
| I-SceI -8 | T |
| I-SceI -9 | complete deletion |

In one embodiment of the invention, the optimized nucleases or optimized versions of I-SceI and its homologs having at least 55%, 58%, 60%, 70%, 80%, 85%, 90%, 92%, 93%, 94%, 95%, 96%, 97%, 98% or 99% sequence identity on amino acid level comprise at least one of the following mutations: L74K, Y75H, Q77K, E130K, T134H, Y199H, M203K, Y205H.

Equally preferred, is to mutate serine at position 229 of the amino acid sequence of wildtype I-SceI as disclosed in SEQ ID NO: 1 to Lys, Ala, Pro, Gly, Glu, Gln, Asp, Asn, Cys, Tyr or Thr. Thereby creating the I-SceI mutants S229K, S229A, S229P, S229G, S229E, S229Q, S229D, S229N, S229C, S229Y, or S229T. Amino acid No. 229 of wildtype I-SceI is amino acid Nr. 230 in SEQ ID NO: 2.

In another embodiment of the invention, the amino acid methionine at position 202 of the amino acid sequence of wildtype I-SceI as disclosed in SEQ ID No. 1 (being amino acid 203 if referenced to SEQ ID No. 2), is mutated to Lys, His or Arg. Thereby creating the I-SceI mutant M202K, M202H and M202R.

Alternatively the amino acid sequence TISSETFLK (SEQ ID NO: 31) may be mutated, e.g. to the amino acid sequence: TIKSETFLK (SEQ ID NO: 39), or AIANQAFLK ESEQ ID NO: 40).

Preferred optimized versions of I-SceI are the deletions I-SceI -1, I-SceI -2, I-SceI -3, I-SceI -4, I-SceI -5, I-SceI -6, I-SceI -7, I-SceI -8, I-SceI -9 and the mutants S229K and S229A, even more preferred are the deletions I-SceI -1, I-SceI -2, I-SceI -3, I-SceI -4, I-SceI -5, I-SceI -6 and the mutant S229K. Most preferred are the deletion I-SceI -5 (SEQ ID NO: 30) and the mutant S229K.

It is also possible to combine the deletions and mutations described above, e.g. by combining the deletion I-SceI -1 with the mutant S229A, thereby creating the amino acid sequence TIASETFL (SEQ ID NO: 41) at the C-terminus.

Further preferred optimized versions of I-SceI are the deletions I-SceI-1, I-SceI-2, I-SceI-3, I-SceI-4, I-SceI-5, I-SceI-6, I-SceI-7, I-SceI-8, I-SceI-9 or the mutants S229K and S229A, in combination with the mutation M202K.

Even more preferred are the deletions I-SceI-1, I-SceI-2, I-SceI-3, I-SceI-4, I-SceI-5, I-SceI-6 or the mutant S229K in combination with the mutation M202K.

In another embodiment of the invention, the amino acids glutamine at position 76, glutamic acid at position 129, or tyrosine at position 198 of the amino acid sequence of wildtype I-SceI as disclosed in SEQ ID No. 1 (being amino acids 77, 130 and 199 if referenced to SEQ ID No. 2), are mutated to Lys, His or Arg. Thereby creating the I-SceI mutants Q76K, Q76H, Q76R, E129K, E129H, E129R, Y198K, Y198H and Y198R.

The deletions and mutations described above will also be applicable to its homologs of I-SceI having at least 55%, 58%, 60%, 70%, 80%, 85%, 90%, 92%, 93%, 94%, 95%, 96%, 97%, 98% or 99% sequence identity on amino acid level and having an amino acid sequence TISSETFLK at the C-terminus.

Accordingly, in one embodiment of the invention, the optimized endonuclease, is an optimized version of I-SceI or one of its homologs having at least 55%, 58%, 60%, 70%, 80%, 85%, 90%, 92%, 93%, 94%, 95%, 96%, 97%, 98% or 99% sequence identity on amino acid level, and having one or more of the mutations or deletions selected from the group of: I-SceI-1, I-SceI-2, I-SceI-3, I-SceI-4, I-SceI-5, I-SceI-6, I-SceI-7, I-SceI-8, I-SceI-9, S229K, S229A, S229P, S229G, S229E, S229Q, S229D, S229N, S229C, S229Y, S229T, M202K, M202H, M202R, Q76K, Q76H, Q76R, E129K, E129H, E129R, Y198K, Y198H and Y198R, wherin the amino acid numbers are referenced to the amino acid sequence as described by SEQ ID NO: 1.

In a further embodiment of the invention, the optimized endonuclease, is an optimized version of I-SceI or one of its homologs having at least 55%, 58%, 60%, 70%, 80%, 85%, 90%, 92%, 93%, 94%, 95%, 96%, 97%, 98% or 99% sequence identity on amino acid level, and having one or more of the mutations or deletions selected from the group of: I-SceI-1, I-SceI-2, I-SceI-3, I-SceI-4, I-SceI-5, I-SceI-6, S229K and M202K, wherin the amino acid numbers are referenced to the amino acid sequence as described by SEQ ID NO: 1.

A particular preferred optimized endonuclease is a wild-type or engineered version of I-SceI, as described by SEQ ID NO: 1 or one of its homologs having at least 55%, 58%, 60%, 70%, 80%, 85%, 90%, 92%, 93%, 94%, 95%, 96%, 97%, 98% or 99% sequence identity on amino acid level and having one or more mutations selected from the groups of:

a) I-SceI-1, I-SceI-2, I-SceI-3, I-SceI-4, I-SceI-5, I-SceI-6, I-SceI-7, I-SceI-8 and I-SceI-9;

b) S229K, S229A, S229P, 5229G, S229E, S229Q, S229D, S229N, S229C, S229Y, S229T, M203K, M203H, M203R, Q77K, Q77H, Q77R, E130K, E130H, E130R, Y199K, Y199H and Y199R;

c) a methionine, valine, glycine, threoninr, serine, alanine, cysteine, glutamic acid, glutamine, aspartic acid, asparagine, isoleucine or histidine after the start methionine of their amino acid sequence; or d) a combination of one or more mutations selected from a) and b), a) and c), b) and c) or a) b) and c) above.

The optimized endonuclease is preferably expressed as a fusion protein with a nuclear localization sequence (NLS). This NLS sequence enables facilitated transport into the nucleus and increases the efficacy of the recombination system. A variety of NLS sequences are known to the skilled worker and described, inter alia, by Jicks G R and Raikhel N V (1995) Annu. Rev. Cell Biol. 11:155-188. Preferred for plant organisms is, for example, the NLS sequence of the SV40 large antigen. Examples are provided in WO 03/060133. The NLS may be heterologous to the endonuclease and/or the DNA binding domain or may be naturally comprised within the endonuclease and/or DNA binding domain.

Another embodiment of the invention are translational fusions comprising optimized endonucleases and heterologous DNA binding domains. The optimized endonucleases comprise mutations as described above and may or may not comprise additional mutations as described above e.g. mutations used to create engineered endonucleases.

Preferred heterologous DNA binding domains are zinc finger or repeat units derived from a transcription activator-like (TAL) effector (also called TAL repeat).

Accordingly, in one embodiment of the invention, the optimized endonuclease is fused to at least one zinc finger domain, or a at least one repeat units derived from a transcription activator-like (TAL) effector, or at least one zinc finger domain and at least one repeat units derived from a transcription activator-like (TAL) effector.

Those fusions might be N-terminal or C-terminal or N- and C-terminal to the optimized endonulease.

For example, it is possible to fuse at least one at least one zinc finger domain to the N-Terminus and at least one zinc finger domain to the C-terminus of the optimized endonuclease, or to fuse at least one zinc finger domain to the N-terminus and at least one repeat unit derived from a transcription activator-like (TAL) effector to the C-terminus of the optimized endonuclease. Alternatively, it is also possible to fuse a combination of at least one zinc-finger domain and at least one repeat unit derived from a transcription activator-like (TAL) effector to the N- or C-terminus or to the N- and C-terminus of an optimized endonuclease. Basically every permutation of those elements is possible.

Zinc finger domains have conserved cysteine and histidine residues that tetrahedycally-coordinate the single zinc atom in each finger domain. In particular, most ZFPs are characterized by finger components of the general sequence:

-Cys-(X)2-4-Cys-(X)12-His-(X)3-5-His- (SEQ ID NO: 42), in which X represents any amino acid (the C2H2 ZFPs). The zinc-finger domains of this most widely represented class contains two cysteines and two histidines with particular spacings. The folded structure of each finger domain contains an antiparallel beta-turn, a finger tip region and a short amphipathic alpha-10 helix. The metal coordinating ligands bind to the zinc ion and, in the case of zif268-type zinc fingers, the short amphipathic a-helix binds in the major groove ofDNA. In addition, the structure of the zinc finger is stabilized by certain conserved hydrophobic amino acid residues (e.g., the residue directly preceding the first conserved Cys and the residue at position +4 of the helical segment of the finger) and by zinc coordination 15 through the conserved cysteine and histidine residues. Canonical C2H2 ZFPs having alterations in positions making direct base contacts, 'supporting' or 'buttressing' residues immediately adjacent to the base-contacting positions, and positions capable of contacting the phosphate backbone ofthe DNA have been described. See, e.g., U.S. Pat. Nos. 6,007,988; 6,013,453; 6,140,081; 6,866,997; 6,746,838; 6,140,081; 6,610,512; 7,101,972; 6,453,242; 6,785,613; 7,013,219; PCT WO 98/53059; Choo et al. (2000) Curro Opin. Struct. Biol. 10:411-416; Segal et al. (2000) Curro Opin. Chern. Biol. 4:34-39.

In addition, zinc finger proteins containing zinc fingers with modified zinc coordinating residues have also been described (see, e.g., U.S. patent application Ser. Nos. 25 20030108880, 20060246567 and 20060246588; the disclosures ofwhich are incorporated by reference).

The terms "repeat unit derived from a transcription activator-like (TAL) effector", "repeat unit" and "TAL repeat" are used exchangebly and are used to describe the modular portion of a repeat domain from a TAL effector, or an artificial version thereof, that contains two amino acids in positions 12 and 13 of the amino acid sequence of a repeat unit that determine recognition of a base pair in a target DNA sequence that such amino acids confer recognition of, as follows: HD for recognition of C/G; NI for recognition of NT; NG for recognition of T/A; NS for recognition of C/G or NT or T/A or G/C; NN for recognition of G/C or A/T; IG for recognition of T/A; N for recognition of C/G; HG for recognition of C/G or T/A; H for recognition of T/A; and NK for recognition of G/C.

(the amino acids H, D, I, G, S, K are described in one-letter code, whereby A, T, C, G refer to the DNA base pairs recognized by the amino acids)

The number of repeat units to be used in a repeat domain can be ascertained by one skilled in the art by routine experimentation. Generally, at least 1.5 repeat units are considered as a minimum, although typically at least about 8 repeat units will be used. The repeat units do not have to be complete repeat units, as repeat units of half the size can be used. A heterologous DNA binding domain of the invention can comprise, for example, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 30.5, 31, 31.5, 32, 32.5, 33, 33.5, 34, 34.5, 35, 35.5, 36, 36.5, 37, 37.5, 38, 38.5, 39, 39.5, 40, 40.5, 41, 41.5, 42, 42.5, 43, 43.5, 44, 44.5, 46, 46.5, 47, 47.5, 48, 48.5, 49, 49.5, 50, 50.5 or more repeat units.

A typical consensus sequence of a repeat with 34 amino acids (in one-letter code) is shown below:

(SEQ ID NO: 19)
LTPEQVVAIASNGGGKQALETVQRLLPVLCQAHG

A further consensus sequence for a repeat unit with 35 amino acids (in one-letter code) is as follows:

(SEQ ID NO: 20)
LTPEQVVAIASNGGGKQALETVQRLLPVLCQAPHD

The repeat units which can be used in one embodiment of the invention have an identity with the consensus sequences described above of at least 35%, 40%, 50%, 60%, 70%, 75%, 80%, 85%, 90% or 95%.

Zinc finger domains as well as TAL repeats can be mutated to bind to any given polynucleotide sequence. Methods how to select appropriate mutations are disclosed in WO0027878, WO03062455, WO08076290, WO08076290, WO9945132 and WO2010/079430 included herein by reference.

It is therefore possible to select a polynucleotide sequence close to a DNA recognition sequence of an optimized endonuclease, and to mutate zinc finger domains or TAL repeats to bind those neighbouring polynucleotide sequence. Those zinc finger domains or TAL repeats can then be used for translational fusions with the respective optimized endonuclease, having the DNA recognition sequence close by.

It is also possible to choose a polynucleotide sequence similar to a DNA recognition sequence of an optimized endonuclease but being inefficiently recognized and or cut by the optimized endonuclease. It is possible to create translational fusions of optimized endonucleases with at least one zinc finger or TAL repeat, binding to a polynucleotide sequence close to this non-optimal DNA recognition site, which will recognize and cut said non-optimal DNA recognition site more efficiently.

It is possible to generate fusions of optimized LAGLIDADG nucleases with a combination of TAL repeat and Zinc finger domains. As TAL effectors are able to recognize AT rich regions, this might compensate the limitation of Zinc finger domains, which preferably bind to GC rich regions.

TAL repeat and Zinc finger domains domains can be used to create N-terminal or C-terminal or N-terminal and C-terminal fusions to optimized LAGLIDADG nucleases, wherein several TAL repeats and or Zinc finger domains as well as combinations of these can be fused at the N-terminal or C-terminal end of the optimized LAGLIDADG nucleases.

Exemplary structures of such fusions are:
N-term-I-SceI-TAL repeat (x)-C-term
N-term-TAL repeat(x) I-SceI- -C-term
N-term-TAL repeat(x) I-SceI-TAL repeat-C-term
N-term-I-SceI-Zinc finger domain (x)-C-term
N-term-Zinc finger domain(x) I-SceI- -C-term
N-term-Zinc finger domain(x) I-SceI-Zinc finger domain (x)-C-term
N-term-TAL repeat(x)-I-SceI-Zinc finger domain(x)-C-term
N-term-Zinc finger domain(x) I-SceI-TAL repeat-C-term
N-term-TAL repeat(x)-I-SceI-Zinc finger domain(x)-C-term
N-term-Zinc finger domain(x) I-SceI-TAL repeat-C-term
N-term-Zinc finger domain(x)-TAL repeat(x)-I-SceI-Zinc finger domain(x)-C-term
N-term-Zinc finger domain(x) I-SceI-TAL repeat(x)-Zinc finger domain(x)-C-term,
wherein (x) means one or several TAL repeats or Zinc finger domains.

In a preferred embodiment, the sequences encoding the optimized endonucleases are modified by insertion of an intron sequence. This prevents expression of a functional enzyme in procaryotic host organisms and thereby facilitates cloning and transformations procedures (e.g., based on *E. coli* or *Agrobacterium*). In eukaryotic organisms, for example plant organisms, expression of a functional enzyme is realized, since plants are able to recognize and "splice" out introns. Preferably, introns are inserted in the optimized endonucleases mentioned as preferred above.

In another preferred embodiment, the amino acid sequences of the optimized endonuclease can be modified by adding a Sec IV secretion signal to the N-, or C-Terminus of the optimized endonuclease.

In a preferred embodiment the SecIV secretion signal is a SecIV secretion signal comprised in Vir proteins of *Agrobacterium*. Examples of such Sec IV secretion signals as well as methods how to apply these are disclosed in WO 01/89283, in Vergunst et al, Positive charge is an important feature of the C-terminal transport signal of the VirB/D4-translocated proteins of *Agrobacterium*, PNAS 2005, 102, 03, pages 832 to 837.

A Sec IV secretion signal might also be added, by adding fragments of a Vir protein or even a complete Vir protein, for example a complete VirE2 protein to an optimized endonuclease, in a similar way as described in the description of WO01/38504, which describes a RecA/VirE2 fusion protein.

In another preferred embodiment the amino acid sequences of the optimized endonuclease can be modified by adding a Sec III secretion signal to the N-, or C-Terminus of the optimized endonuclease. Suitable SecIII secretion signals are for example disclosed in WO 00/02996.

In case a Sec III secretion signal is added, it can be of advantage, to express the optimized endonuclease in a cell, which does also comprise a recombinant construct encoding parts of or a complete functional type III secretion system, in order to overexpress or complement parts or the complete functional type III secretion system in such cell.

Recombinant constructs encoding parts or a complete functional type III secretion system are for example disclosed in WO 00/02996.

If a SecIV secretion signal is added to the optimized endonuclease and the optimized endonuclease is intended to be expressed for example in *Agrobacterium rhizogenes* or in *Agrobacterium tumefaciens*, it is of advantage to adapt the DNA sequence coding for the optimized endonuclease to the codon usage of the expressing organism. Preferably the optimized endonuclease does not have or has only few DNA recognition sequences in the genome of the expressing organism. It is of even greater advantage, if the optimized endonuclease does not have a DNA recognition sequence or less preferred DNA recognition sequence in the *Agrobacterium* genome. In case the optimized endonuclease is intended to be expressed in a prokaryotic organism the optimized endonuclease encoding sequence must not have an intron.

Polynucleotides:

The invention does also comprise isolated polynucleotides coding for the optimized endonucleases described above.

Examples of such isolated polynucleotides are isolated polynucleotides coding for amino acid sequences described by SEQ ID NO: 3, 5, or amino acid sequences having at least 70%, 80%, 90% 91%, 92%, 93%, 94%, 95%, 96%, 97%, 98% or 99% amino acid sequence similarity, preferably having at least 70%, 80%, 90% 91%, 92%, 93%, 94%, 95%, 96%, 97%, 98% or 99% amino acid sequence identity to any one of the amino acid sequences described by SEQ ID NO:2, 3, 5.

Preferably the isolated polynucleotide has a optimized codon usage for expression in a particular host organism, or has a low content of RNA instability motifs, or has a low content of codon repeats, or has a low contend of cryptic splice sites, or has a low content of alternative start codons, or has a low content of restriction sites, or has a low content of RNA secondary structures or has any combination of these features.

The codon usage of the isolated polypeptide may be optimized e.g. for the expression in plants, preferably in a plant selected from the group comprising: rice, corn, wheat, rape seed, sugar cane, sunflower, sugar beet, potato or tobacco.

Preferably the isolated polynucleotide is combined with a promoter sequence and a terminator sequence suitable to form a functional expression cassette for expression of the optimized endonuclease in a particular host organism.

Suitable promoters are for example constitutive, heat- or pathogen-inducible, or seed, pollen, flower or fruit specific promoters.

The person skilled in the art knows numerous promoters having those features.

For example several constitutive promoters in plants are known. Most of them are derived from viral or bacterial sources such as the nopaline synthase (nos) promoter (Shaw et al. (1984) Nucleic Acids Res. 12 (20):7831-7846), the mannopine synthase (mas) promoter (Co-mai et al. (1990) Plant Mol Biol 15(3):373-381), or the octopine synthase (ocs) pro-moter (Leisner and Gelvin (1988) Proc Natl Acad Sci USA 85 (5):2553-2557) from *Agrobacterium tumefaciens* or the CaMV35S promote from the Cauliflower Mosaic Vi-rus (U.S. Pat. No. 5,352,605). The latter was most frequently used in constitutive expression of transgenes in plants (Odell et al. (1985) Nature 313:810-812; Battraw and Hall (1990) Plant Mol Biol 15:527-538; Benfey et al. (1990) EMBO J 9(69):1677-1684; U.S. Pat. No. 5,612,472). However, the CaMV 35S promoter demonstrates variability not only in dif-ferent plant species but also in different plant tissues (Atanassova et al. (1998) Plant Mol Biol 37:275-85; Battraw and Hall (1990) Plant Mol Biol 15:527-538; Holtorf et al. (1995) Plant Mol Biol 29:637-646 ; Jefferson et al. (1987) EMBO J 6:3901-3907). An additional disadvantage is an interference of the transcription regulating activity of the 35S promoter with wild-type CaMV virus (Al-Kaff et al. (2000) Nature Biotechnology 18 :995-99). Another viral promoter for constitutive expression is the Sugarcane bacilliform badnavirus (ScBV) promoter (Schenk et al. (1999) Plant Mol Biol 39 (6) :1221-1230).

Several plant constitutive promoters are described such as the ubiquitin promoter from *Arabidopsis thaliana* (Callis et al. (1990) J Biol Chem 265:12486-12493; Holtorf S et al. (1995) Plant Mol Biol 29:637-747), which—however—is reported to be unable to regu-late expression of selection markers (WO03102198), or two maize ubiquitin promoter (Ubi-1 and Ubi-2; U.S. Pat. Nos. 5,510,474; 6,020,190; 6,054,574), which beside a consti-tutive expression profile demonstrate a heat-shock induction (Christensen et al. (1992) Plant. Mol. Biol. 18(4):675-689). A comparison of specificity and expression level of the CaMV 35S, the barley thionine promoter, and the *Arabidopsis ubiquitin* promoter based on stably transformed *Arabidopsis* plants demonstrates a high expression rate for the CaMV 35S promoter, while the thionine promoter was inactive in most lines and the ubil promoter from *Arabisopsis* resulted only in moderate expression activity (Holtorf et al. (1995) Plant Mol Biol 29 (4):637-6469).

Vectors:

The polynucleotides described above may be comprised in a DNA vector suitable for transformation, transfection, cloning or overexpression.

In one example, the polynucleotides described above are comprised in a vector for transformation of non-human organisms or cells, preferably the non-human organisms are plants or plant cells.

The vectors of the invention usually comprise further functional elements, which may include but shall not be limited to:

i) Origins of replication which ensure replication of the expression cassettes or vectors according to the invention in, for example, *E. coli*. Examples which may be mentioned are ORI (origin of DNA replication), the pBR322 on or the P15A ori (Sam-brook et al.: Molecular Cloning. A Laboratory Manual, 2nd ed. Cold Spring Harbor Laboratory Press, Cold Spring Harbor, N.Y., 1989).

ii) Multiple cloning sites (MCS) to enable and facilitate the insertion of one or more nucleic acid sequences.

iii) Sequences which make possible homologous recombination or insertion into the genome of a host organism.

iv) Elements, for example border sequences, which make possible the *Agrobacterium*-mediated transfer in plant cells for the transfer and integration into the plant genome, such as, for example, the right or left border of the T-DNA or the vir region.

The Marker Sequence

The term "marker sequence" is to be understood in the broad sense to include all nucleotide sequences (and/or polypeptide sequences translated therefrom) which facilitate detection, identification, or selection of transformed cells, tissues or organism (e.g., plants). The terms "sequence allowing selection of a transformed plant material", "selection marker" or "selection marker gene" or "selection marker protein" or "marker" have essentially the same meaning.

Markers may include (but are not limited to) selectable marker and screenable marker. A selectable marker confers to the cell or organism a phenotype resulting in a growth or viability difference. The selectable marker may interact with a selection agent (such as a herbicide or anti-biotic or prodrug) to bring about this phenotype. A screenable marker confers to the cell or organism a readily detectable phenotype, preferably a visibly detectable phenotype such a color or staining. The screenable marker may interact with a screening agent (such as a dye) to bring about this phenotype.

Selectable marker (or selectable marker sequences) comprise but are not limited to a) negative selection marker, which confers resistance against one or more toxic (in case of plants phytotoxic) agents such as an antibiotica, herbicides or other biocides, b) counter selection marker, which confer a sensitivity against certain chemical compounds (e.g., by converting a non-toxic compound into a toxic compound), and c) positive selection marker, which confer a growth advantage (e.g., by expression of key elements of the cytokinin or hormone biosynthesis leading to the production of a plant hormone e.g., auxins, gibberllins, cytokinins, abscisic acid and ethylene; Ebi-numa H et al. (2000) Proc Natl Acad Sci USA 94:2117-2121).

When using negative selection markers, only cells or plants are selected which comprise said negative selection marker. When using counter selection marker, only cells or plants are selected which lack said counter-selection marker. Counter-selection marker may be employed to verify successful excision of a sequence (comprising said counter-selection marker) from a genome. Screenable marker sequences include but are not limited to reporter genes (e. g. luciferase, glucuronidase, chloramphenicol acetyl transferase (CAT, etc.). Preferred marker sequences include but shall not be limited to:

i) Negative Selection Marker

As a rule, negative selection markers are useful for selecting cells which have success-fully undergone transformation. The negative selection marker, which has been introduced with the DNA construct of the invention, may confer resistance to a biocide or phytotoxic agent (for example a herbicide such as phosphinothricin, glyphosate or bromoxynil), a metabolism inhibitor such as 2-deoxyglucose-6-phosphate (WO 98/45456) or an antibiotic such as, for example, tetracyclin, ampicillin, kanamycin, G 418, neomycin, bleomycin or hygromycin to the cells which have successfully undergone transformation. The negative selection marker permits the selection of the trans-formed cells from untransformed cells (McCormick et al. (1986) Plant Cell Reports 5:81-84). Negative selection marker in a vector of the invention may be employed to confer resistance in more than one organism. For example a vector of the invention may comprise a selection marker for amplification in bacteria (such as *E. coli* or *Agrobacterium*) and plants. Examples of selectable markers for *E. coli* include: genes specifying resistance to antibiotics, i.e., ampicillin, tetracycline, kanamycin, erythromycin, or genes conferring other types of selectable enzymatic activities such as galactosidase, or the lactose operon. Suitable selectable markers for use in mammalian cells include, for example, the dihydrofolate reductase gene (DHFR), the thymidine kinase gene (TK), or prokaryotic genes conferring drug resistance, gpt (xanthine-guanine phosphoribosyltransferase, which can be selected for with mycophenolic acid; neo (neomycin phosphotransferase), which can be selected for with G418, hygromycin, or puromycin; and DHFR (dihydrofolate reductase), which can be selected for with methotrexate (Mulligan & Berg (1981) Proc Natl Acad Sci USA 78:2072; Southern & Berg (1982) J Mol Appl Genet 1: 327). Selection markers for plant cells often confer resistance to a biocide or an antibiotic, such as, for example, kanamycin, G 418, bleomycin, hygromycin, or chloramphenicol, or herbicide resistance, such as resistance to chlorsulfuron or Basta.

Especially preferred negative selection markers are those which confer resistance to herbicides. Examples of negative selection markers are:

DNA sequences which encode phosphinothricin acetyl-transferases (PAT), which acetylates the free amino group of the glutamine synthase inhibitor phosphinothricin (PPT) and thus brings about detoxification of PPT (de Block et al. (1987) EMBO J 6:2513-2518) (also referred to as Bialophos—resistence gene bar; EP 242236), 5-enolpyruvylshikimate-3-phosphate synthase genes (EPSP synthase genes), which confer resistence to Glyphosate-(N-(phosphonomethyl)glycine), the gox gene, which encodes the Glyphosate-degrading enzyme Glyphosate oxi-doreductase, the deh gene (encoding a dehalogenase which inactivates Dalapon-), acetolactate synthases which confer resistance to sulfonylurea and imidazolinone, bxn genes which encode Bromoxynil-degrading nitrilase enzymes, the kanamycin, or G418, resistence gene (NPTII). The NPTII gene encodes a neomycin phosphotransferase which reduces the inhibitory effect of kanamycin, neomycin, G418 and paromomycin owing to a phosphorylation reaction (Beck et al (1982) Gene 19: 327), the DOGR1 gene. The DOGR1 gene has been isolated from the yeast *Saccharomyces cerevisiae* (EP 0 807 836). It encodes a 2-deoxyglucose-6-phosphate phosphatase which confers resistence to 2-DOG (Randez-Gil et al. (1995) Yeast 11:1233-1240).

the hyg gene, which codes for the enzyme hygromycin phosphotransferase and confers resistance to the antibiotic hygromycin (Gritz and Davies (1983) Gene 25: 179);

especially preferred are negative selection markers that confer resistance against the toxic effects imposed by D-amino acids like e.g., D-alanine and D-serine (WO 03/060133; Erikson 2004). Especially preferred as negative selection marker in this contest are the daol gene (EC: 1.4.3.3: GenBank Acc.-No.: U60066) from the yeast *Rhodotorula gracilis* (*Rhodosporidium toruloides*) and the *E. coli* gene dsdA (D-serine dehydratase (D-serine deaminase) (EC: 4.3.1.18; GenBank Acc.-No.: J01603).

ii) Positive Selection Marker

Positive selection marker comprise but are not limited to growth stimulating selection marker genes like isopentenyl-transferase from *Agrobacterium tumefaciens* (strain: P022; Genbank Acc.-No.: AB025109) may—as a key enzyme of the cytokinin biosynthesis—facilitate regeneration of trans-formed plants (e.g., by selection on cyto-kinin-free medium). Corresponding selection methods are described (Ebinuma H et al. (2000) Proc Natl Acad Sci USA 94:2117-2121; Ebi-numa H et al. (2000) Selection of Marker-free transgenic plants using the oncogenes (ipt, rolA, B, C) of *Agrobacterium* as selectable markers, In Molecular Biology of Woody Plants. Kluwer Academic Publishers). Additional positive selection markers, which confer a growth advantage to a transformed plant in comparison with a non-transformed one, are described e.g., in EP-A 0 601 092. Growth stimulation selection markers may include (but shall not be limited to) beta-Glucuronidase (in combination with e.g., a cytokinin glucuronide), mannose-6-phosphate isomerase (in combination with mannose), UDP-galactose-4-epimerase (in combination with e.g., galactose), wherein mannose-6-phosphate isomerase in combination with mannose is especially preferred.

iii) Counter Selection Markers

Counter-selection marker enable the selection of organisms with successfully deleted sequences (Koprek T et al. (1999) Plant J 19(6):719-726). TK thymidine kinase (TK) and diphtheria toxin A fragment (DT-A), codA gene encoding a cytosine deaminase (Gleve A P et al. (1999) Plant Mol Biol 40(2):223-35; Pereat R I et al. (1993) Plant Mol Biol 23(4): 793-799; Stougaard J (1993) Plant J 3:755-761), the cytochrome P450 gene (Koprek et al. (1999) Plant J 16:719-726), genes encoding a haloalkane dehalogenase (Naested H (1999) Plant J 18:571-576), the iaaH gene (Sundaresan V et al. (1995) Genes & Development 9:1797-1810), the tms2 gene (Fedoroff N V & Smith D L (1993) Plant J 3:273-289), and D-amino acid oxidases causing toxic effects by conversion of D-amino acids (WO 03/060133).

In a preferred embodiment the excision cassette includes at least one of said counter-selection markers to distinguish plant cells or plants with successfully excised sequences from plant which still contain these. In a more preferred embodiment the excision cassette of the invention comprises a dual-function marker i.e. a marker with can be employed as both a negative and a counter selection marker depending on the substrate employed in the selection scheme. An example for a dual-function marker is the daol gene (EC: 1.4.3.3: GenBank Acc.-No.: U60066) from the yeast *Rhodotorula gracilis*, which can be employed as negative selection marker with D.-amino acids such as D-alanine and D-serine, and as counter-selection marker with D-amino acids such as D-isoleucine and D-valine (see European Patent Appl. No.: 04006358.8)

iv) Screenable Marker (Reporter Genes)

Screenable marker (such as reporter genes) encode readily quantifiable or detectable proteins and which, via intrinsic color or enzyme activity, ensure the assessment of the transformation efficacy or of the location or timing of expression. Especially preferred are genes encoding reporter proteins (see also Schenborn E, Groskreutz D. (1999) Mol Biotechnol 13(1):29-44) such as "green fluorescence protein" (GFP) (Chuff W L et al. (1996) Curr Biol 6:325-330; Lef-fel S M et al. (1997) Biotechniques 23(5):912-8; Sheen et al. (1995) Plant J 8(5):777-784; Haseloff et al. (1997) Proc Natl Acad Sci USA 94(6):2122-2127; Reichel et al. (1996) Proc Natl Acad Sci USA 93(12):5888-5893; Tian et al. (1997) Plant Cell Rep 16:267-271; WO 97/41228).

Chloramphenicol transferase, luciferase (Millar et al. (1992) Plant Mol Biol Rep 10:324-414; Ow et al. (1986) Science 234:856-859) permits selection by detection of bioluminescence, beta-galactosidase, encodes an enzyme for which a variety of chromogenic substrates are available, beta-glucuronidase (GUS) (Jefferson et al. (1987) EMBO J 6:3901-3907) or the uidA gene, which encodes an enzyme for a variety of chromogenic substrates, R locus gene product: protein which regulates the production of anthocyanin pig-ments (red coloration) in plant tissue and thus makes possible the direct analysis of the promoter activity without the addition of additional adjuvants or chromogenic substrates (Dellaporta et al. (1988) In: Chromosome Structure and Function: Impact of New Concepts, 18th Stadler Genetics Symposium, 11:263-282,), beta-lactamase (Sutcliffe (1978) Proc Natl Acad Sci USA 75:3737-3741), enzyme for a variety of chromogenic substrates (for example PADAC, a chromogenic cephalosporin), xylE gene product (Zukowsky et al. (1983) Proc Natl Acad Sci USA 80:1101-1105), catechol dioxygenase capable of converting chromogenic catechols, alpha-amylase (Ikuta et al. (1990) Bio/technol. 8:241-242), tyrosinase (Katz et al. (1983) J Gene Microbiol 129:2703-2714), enzyme which oxi-dizes tyrosine to give DOPA and dopaquinone which subsequently form melanine, which is readily detectable, aequorin (Prasher et al. (1985) Biochem Biophys Res Commun 126(3):1259-1268), can be used in the calcium-sensitive bioluminescence detection.

Target Organisms

Any organism suitable for transformation or delivery of an optimized endonuclease can be used as target organism. This includes prokaryotes, eukaryotes, and archaea, in particular human or animal cells, animals, plants, fungi or yeasts, preferably plants, fungi or yeasts.

In one embodiment the target organism is a plant.

The term "plant" includes whole plants, shoot vegetative organs/structures (e. g. leaves, stems and tubers), roots, flowers and floral organs/structures (e. g. bracts, sepals, petals, stamens, carpels, anthers and ovules), seeds (including embryo, endosperm, and seed coat) and fruits (the mature ovary), plant tissues (e. g. vascular tissue, ground tissue, and the like) and cells (e. g. guard cells, egg cells, trichomes and the like), and progeny of same. The class of plants that can be used in the method of the invention is generally as broad as the class of higher and lower plants amenable to transformation techniques, including angiosperms (monocotyledonous and dicotyledonous plants), gymnosperms, ferns, and multicellular algae. It includes plants of a variety of ploidy levels, including aneuploid, polyploid, diploid, haploid and hemizygous.

Included within the scope of the invention are all genera and species of higher and lower plants of the plant kingdom. Included are furthermore the mature plants, seed, shoots and seedlings, and parts, propagation material (for example seeds and fruit) and cultures, for example cell cultures, derived therefrom.

Preferred are plants and plant materials of the following plant families: Amaranthaceae, Brassicaceae, Carophyllaceae, Chenopodiaceae, Compositae, Cucurbitaceae, Labiatae, Leguminosae, Papilionoideae, Liliaceae, Linaceae, Malvaceae, Rosaceae, Saxi-fragaceae, Scrophulariaceae, Solanaceae, Tetragoniaceae.

Annual, perennial, monocotyledonous and dicotyledonous plants are preferred host organisms for the generation of transgenic plants. The use of the recombination system, or method according to the invention is furthermore advantageous in all ornamental plants, useful or ornamental trees, flowers, cut flowers, shrubs or turf. Said plant may include—but shall not be limited to—bryophytes such as, for example, Hepaticae (hepaticas) and Musci (mosses); pteridophytes such as ferns, horsetail and club-mosses; gymnosperms such as conifers, cycads, ginkgo and Gnetaeae; algae such as Chlorophyceae, Phaeophpyceae, Rhodophyceae, Myxophyceae, Xanthophyceae, Bacillariophyceae (diatoms) and Euglenophyceae.

Plants for the purposes of the invention may comprise the families of the Rosaceae such as rose, Ericaceae such as rhododendrons and azaleas, Euphorbiaceae such as poinsettias and croton, Caryophyllaceae such as pinks, Solanaceae such as petunias, Gesneriaceae such as African violet, Balsaminaceae such as touch-me-not, Orchida-ceae such as orchids, Iridaceae such as gladioli, iris, freesia and crocus, Compositae such as marigold, Geraniaceae such as geraniums, Liliaceae such as drachaena, Moraceae such as ficus, Araceae such as philodendron and many others.

The transgenic plants according to the invention are furthermore selected in particular from among dicotyledonous crop plants such as, for example, from the families of the Leguminosae such as pea, alfalfa and soybean; Solanaceae such as tobacco and and many others; the family of the Umbelliferae, particularly the genus *Daucus* (very particularly the species *carota* (carrot)) and *Apium* (very particularly the species *graveolens dulce* (celery)) and many others; the family of the Solanaceae, particularly the genus *Lycopersicon*, very particularly the species *esculentum* (tomato) and the genus *Solanum*, very particularly the species *tuberosum* (potato) and *melongena* (au-bergine) and many others; and the genus *Capsicum*, very particularly the species *an-num* (pepper) and many others; the family of the Leguminosae, particularly the genus *Glycine*, very particularly the species *max* (soybean) and many others; and the family of the Cruciferae, particularly the genus *Brassica*, very particularly the species *napus* (oilseed rape), *campestris* (beet), *oleracea* cv Tastie (cabbage), *oleracea* cv Snowball Y (cauliflower) and *oleracea* cv Emperor (broccoli); and the genus *Arabidopsis*, very particularly the species *thaliana* and many others; the family of the Compositae, par-ticularly the genus *Lactuca*, very particularly the species *sativa* (lettuce) and many others.

The transgenic plants according to the invention are selected in particular among monocotyledonous crop plants, such as, for example, cereals such as wheat, barley, sorghum and millet, rye, triticale, maize, rice or oats, and sugar cane. Especially preferred are *Arabidopsis thaliana*, *Nicotiana tabacum*, oilseed rape, soybean, corn (maize), wheat, linseed, potato and tagetes.

Plant organisms are furthermore, for the purposes of the invention, other organisms which are capable of photosynthetic activity, such as, for example, algae or cyanobacteria, and also mosses. Preferred algae are green algae, such as, for example, algae of the genus *Haematococcus, Phaedactylum tricornatum, Volvox* or *Dunaliella*.

Genetically modified plants according to the invention which can be consumed by humans or animals can also be used as food or feedstuffs, for example directly or following processing known in the art.

Construction of Polynucleotide Constructs

Typically, polynucleotide constructs (e.g., for an expression cassette) to be introduced into non-human organism or cells, e.g. plants or plant cells are prepared using transgene expression techniques. Recombinant expression techniques involve the construction of recombinant nucleic acids and the expression of genes in transfected cells. Molecular cloning techniques to achieve these ends are known in the art. A wide variety of cloning and in vitro amplification methods suitable for the construction of recombinant nucleic acids are well-known to persons of skill in the art. Examples of these techniques and instructions sufficient to direct persons of skill in the art through many cloning exercises are found in Berger and Kimmel, Guide to Molecular Cloning Techniques, Methods in Enzymology, Vol. 152, Academic Press, hic., San Diego, Calif. (Berger); Current Protocols in Molecular Biology, F. M. Ausubel et al., eds., Current Protocols, a joint venture between Greene Publish-ing Associates, Inc. and John Wiley & Sons, Inc., (1998 Supplement), T. Maniatis, E. F. Fritsch and J. Sambrook, Molecular Cloning: A Laboratory Manual, Cold Spring Harbor Laboratory, Cold Spring Harbor, N.Y. (1989), in T. J. Silhavy, M. L. Berman and L. W. Enquist, Experiments with Gene Fusions, Cold Spring Harbor Laboratory, Cold Spring Harbor, N.Y. (1984). Preferably, the DNA constructs employed in the invention are generated by joining the abovementioned essential constituents of the DNA construct together in the abovementioned sequence using the recombination and cloning techniques with which the skilled worker is familiar.

The construction of polynucleotide constructs generally requires the use of vectors able to replicate in bacteria. A plethora of kits are commercially available for the purification of plasmids from bacteria. The isolated and purified plasmids can then be further manipulated to produce other plasmids, used to transfect cells or incorporated into *Agrobacterium tumefaciens* or *Agrobacterium rhizogenes* to infect and transform plants. Where *Agrobacterium* is the means of transformation, shuttle vectors are constructed.

Methods for Introducing Constructs into Target Cells

A DNA construct employed in the invention may advantageously be introduced into cells using vectors into which said DNA construct is inserted. Examples of vectors may be plasmids, cosmids, phages, viruses, retroviruses or agrobacteria. In an advantageous embodiment, the expression cassette is introduced by means of plasmid vectors. Preferred vectors are those which enable the stable integration of the expression cassette into the host genome.

A DNA construct can be introduced into the target plant cells and/or organisms by any of the several means known to those of skill in the art, a procedure which is termed transformation (see also Keown et al. (1990) Meth Enzymol 185:527-537). For instance, the DNA constructs can be introduced into cells, either in culture or in the organs of a plant by a variety of conventional techniques. For example, the DNA constructs can be introduced directly to plant cells using ballistic methods, such as DNA particle bombardment, or the DNA construct can be introduced using techniques such as electroporation and microinjection of cells. Particle-mediated transformation techniques (also known as "biolistics") are described in, e.g., Klein et al. (1987) Nature 327:70-73; Vasil Vet al. (1993) BiolTechnol 11:1553-1558; and Becker D et al. (1994) Plant J 5:299-307. These methods involve penetration of cells by small particles with the nucleic acid either within the matrix of small beads or particles, or on the surface. The biolistic PDS-1000 Gene Gun (Biorad, Hercules, Calif.) uses helium pressure to accelerate DNA-coated gold or tungsten microcarriers toward target cells. The process is applicable to a wide range of tissues and cells from organisms, including plants. Other transformation methods are also known to those of skill in the art.

Microinjection techniques are known in the art and are well described in the scientific and patent literature. Also, the cell can be permeabilized chemically, for example using polyethylene glycol, so that the DNA can enter the cell by diffusion. The DNA can also be introduced by protoplast fusion with other DNA-containing units such as minicells, cells, lysosomes or liposomes. The introduction of DNA constructs using polyethylene glycol (PEG) precipitation is described in Paszkowski et al. (1984) EMBO J 3:2717. Liposome-based gene delivery is e.g., described in WO 93/24640; Mannino and Gould-Fogerite (1988) BioTechniques 6(7):682-691; U.S. Pat. No. 5,279,833; WO 91/06309; and Feigner et al. (1987) Proc Natl Acad Sci USA 84:7413-7414).

Another suitable method of introducing DNA is electroporation, where the cells are permeabilized reversibly by an electrical pulse. Electroporation techniques are described in Fromm et al. (1985) Proc Natl Acad Sci USA 82:5824. PEG-mediated transformation and electroporation of plant protoplasts are also discussed in Lazzeri P (1995) Methods Mol Biol 49:95-106. Preferred general methods which may be mentioned are the calcium-phosphate-mediated transfection, the DEAE-dextran-mediated transfection, the cationic lipid-mediated transfection, electroporation, transduction and infection. Such methods are known to the skilled worker and described, for example, in Davis et al., Basic Methods In Molecular Biology (1986). For a review of gene transfer methods for plant and cell cultures, see, Fisk et al. (1993) Scientia Horticulturae 55:5-36 and Potrykus (1990) CIBA Found Symp 154:198.

Methods are known for introduction and expression of heterologous genes in both monocot and dicot plants. See, e.g., U.S. Pat. Nos. 5,633,446, 5,317,096, 5,689,052, 5,159,135, and 5,679,558; Weising et al. (1988) Ann. Rev. Genet. 22: 421-477. Transformation of monocots in particular can use various techniques including electroporation (e.g., Shimamoto et al. (1992) Nature 338:274-276; biolistics (e.g., EP-A1 270,356); and *Agrobacterium* (e.g., Bytebier et al. (1987) Proc Natl Acad Sci USA 84:5345-5349).

In plants, methods for transforming and regenerating plants from plant tissues or plant cells with which the skilled worker is familiar are exploited for transient or stable transformation. Suitable methods are especially protoplast transformation by means of poly-ethylene-glycol-induced DNA uptake, biolistic methods such as the gene gun ("particle bombardment" method), electroporation, the incubation of dry embryos in DNA-containing solution, sonication and microinjection, and the transformation of intact cells or tissues by micro- or macroinjection into tissues or embryos, tissue electroporation, or vacuum infiltration of seeds. In the case of injection or electroporation of DNA into plant cells, the plasmid used does not need to meet any particular requirement. Simple plasmids such as those of the pUC series may be used. If intact plants are to be regenerated from the transformed cells, the presence of an additional selectable marker gene on the plasmid is useful.

In addition to these "direct" transformation techniques, transformation can also be carried out by bacterial infection by means of *Agrobacterium tumefaciens* or *Agrobacterium rhizogenes*. These strains contain a plasmid (Ti or Ri plasmid). Part of this plasmid, termed T-DNA (transferred DNA), is transferred to the plant following *Agrobacterium* infection and integrated into the genome of the plant cell.

For *Agrobacterium*-mediated transformation of plants, a DNA construct of the invention may be combined with suitable T-DNA flanking regions and introduced into a conventional *Agrobacterium tumefaciens* host vector. The virulence functions of the *A. tumefaciens* host will direct the insertion of a transgene and adjacent marker gene(s) (if present) into the plant cell DNA when the cell is infected by the bacteria. *Agrobacterium tumefaciens*-mediated transformation techniques are well described in the scientific literature. See, for example, Horsch et al. (1984) Science 233:496-498, Fraley et al. (1983) Proc Natl Acad Sci USA 80:4803-4807, Hooykaas (1989) Plant Mol Biol 13:327-336, Horsch R B (1986) Proc Natl Acad Sci USA 83(8):2571-2575), Bevans et al. (1983) Nature 304:184-187, Bechtold et al. (1993) Comptes Rendus De L'Academie Des Sciences Serie III—Sciences De La Vie—Life Sciences 316:1194-1199, Valvekens et al. (1988) Proc Natl Acad Sci USA 85:5536-5540.

A DNA construct of the invention is preferably integrated into specific plasmids, either into a shuttle, or intermediate, vector or into a binary vector). If, for example, a Ti or Ri plasmid is to be used for the transformation, at least the right border, but in most cases the right and the left border, of the Ti or Ri plasmid T-DNA is linked with the expression cassette to be introduced as a flanking region. Binary vectors are preferably used. Bi-nary vectors are capable of replication both in *E. coli* and in *Agrobacterium*. As a rule, they contain a selection marker gene and a linker or polylinker flanked by the right or left T-DNA flanking sequence. They can be transformed directly into *Agrobacterium* (Holsters et al. (1978) Mol Gen Genet 163:181-187). The selection marker gene permits the selection of transformed agrobacteria and is, for example, the nptII gene, which imparts resistance to kanamycin. The *Agrobacterium*, which acts as host organism in this case, should already contain a plasmid with the vir region. The latter is required for transferring the T-DNA to the plant cell. An *Agrobacterium* thus transformed can be used for transforming plant cells.

Many strains of *Agrobacterium tumefaciens* are capable of transferring genetic material—for example a DNA constructs according to the invention—, such as, for example, the strains EHA101(pEHA101) (Hood E E et al. (1996) J Bacteriol 168(3):1291-1301), EHA105(pEHA105) (Hood et al. 1993, Transgenic Research 2, 208-218), LBA4404(pAL4404) (Hoekema et al. (1983) Nature 303:179-181), C58C1 (pMP90) (Koncz and Schell (1986) Mol Gen Genet 204,383-396) and C58C1(pGV2260) (De-blaere et al. (1985) Nucl Acids Res. 13, 4777-4788).

The agrobacterial strain employed for the transformation comprises, in addition to its disarmed Ti plasmid, a binary plasmid with the T-DNA to be transferred, which, as a rule, comprises a gene for the selection of the transformed cells and the gene to be transferred. Both genes must be equipped with transcriptional and translational initiation and termination signals. The binary plasmid can be transferred into the agrobacterial strain for example by electroporation or other transformation methods (Mozo & Hooykaas (1991) Plant Mol Biol 16:917-918). Coculture of the plant explants with the agrobacterial strain is usually performed for two to three days.

A variety of vectors could, or can, be used. In principle, one differentiates between those vectors which can be employed for the *Agrobacterium*-mediated transformation or agroinfection, i.e. which comprise a DNA construct of the invention within a T-DNA, which indeed permits stable integration of the T-DNA into the plant genome. Moreover, border-sequence-free vectors may be employed, which can be transformed into the plant cells for example by particle bombardment, where they can lead both to transient and to stable expression.

The use of T-DNA for the transformation of plant cells has been studied and described intensively (EP-A1 120 516; Hoekema, In: The Binary Plant Vector System, Offset-drukkerij Kanters B. V., Alblasserdam, Chapter V; Fraley et al. (1985) Crit Rev Plant Sci 4:1-45 and An et al. (1985) EMBO J 4:277-287). Various binary vectors are known, some of which are commercially available such as, for example, pBIN19 (Clontech Laboratories, Inc. USA).

To transfer the DNA to the plant cell, plant explants are cocultured with *Agrobacterium tumefaciens* or *Agrobacterium rhizogenes*. Starting from infected plant material (for example leaf, root or stalk sections, but also protoplasts or suspensions of plant cells), intact plants can be regenerated using a suitable medium which may contain, for example, antibiotics or biocides for selecting transformed cells. The plants obtained can then be screened for the presence of the DNA introduced, in this case a DNA construct according to the invention. As soon as the DNA has integrated into the host genome, the genotype in question is, as a rule, stable and the insertion in question is also found in the subsequent generations. As a rule, the expression cassette integrated contains a selection marker which confers a resistance to a biocide (for example a herbicide) or an antibiotic such as kanamycin, G 418, bleomycin, hygromycin or phosphinotricin and the like to the transformed plant. The selection marker permits the selection of transformed cells (McCormick et al., Plant Cell Reports 5 (1986), 81-84). The plants obtained can be cultured and hybridized in the customary fashion. Two or more generations should be grown in order to ensure that the genomic integration is stable and hereditary.

The abovementioned methods are described, for example, in B. Jenes et al., Techniques for Gene Transfer, in: Transgenic Plants, Vol. 1, Engineering and Utilization, edited by S D Kung and R Wu, Academic Press (1993), 128-143 and in Potrykus (1991) Annu Rev Plant Physiol Plant Molec Biol 42:205-225). The construct to be expressed is preferably cloned into a vector which is suitable for the transformation of Agrobacterium tumefaciens, for example pBin19 (Bevan et al. (1984) Nucl Acids Res 12:8711).

The DNA construct of the invention can be used to confer desired traits on essentially any plant. One of skill will recognize that after DNA construct is stably incorporated in transgenic plants and confirmed to be operable, it can be introduced into other plants by sexual crossing. Any of a number of standard breeding techniques can be used, depending upon the species to be crossed.

The optimized endonucleases may alternatively be expressed transiently. The chimeric endonuclease may be transiently expressed as a DNA or RNA delivered into the target cell and/or may be delivered as a protein. Delivery as a protein may be achieved with the help of cell penetrating peptides or by fusion with SEcIV signal peptides fused to the nucleases or chimeric endonucleases, which mediate the secretion from a delivery organism into a cell of a target organism e.g. from Agrobacterium rhizogenes or Agrobacterium tumefaciens to a plant cell.

Regeneration of Transgenic Plants

Transformed cells, i.e. those which comprise the DNA integrated into the DNA of the host cell, can be selected from untransformed cells if a selectable marker is part of the DNA introduced. A marker can be, for example, any gene which is capable of conferring a resistance to antibiotics or herbicides (for examples see above). Transformed cells which express such a marker gene are capable of surviving in the presence of concentrations of a suitable antibiotic or herbicide which kill an untransformed wild type. As soon as a transformed plant cell has been generated, an intact plant can be obtained using methods known to the skilled worker. For example, callus cultures are used as starting material. The formation of shoot and root can be induced in this as yet undifferentiated cell biomass in the known fashion. The shoots obtained can be planted and cultured.

Transformed plant cells, derived by any of the above transformation techniques, can be cultured to regenerate a whole plant which possesses the transformed genotype and thus the desired phenotype. Such regeneration techniques rely on manipulation of certain phytohormones in a tissue culture growth medium, typically relying on a biocide and/or herbicide marker that has been introduced together with the desired nucleotide sequences. Plant regeneration from cultured protoplasts is described in Evans et al., Protoplasts Isolation and Culture, Handbook of Plant Cell Culture, pp. 124176, Macmillian Publishing Company, New York (1983); and in Binding, Regeneration of Plants, Plant Protoplasts, pp. 21-73, CRC Press, Boca Raton, (1985). Regeneration can also be obtained from plant callus, explants, somatic embryos (Dandekar et al. (1989) J Tissue Cult Meth 12:145; McGranahan et al. (1990) Plant Cell Rep 8:512), organs, or parts thereof.

Such regeneration techniques are described generally in Klee et al. (1987) Ann Rev Plant Physiol 38:467-486.

Combination with Other Recombination Enhancing Techniques

In a further preferred embodiment, the efficacy of the recombination system is in-creased by combination with systems which promote homologous recombination. Such systems are described and encompass, for example, the expression of proteins such as RecA or the treatment with PARP inhibitors. It has been demonstrated that the intrachromosomal homologous recombination in tobacco plants can be increased by using PARP inhibitors (Puchta H et al. (1995) Plant J. 7:203-210). Using these inhibitors, the homologous recombination rate in the recombination cassette after induction of the sequence-specific DNA double-strand break, and thus the efficacy of the deletion of the transgene sequences, can be increased further. Various PARP inhibitors may be employed for this purpose. Preferably encompassed are inhibitors such as 3-aminobenzamide, 8-hydroxy-2-methylquinazolin-4-one (NU1025), 1,11b-dihydro-(2H) benzopyrano(4,3,2-de)isoquinolin-3-one (GPI 6150), 5-aminoisoquino-linone, 3,4-dihydro-5-(4-(1-piperidinyl)butoxy)-1(2H)-isoquinolinone, or the compounds described in WO 00/26192, WO 00/29384, WO 00/32579, WO 00/64878, WO 00/68206, WO 00/67734, WO 01/23386 and WO 01/23390.

In addition, it was possible to increase the frequency of various homologous recombination reactions in plants by expressing the E. coli RecA gene (Reiss B et al. (1996) Proc Natl Acad Sci USA 93(7):3094-3098). Also, the presence of the protein shifts the ratio between homologous and illegitimate DSB repair in favor of homologous repair (Reiss B et al. (2000) Proc Natl Acad Sci USA 97(7):3358-3363). Reference may also be made to the methods described in WO 97/08331 for increasing the homologous recombination in plants. A further increase in the efficacy of the recombination system might be achieved by the simultaneous expression of the RecA gene or other genes which increase the homologous recombination efficacy (Shalev G et al. (1999) Proc Natl Acad Sci USA 96(13):7398-402). The above-stated systems for promoting homologous recombination can also be advantageously employed in cases where the recombination construct is to be introduced in a site-directed fashion into the genome of a eukaryotic organism by means of homologous recombination.

Methods for Homologous Recombination and Targeted Mutation Using Optimized Endonucleases.

The current invention provides a method for homologous recombination of polynucleotides comprising:

a. providing a cell competent for homologous recombination,
b. providing a polynucleotide comprising a recombinant polynucleotide flanked by a sequence A and a sequence B,
c. providing a polynucleotide comprising sequences A' and B', which are sufficiently long and homologous to sequence A and sequence B, to allow for homologous recombination in said cell and
d. providing an optimized endonuclease or an expression cassette coding for an optimized endonuclease,
e. combining b), c) and d) in said cell and
f. detecting recombined polynucleotides of b) and c), or selecting for or growing cells comprising recombined polynucleotides of b) and c).

In one embodiment of the invention, step e) leads to deletion of a polynucleotide comprised in the polynucleotide provided in step c).

In one embodiment of the invention the deleted polynucleotide comprised in the polynucleotide provided in step c) codes for a marker gene or parts of a marker gene.

In one embodiment of the invention, the polynucleotide provided in step b) comprises at least one expression cassette.

In one embodiment of the invention, the polynucleotide provided in step b) comprises at least one expression cassette, leading to expression of a selection marker gene or a reporter gene.

In one embodiment of the invention, the polynucleotide provided in step b) comprises at least one expression cassette, leading to expression of a selection marker gene or a reporter gene and comprises at least one DNA recognition site or at least one chimeric recognition site.

A further embodiment of the invention provides a method for targeted mutation of polynucleotides comprising:
a. providing a cell comprising a polynucleotide comprising an I-SceI recognition site,
b. providing a optimized endonuclease, being able to cleave the chimeric recognition site of step a),
c. combining a) and b) in said cell and
d. detecting mutated polynucleotides, or selecting for growing cells comprising mutated polynucleotides.

The invention provides in another embodiment a method for homologous recombination as described above or a method for targeted mutation of polynucleotides as described above, comprising:

Combining the optimized endonuclease and the SceI recognition site via crossing of organisms, via transformation of cells or via a SecIV peptide fused to the optimized endonuclease and contacting the cell comprising the SceI recognition site with an organism expressing the optimized endonuclease and expressing a SecIV transport complex able to recognize the SecIV peptide fused to the chimeric endonuclease.

EXAMPLES

General Methods:

The chemical synthesis of oligonucleotides can be effected for example in the known manner using the phosphoamidite method (Voet, Voet, 2nd edition, Wiley Press New York, pages 896-897). The cloning steps carried out for the purposes of the present invention, such as, for example, restriction cleavages, agarose gel electrophoresis, purification of DNA fragments, the transfer of nucleic acids to nitrocellulose and nylon membranes, the linkage of DNA fragments, the transformation of E. coli cells, bacterial cultures, the propagation of phages and the sequence analysis of recombinant DNA are carried out as described by Sambrook et al. (1989) Cold Spring Harbor Laboratory Press; ISBN 0-87969-309-6. Recombinant DNA molecules were sequenced using an ALF Express laser fluorescence DNA sequencer (Pharmacia, Upsala [sic], Sweden) following the method of Sanger (Sanger et al., Proc. Natl. Acad. Sci. USA 74 (1977), 5463-5467).

Example 1

Constructs Harboring Sequence Specific DNA-Endonuclease Expression Cassettes for Expression in E. coli

Example 1a

Basic Construct

In this example we present the general outline of a vector, named "Construct I" suitable for transformation in E. coli. This general outline of the vector comprises an ampicillin resistance gene for selection, a replication origin for E. coli and the gene araC, which encodes an Arabinose inducible transcription regulator. SEQ ID NO: 7 shows a sequence stretch of "NNNNNNNNNN". This is meant to be a placeholder for genes encoding the different versions of the sequence specific DNA-endonuclease. The different genes can be expressed from the Arabinose inducible pBAD promoter (Guzman et al., J Bacteriol 177: 4121-4130(1995)), the sequences of the genes encoding the different nuclease versions are given in the following examples.

The control construct, in which the placeholder is replaced by the sequence of I-SceI (SEQ ID NO: 8), was called VC-SAH40-4.

Example 2

E. coli—Plasmids Encoding Stabilized Versions of the Nuclease

Different destablizing sequences could be identified in the aminoacid sequence of I-SceI.

Among them a weak PEST sequence at the C-terminus, which comprises amino acid residues 228 to 236 and a N-terminal sequence which shows similarity to a KEN motif (Pfleger and Kirschner, Genes and Dev. 14:655-665 (2000)). According to the N end rule, the second amino acid residue of I-SceI confers instability to the protein.

To test the effect of those sequences on the stability of the nuclease, different versions of I-SceI were generated by PCR, that lack amino acids from the N-terminus, 9 amino acids from the C-terminus or both. Those constructs were expressed from "Construct I", described in Example 1a). Therefore the placeholder was replaced by various sequences, encoding the versions of the nuclease (shown in SEQ ID NO: 2, 3, 5). The plasmids were called VC-SAH43-8 (C terminal shortened I-SceI) and VC-SAH42-13 (NLS-C terminal shortened I-SceI), VC-SAH44-32 (N terminal shortened I-SceI, SEQ ID NO: 21) and VC-SAH45-3 (N- and C-terminal shortened I-Sce, SEQ ID NO: 22)

According to the N end rule, all these constructs carry the stabilizing second amino acid residue G. To test the effect of the second amino acid on protein stability, also versions with the native, destabilizing residue of I-SceI are generated. The resulting plasmids were called VC-SAH105 and VC-SAH106.

Additional deletions of the C terminus were generated:

Single amino acid residues were successively removed from the C terminus. These variants are summarized in Table 3) and were tested for their activity in E. coli.

In addition potential PEST sequences were found in I-SceI and analyzed by introduction of single amino acid exchanges. These variants are summarized in Table 3) and were tested for their activity in E. coli.

TABLE 3

| vector name | nuclease variant |
| --- | --- |
| VC-SAH151-2 | NLS I-SceI -1 |
| VC-SAH152-6 | NLS I-SceI -2 |
| VC-SAH153-6 | NLS I-SceI -3 |
| VC-SAH154-1 | NLS I-SceI -4 |
| VC-SAH155-1 | NLS I-SceI -5 |
| VC-SAH156-3 | NLS I-SceI -6 |
| VC-SAH157-1 | NLS I-SceI -7 |
| VC-SAH158-2 | NLS I-SceI -8 |
| VC-SAH159-3 | NLS I-SceI -10 |
| VC-SAH160-1 | NLS I-SceI -11 |
| VC-SAH161-1 | NLS I-SceI -12 |
| VC-SAH162-2 | NLS I-SceI -13 |

TABLE 3-continued

| vector name | nuclease variant |
| --- | --- |
| VC-SAH163-1 | NLS I-SceI 1-218 |
| VC-SAH164-2 | NLS I-SceI 1-202 |
| VC-SAH165-3 | NLS I-SceI 1-187 |
| VC-SAH166-1 | NLS I-SceI 1-169 |
| VC-SAH167-1 | NLS I-SceI 1-155 |
| VC-SAH190-4 | I-SceI L74K |
| VC-SAH191-3 | I-SceI Y75H |
| VC-SAH192-3 | I-SceI Q77K |
| VC-SAH193-3 | I-SceI E130K |
| VC-SAH194-1 | I-SceI T134H |
| VC-SAH195-2 | I-SceI Y199H |
| VC-SAH196-2 | I-SceI M203K |
| VC-SAH197-2 | I-SceI Y205H |
| VC-SAH198-1 | I-SceI S230K |

Example 3

Cotransformation of DNA Endonuclease Encoding Constructs and Constructs Harbouring Nuclease Recognition Sequences in *E. coli*

Plasmids VC-SAH44-32, VC-SAH43-8, VC-SAH42-13, VC-SAH45-3 and VC-SAH40-4 (described in Example 2) were individually cotransformed with the target vector VC-SAH6-1 or the control vector VC-SAH7-1 in *E. coli*. The same is done with VC-SAH105 and VC-SAH106 and the vectors summarized in Table 3.

Example 4

Demonstration of the Endonuclease Activity in *E. coli*

The versions of I-SceI described in Example 2 were tested for their activity

Cotransformants which carry the combination of two plasmids, one encoding a nuclease or a and the other one harboring the nuclease target site were grown over night in LB with Ampicillin, Kanamycin and Glucose to repress the pBAD promoter. The cultures were diluted 1:100 and grown until they reached $OD_{600}$=0.5. The expression of the nuclease was induced by addition of Arabinose for 3 to 4 hours. The pBAD promoter is described to be dose dependent (Guzman 1995), therefore the culture was divided in different aliquots and protein expression was induced with Arabinose concentrations varying from 0.2% to 0.0002%. 5 µl of each aliquot were plated on LB solid media, supplemented with Ampicillin and Kanamycin. The plates were incubated over night at 37° C. and cell growth was analyzed semi quantitatively. Active nuclease fusions did cut the constructs, which harbor the target site. This led to the loss of Kanamycin resistance. Therefore, activity of the fusion protein was observed due to the lost ability of the cotransformants to grow on Kanamycin containing medium.

Results:

VC-SAH43-8 (C terminal shortened I-SceI) and VC-SAH42-13 (NLS-C terminal shortened I-SceI) were very active, they cut the target site even in the absence of the inducer Arabinose. Cell growth of these cotransformants was observed only in the presence of Glucose, which further represses the pBAD promoter. So in the cases of VC-SAH43-8 and VC-SAH42-13 the low amount of I-SceI protein produced due to the basal expression from the pBAD promoter was sufficient to cut the target plasmid.

The results are simplified and summarized in Table 4 ++ and + represent very strong and strong growth, which indicates no or little activity of the expressed nuclease towards the respective target site. − and −− represent reduced or no growth, which indicates high or very high activity of the nuclease towards the respective target site.

TABLE 4

I-SceI variants: *E. coli* growth assay indicates endonuclease activity against the respective target sites.

| nuclease variant | | VC-SAH6-1 (I-SceI site) | VC-SAH7-1 (control) |
| --- | --- | --- | --- |
| VC-SAH40-4 | I-SceI | + | ++ |
| VC-SAH43-8 | C term shortI-SceI (−9) | − | + |
| VC-SAH42-13 | NLS -C term short I-SceI (−9) | − | + |
| VC-SAH151-2 | NLS I-SceI -1 | − | ++ |
| VC-SAH152-6 | NLS I-SceI -2 | − | ++ |
| VC-SAH153-6 | NLS I-SceI -3 | − | ++ |
| VC-SAH154-1 | NLS I-SceI -4 | − | ++ |
| VC-SAH155-1 | NLS I-SceI -5 | − | ++ |
| VC-SAH156-3 | NLS I-SceI -6 | − | ++ |
| VC-SAH157-1 | NLS I-SceI -7 | − | + |
| VC-SAH158-2 | NLS I-SceI -8 | − | + |
| VC-SAH159-3 | NLS I-SceI -10 | − | + |
| VC-SAH160-1 | NLS I-SceI -11 | ++ | ++ |
| VC-SAH161-1 | NLS I-SceI -12 | ++ | ++ |
| VC-SAH162-2 | NLS I-SceI -13 | ++ | ++ |
| VC-SAH163-1 | NLS I-SceI 1-218 | ++ | ++ |
| VC-SAH164-2 | NLS I-SceI 1-202 | ++ | ++ |
| VC-SAH165-3 | NLS I-SceI 1-187 | ++ | ++ |
| VC-SAH166-1 | NLS I-SceI 1-169 | ++ | ++ |
| VC-SAH167-1 | NLS I-SceI 1-155 | ++ | ++ |

Example 5

Transformation of *S. cerevisiae*

*S. cerevisiae* cells are grown in 10 ml YEPS over night and then diluted 1:10. This culture is then grown until it reaches $OD_{600}$=0.5. The cells are pelleted and resuspended in 15 ml of sterile water twice, pelleted again and resuspended in 1 ml sterile water. This cell suspension is aliquoted a 100 µl and pelleted again. On ice, 240 µl 50% PEG4000, 36 µl 1M LiAc, 20 µl salmon sperm DNA (5 mg/ml) (5 minutes 100° C., then 10 minutes on ice) and 6 µg plasmid in 64 µl water are added. The suspension is incubated at 42° C. for 45 minutes and put on ice for 30 seconds. Cells are pelleted and resuspended in 500 µl water, of which 200 µl are plated on selective media lacking methionine. The plates are incubated at 30° C. for 3 to 4 days. Single colonies can be chosen for further analysis.

Example 6

Constructs Harbouring Stabilized Versions of the Nuclease for Expression in *S. cerevisiae*

The sequences described in Example 2 are cloned in the vector pGBT9-3H/B (Tirode et al 1997, J Biol Chem 272: 22995-22999) under the control of the MET25 promoter, which is repressed in the presence and active in the absence of methionine.

Example 7

Demonstration of the Endonuclease Stability in *S. cerevisiae*

Protein expression is induced by growing the transformants on medium lacking methionine.

Whole protein extract of the different transformants is generated and tested for the abundance and amount of I-SceI by Western blot analysis. Pulse chase experiments are done with the use of Cycloheximide and MG132, to determine the in vivo half life of the different versions.

Example 8

Constructs Encoding Stabilized Versions of the Nuclease for Expression in *A. thaliana*

Example 8a

Constructs for Demonstration of the Endonuclease Activity by Crossing Plants Expressing the Nuclease with Plants Carrying a T-DNA with the Respective Target Site All constructs showing activity in Table 4 are valuable for beeing tested, the following Examples will concentrate on the C terminal shortened version of I-SceI. Different plasmids were generated, where the placeholder of "Construct IV" (SEQ ID No: 13) is replaced by different sequences, encoding the C terminal shortened version of I-SceI, in combinations with or without stabilizing G as second amino acid residue, and with or without NLS. Most favourable are nuclease variants encoded by the constructs VC-SAH151-2, VC-SAH152-6, VC-SAH153-6, VC-SAH 154-1, VC-SAH 155-1, VC-SAH 156-3.

Example 8b

Constructs for Demonstration of the Endonuclease Activity by Transforming these Constructs in Plants already Carrying a T-DNA with the Respective Target Site In this example we present the general outline of a binary vector, named "Construct VI" (VC-SCB697)suitable for plant transformation. This general outline of the binary vector comprises a T-DNA with a nos-promoter::nptII::nos-terminator cassette, which enables selection on kanamycin, when integrated into the plant genome. SEQ ID NO: 23 (VC-SCB697) shows a sequence stretch of "NNNNNNNNNN". This is meant to be a placeholder for genes encoding versions of I-SceI.

Different plasmids were generated, where the placeholder is replaced by different constructs, consisting of the C terminal shortened version of I-SceI: VC-SAH124-3 (NLS-I-SceI C term shortened, G) (SEQ ID NO:5), VC-SAH125-2 (I-SceI C term shortened, G), (SEQ ID NO:3), VC-SAH122-7 (I-SceI, G) (SEQ ID NO:2) and VC-SAH123-3 (NLS-I-SceI, G), see Example 2 (As a control I-SceI without the stabilizing G as second amino acid residue was used: VC-SCB697-3). All constructs showing activity in Table 4 are valuable for testing, most favourable are nuclease variants encoded by the constructs VC-SAH151-2, VC-SAH152-6, VC-SAH153-6, VC-SAH 154-1, VC-SAH 155-1, VC-SAH 156-3.

Identical plasmids are generated without the stabilizing G as second amino acid residue.

Example 9

Transformation of Constructs Encoding Stabilized Versions of the Nuclease into *A. thaliana*

The plasmids described in Example 8b were transformed in *A. thaliana* lines carrying the T-DNA of VC-SCB583-40 (SEQ ID NO: 24).

The constructs described in Example 8a) are transformed in wild type plants.

Example 10

Monitoring Activity of the Stabilized Nucleases

Example 10a

By Crossing

The activity of the different versions of I-SceI is monitored by crossing sequence-specific DNA endonuclease expressing lines and lines harbouring constructs with recognition sequences. The recognition sequences are surrounded by a partial uidA (GUS) gene (called "GU") and another partial uidA gene (called "US"). The partially overlapping halves of the GUS gene (GU and US) are non-functional, but as a result of I-SceI activity on the target site a functional GUS gene will be restored by homologous intrachromosomal recombination (ICHR). This can be monitored by histochemical GUS staining Jefferson et al. (1987) EMBO J 6:3901-3907).

To visualize I-SceI activity, transgenic lines of Arabidopsis harbouring the T-DNA of the plasmids described in Example 9a) are crossed with lines of Arabidopsis harbouring the T-DNA of construct VC-SCB734-4. F1 seeds of the crosses are harvested. The seeds are surface sterilized and grown on medium A supplemented with the respective antibiotics and/or herbicides. 3-4 old seedlings are harvested and used for histochemical GUS staining. The amount of blue areas is an indicator of tissues/parts of tissues in which ICHR occurred in crosses and therefore for I-SceI activity.

Example 10b

By Supertransformation

The activity of the different versions of I-SceI was monitored by transforming lines harbouring constructs with recognition sequences with plasmids harbouring an expression cassette with different versions of the stabilized I-SceI. The recognition sequences are surrounded by a partial uidA (GUS) gene (called "GU") and another partial uidA gene (called "US"). The partially overlapping halves of the GUS gene (GU and US) are non-functional, but as a result of I-SceI activity on the target site a functional GUS gene will be restored by homologous intrachromosomal recombination (ICHR). This can be monitored by histochemical GUS staining Jefferson et al. (1987) EMBO J 6:3901-3907).

To visualize I-SceI activity, transgenic lines of Arabidopsis harbouring the T-DNA of construct pCB583-40 were transformed with plasmids described in Example 8b). F1 seeds were harvested, surface sterilized and grown on medium A supplemented with the respective antibiotics and/or herbicides. F1 plants were analyzed for single copy integration of the nuclease construct and selfed. F2 plants were grown on medium A without selection pressure. The T-DNA encoding the nuclease is also encoding dsRed. Due to segregation dsRed-free and therefore nuclease-free plants were selected under UV light. Seedlings with 4 leafes were harvested and used for histochemical GUS staining. Blue seedlings represent a homologous recombination event, that has occurred in the previous generation. For each construct 3 to 5 independend lines were analyzed, up to 96 seedlings were stained. The number of blue seedlings is an indicator for I-SceI activity.

Results:

In summary, I-SceI, I-SceI+G and NLS-I-SceI+G resulted between 30%-41% blue plants. Whereas the expression of the C terminal shortened versions encoded by VC-SAH124-3 and VC-SAH125-2 resulted in approximately 60% blue seedlings.

A positive GUS signal represents an ICHR event, due to I-SceI activity. The nuclease can also produce a cut, which might not be repaired by ICHR but by illegitimate recombination. This event will lead to the destruction of the I-SceI recognition seguence and to a non-functional GUS gene. In this case I-SceI activity can not be monitored by the blue staining. To further analyze the white seedlings obtained in this assay, a PCR reaction amplifying the halves of the GUS gene (GU and US) was performed. The amplicons were subjected to I-SceI digestion to detect the presence or absence of the target sequence. The absence of the target site represents I-SceI activity in the previous generation. In summary, the C terminal shortened I-SceI variants resulted in 1 out of 88 tested T2 plants with an intact I-SceI site. In contrast I-SceI encoded by the construct VC-SCB697-3 resulted in 14 out of 48 tested plants which still harbored an uncut I-SceI site.

The Cterminal shortened versions encoded by VC-SAH124-3 and VC-SAH125-2 gave rise to a T2 generation in which in almost all individuals show the result of I-SceI activity.

The invention claimed is:

1. An optimized endonuclease comprising an amino acid sequence having at least 92% sequence identity to the amino acid sequence of SEQ ID NO: 1 or 2, wherein said optimized endonuclease does not comprise the amino acid sequence TISSETFLK (SEQ NO: 31) at its C-terminus and has a higher capability to induce homologous recombination in comparison to an endonuclease having an identical amino acid sequence but comprising the amino acid sequence TISSETFLK (SEQ ID NO: 31) at its C-terminus.

2. The optimized endonuclease of claim 1, comprising the amino acid sequence of SEQ ID NO: 3 or 5.

3. The optimized endonuclease of claim 1, which is an engineered endonuclease.

4. The optimized endonuclease of claim 1, wherein the amino acid sequence TISSETFLK (SEQ ID NO: 31) at its C-terminus has been deleted by deleting 1, 2, 3, 4, 5, 6, 7, 8 or 9 amino acids of its C-terminus to create the optimized endonuclease.

5. The optimized endonuclease of claim 1, comprising an amino acid sequence having at least 92% amino acid sequence identity to the amino acid sequence of SEQ ID NO: 1 or 2, and comprising a mutation at a position corresponding to position 229 of the amino acid sequence of SEQ ID NO: 1.

6. The optimized endonuclease of claim 1 fused to:
  a) at least one zinc finer domain;
  b) at least one repeat unit derived from a transcription activator-like (TAL) effector; or
  c) at least one zinc finger domain and at least one repeat unit derived from a transcription activator-like (TAL) effector.

7. The optimized endonuclease of claim 1, further comprising a SecIII or SecIV secretion signal.

8. An isolated polynucleotide comprising a polynucleotide sequence which codes for the optimized endonuclease of claim 1.

9. The isolated polynucleotide of claim 8, wherein the polynucleotide sequence:
 a) is codon optimized,
 b) has a low content of RNA instability motifs,
 c) has a low content of codon repeats,
 d) has a low content of cryptic splice sites,
 e) has a low content of alternative start codons,
 f) has a low content of restriction sites,
 g) has a low content of RNA secondary structures, or
 h) has any combination of a), b), c), d), e), f), or g).

10. An expression cassette comprising the isolated polynucleotide of claim 8 in functional combination with a promoter and a terminator sequence.

11. A vector, host cell, or non-human organism comprising:
 a) an isolated polynucleotide comprising a polynucleotide sequence coding for the optimized endonuclease of claim 1;
 b) an expression cassette comprising the isolated polynucleotide of a) in functional combination with a promoter and a terminator sequence; or
 c) combination of a) and b).

12. The non-human organism of claim 11, wherein the non-human organism is a plant.

13. A method for homologous recombination of polynucleotides comprising:
 a) providing a cell competent for homologous recombination;
 b) providing a polynucleotide comprising a DNA recognition site of an optimized endonuclease flanked by a sequence A and a sequence B;
 c) providing a polynucleotide comprising sequences A' and B', which are sufficiently long and homologous to sequence A and sequence B, to allow for homologous recombination in said cell;
 d) providing the optimized endonuclease of claim 1, or an expression cassette comprising a polynucleotide encoding said optimized endonuclease in functional combination with a promoter and a terminator sequence;
 e) combining b), c) and d) in said cell; and
 f) detecting recombined polynucleotides of the polynucleotides of b) and c), or selecting for or growing cells comprising recombined polynucleotides of the polynucleotides of b) and c).

14. The method of claim 13, wherein upon homologous recombination a polynucleotide sequence in the competent cell of step a) is deleted from the genomes of the cells of step f).

15. A method for targeted. mutation of a polynucleotide comprising:
 a) providing a cell comprising a. polynucleotide comprising a DNA recognition site of the optimized endonuclease of claim 1;
 b) providing the optimized endonuclease of claim 1, or an expression cassette comprising a polynucleotide encoding said optimized endonuclease in functional combination. with a promoter and a terminator sequence, wherein said optimized endonuclease is able to cleave said DNA recognition site;
 c) combining the polynucleotide of a) and the optimized endonuclease of b) in said cell; and
 d) detecting a mutated polynucleotide, or selecting for or growing cells comprising a mutated polynucleotide.

16. The method of claim 13, wherein the optimized endonuclease and the DNA recognition site are combined in at least one cell via crossing of organisms, transformation, or transport mediated via a SecIII or SecIV peptide fused to the optimized endonuclease.

17. The optimized endonuclease of claim 1, wherein said optimized endonuclease comprises an amino acid sequence having at least 95% sequence identity to the amino acid sequence of SEQ ID NO: 1 or 2.

* * * * *

```
                        SEQUENCE LISTING

<160> NUMBER OF SEQ ID NOS: 45

<210> SEQ ID NO 1
<211> LENGTH: 235
<212> TYPE: PRT
<213> ORGANISM: Saccharomyces cerevisiae

<400> SEQUENCE: 1

Met Lys Asn Ile Lys Lys Asn Gln Val Met Asn Leu Gly Pro Asn Ser
1               5                   10                  15

Lys Leu Leu Lys Glu Tyr Lys Ser Gln Leu Ile Glu Leu Asn Ile Glu
                20                  25                  30

Gln Phe Glu Ala Gly Ile Gly Leu Ile Leu Gly Asp Ala Tyr Ile Arg
            35                  40                  45

Ser Arg Asp Glu Gly Lys Thr Tyr Cys Met Gln Phe Glu Trp Lys Asn
        50                  55                  60

Lys Ala Tyr Met Asp His Val Cys Leu Leu Tyr Asp Gln Trp Val Leu
65                  70                  75                  80

Ser Pro Pro His Lys Lys Glu Arg Val Asn His Leu Gly Asn Leu Val
                85                  90                  95

Ile Thr Trp Gly Ala Gln Thr Phe Lys His Gln Ala Phe Asn Lys Leu
            100                 105                 110

Ala Asn Leu Phe Ile Val Asn Asn Lys Lys Thr Ile Pro Asn Asn Leu
        115                 120                 125

Val Glu Asn Tyr Leu Thr Pro Met Ser Leu Ala Tyr Trp Phe Met Asp
    130                 135                 140

Asp Gly Gly Lys Trp Asp Tyr Asn Lys Asn Ser Thr Asn Lys Ser Ile
145                 150                 155                 160

Val Leu Asn Thr Gln Ser Phe Thr Phe Glu Glu Val Glu Tyr Leu Val
                165                 170                 175

Lys Gly Leu Arg Asn Lys Phe Gln Leu Asn Cys Tyr Val Lys Ile Asn
            180                 185                 190

Lys Asn Lys Pro Ile Ile Tyr Ile Asp Ser Met Ser Tyr Leu Ile Phe
        195                 200                 205

Tyr Asn Leu Ile Lys Pro Tyr Leu Ile Pro Gln Met Met Tyr Lys Leu
    210                 215                 220

Pro Asn Thr Ile Ser Ser Glu Thr Phe Leu Lys
225                 230                 235
```

```
<210> SEQ ID NO 2
<211> LENGTH: 236
<212> TYPE: PRT
<213> ORGANISM: Artificial Sequence
<220> FEATURE:
<223> OTHER INFORMATION: derived from I-SceI sequence

<400> SEQUENCE: 2

Met Gly Lys Asn Ile Lys Lys Asn Gln Val Met Asn Leu Gly Pro Asn
1               5                   10                  15

Ser Lys Leu Leu Lys Glu Tyr Lys Ser Gln Leu Ile Glu Leu Asn Ile
            20                  25                  30

Glu Gln Phe Glu Ala Gly Ile Gly Leu Ile Leu Gly Asp Ala Tyr Ile
        35                  40                  45

Arg Ser Arg Asp Glu Gly Lys Thr Tyr Cys Met Gln Phe Glu Trp Lys
    50                  55                  60

Asn Lys Ala Tyr Met Asp His Val Cys Leu Leu Tyr Asp Gln Trp Val
65                  70                  75                  80

Leu Ser Pro Pro His Lys Lys Glu Arg Val Asn His Leu Gly Asn Leu
                85                  90                  95

Val Ile Thr Trp Gly Ala Gln Thr Phe Lys His Gln Ala Phe Asn Lys
            100                 105                 110

Leu Ala Asn Leu Phe Ile Val Asn Asn Lys Lys Thr Ile Pro Asn Asn
        115                 120                 125

Leu Val Glu Asn Tyr Leu Thr Pro Met Ser Leu Ala Tyr Trp Phe Met
    130                 135                 140

Asp Asp Gly Gly Lys Trp Asp Tyr Asn Lys Asn Ser Thr Asn Lys Ser
145                 150                 155                 160

Ile Val Leu Asn Thr Gln Ser Phe Thr Phe Glu Glu Val Glu Tyr Leu
                165                 170                 175

Val Lys Gly Leu Arg Asn Lys Phe Gln Leu Asn Cys Tyr Val Lys Ile
            180                 185                 190

Asn Lys Asn Lys Pro Ile Ile Tyr Ile Asp Ser Met Ser Tyr Leu Ile
        195                 200                 205

Phe Tyr Asn Leu Ile Lys Pro Tyr Leu Ile Pro Gln Met Met Tyr Lys
    210                 215                 220

Leu Pro Asn Thr Ile Ser Ser Glu Thr Phe Leu Lys
225                 230                 235

<210> SEQ ID NO 3
<211> LENGTH: 227
<212> TYPE: PRT
<213> ORGANISM: Artificial Sequence
<220> FEATURE:
<223> OTHER INFORMATION: derived from I-SceI sequence

<400> SEQUENCE: 3

Met Gly Lys Asn Ile Lys Lys Asn Gln Val Met Asn Leu Gly Pro Asn
1               5                   10                  15

Ser Lys Leu Leu Lys Glu Tyr Lys Ser Gln Leu Ile Glu Leu Asn Ile
            20                  25                  30

Glu Gln Phe Glu Ala Gly Ile Gly Leu Ile Leu Gly Asp Ala Tyr Ile
        35                  40                  45

Arg Ser Arg Asp Glu Gly Lys Thr Tyr Cys Met Gln Phe Glu Trp Lys
    50                  55                  60

Asn Lys Ala Tyr Met Asp His Val Cys Leu Leu Tyr Asp Gln Trp Val
65                  70                  75                  80
```

-continued

```
Leu Ser Pro Pro His Lys Lys Glu Arg Val Asn His Leu Gly Asn Leu
                 85                  90                  95

Val Ile Thr Trp Gly Ala Gln Thr Phe Lys His Gln Ala Phe Asn Lys
            100                 105                 110

Leu Ala Asn Leu Phe Ile Val Asn Asn Lys Lys Thr Ile Pro Asn Asn
        115                 120                 125

Leu Val Glu Asn Tyr Leu Thr Pro Met Ser Leu Ala Tyr Trp Phe Met
    130                 135                 140

Asp Asp Gly Gly Lys Trp Asp Tyr Asn Lys Asn Ser Thr Asn Lys Ser
145                 150                 155                 160

Ile Val Leu Asn Thr Gln Ser Phe Thr Phe Glu Glu Val Glu Tyr Leu
                165                 170                 175

Val Lys Gly Leu Arg Asn Lys Phe Gln Leu Asn Cys Tyr Val Lys Ile
            180                 185                 190

Asn Lys Asn Lys Pro Ile Ile Tyr Ile Asp Ser Met Ser Tyr Leu Ile
        195                 200                 205

Phe Tyr Asn Leu Ile Lys Pro Tyr Leu Ile Pro Gln Met Met Tyr Lys
    210                 215                 220

Leu Pro Asn
225

<210> SEQ ID NO 4
<211> LENGTH: 7
<212> TYPE: PRT
<213> ORGANISM: SV40

<400> SEQUENCE: 4

Pro Lys Lys Lys Arg Lys Val
1               5

<210> SEQ ID NO 5
<211> LENGTH: 234
<212> TYPE: PRT
<213> ORGANISM: Artificial Sequence
<220> FEATURE:
<223> OTHER INFORMATION: derived from I-SceI sequence; S. cerevisiae

<400> SEQUENCE: 5

Met Gly Pro Lys Lys Lys Arg Lys Val Lys Asn Ile Lys Lys Asn Gln
1               5                   10                  15

Val Met Asn Leu Gly Pro Asn Ser Lys Leu Leu Lys Glu Tyr Lys Ser
            20                  25                  30

Gln Leu Ile Glu Leu Asn Ile Glu Gln Phe Glu Ala Gly Ile Gly Leu
        35                  40                  45

Ile Leu Gly Asp Ala Tyr Ile Arg Ser Arg Asp Glu Gly Lys Thr Tyr
    50                  55                  60

Cys Met Gln Phe Glu Trp Lys Asn Lys Ala Tyr Met Asp His Val Cys
65                  70                  75                  80

Leu Leu Tyr Asp Gln Trp Val Leu Ser Pro Pro His Lys Lys Glu Arg
                85                  90                  95

Val Asn His Leu Gly Asn Leu Val Ile Thr Trp Gly Ala Gln Thr Phe
            100                 105                 110

Lys His Gln Ala Phe Asn Lys Leu Ala Asn Leu Phe Ile Val Asn Asn
        115                 120                 125

Lys Lys Thr Ile Pro Asn Asn Leu Val Glu Asn Tyr Leu Thr Pro Met
    130                 135                 140

Ser Leu Ala Tyr Trp Phe Met Asp Asp Gly Gly Lys Trp Asp Tyr Asn
```

```
                145                 150                 155                 160
Lys Asn Ser Thr Asn Lys Ser Ile Val Leu Asn Thr Gln Ser Phe Thr
                    165                 170                 175

Phe Glu Glu Val Glu Tyr Leu Val Lys Gly Leu Arg Asn Lys Phe Gln
                180                 185                 190

Leu Asn Cys Tyr Val Lys Ile Asn Lys Asn Lys Pro Ile Ile Tyr Ile
            195                 200                 205

Asp Ser Met Ser Tyr Leu Ile Phe Tyr Asn Leu Ile Lys Pro Tyr Leu
        210                 215                 220

Ile Pro Gln Met Met Tyr Lys Leu Pro Asn
225                 230

<210> SEQ ID NO 6
<211> LENGTH: 18
<212> TYPE: DNA
<213> ORGANISM: Artificial Sequence
<220> FEATURE:
<223> OTHER INFORMATION: chimeric recognition site

<400> SEQUENCE: 6
tagggataac aggtaat                                                       18

<210> SEQ ID NO 7
<211> LENGTH: 4065
<212> TYPE: DNA
<213> ORGANISM: Artificial Sequence
<220> FEATURE:
<223> OTHER INFORMATION: plasmid
<220> FEATURE:
<221> NAME/KEY: misc_feature
<222> LOCATION: (3)..(12)
<223> OTHER INFORMATION: n is a, c, g, or t

<400> SEQUENCE: 7
ccnnnnnnnn nngaattcga agcttgggcc cgaacaaaaa ctcatctcag aagaggatct       60
gaatagcgcc gtcgaccatc atcatcatca tcattgagtt taaacggtct ccagcttggc      120
tgttttggcg gatgagagaa gattttcagc ctgatacaga ttaaatcaga acgcagaagc      180
ggtctgataa aacagaattt gcctggcggc agtagcgcgg tggtcccacc tgaccccatg      240
ccgaactcag aagtgaaacg ccgtagcgcc gatggtagtg tggggtctcc ccatgcgaga      300
gtagggaact gccaggcatc aaataaaacg aaaggctcag tcgaaagact gggcctttcg      360
ttttatctgt tgtttgtcgg tgaacgctct cctgagtagg acaaatccgc cgggagcgga      420
tttgaacgtt gcgaagcaac ggcccggagg gtggcgggca ggacgcccgc cataaactgc      480
caggcatcaa attaagcaga aggccatcct gacggatggc ctttttgcgt ttctacaaac      540
tcttttgttt attttctaa atacattcaa atatgtatcc gctcatgaga caataaccct      600
gataaatgct tcaataatat tgaaaaagga agagtatgag tattcaacat ttccgtgtcg      660
cccttattcc cttttttgcg gcattttgcc ttcctgtttt tgctcaccca gaaacgctgg      720
tgaaagtaaa agatgctgaa gatcagttgg gtgcacgagt gggttacatc gaactggatc      780
tcaacagcgg taagatcctt gagagttttc gccccgaaga acgttttcca atgatgagca      840
cttttaaagt tctgctatgt ggcgcggtat tatcccgtgt tgacgccggg caagagcaac      900
tcggtcgccg catacactat tctcagaatg acttggttga gtactcacca gtcacagaaa      960
agcatcttac ggatggcatg acagtaagag aattatgcag tgctgccata accatgagtg     1020
ataacactgc ggccaactta cttctgacaa cgatcggagg accgaaggag ctaaccgctt     1080
```

-continued

```
ttttgcacaa catgggggat catgtaactc gccttgatcg ttgggaaccg gagctgaatg      1140
aagccatacc aaacgacgag cgtgacacca cgatgcctgt agcaatggca caacgttgc      1200 gcaaactatt aactggcgaa ctacttactc tagcttcccg gcaacaatta atagactgga     1260
tggaggcgga taaagttgca ggaccacttc tgcgctcggc ccttccggct ggctggttta     1320
ttgctgataa atctggagcc ggtgagcgtg gtctcgcgg tatcattgca gcactggggc      1380
cagatggtaa gccctcccgt atcgtagtta tctacacgac ggggagtcag gcaactatgg     1440
atgaacgaaa tagacagatc gctgagatag gtgcctcact gattaagcat tggtaactgt     1500
cagaccaagt ttactcatat atactttaga ttgatttaaa acttcatttt taatttaaaa     1560
ggatctaggt gaagatcctt tttgataatc tcatgaccaa aatcccttaa cgtgagtttt     1620
cgttccactg agcgtcagac cccgtagaaa agatcaaagg atcttcttga gatccttttt     1680
ttctgcgcgt aatctgctgc ttgcaaacaa aaaaaccacc gctaccagcg gtggtttgtt     1740
tgccggatca agagctacca actcttttc cgaaggtaac tggcttcagc agagcgcaga     1800
taccaaatac tgtccttcta gtgtagccgt agttaggcca ccacttcaag aactctgtag     1860
caccgcctac atacctcgct ctgctaatcc tgttaccagt ggctgctgcc agtggcgata     1920
agtcgtgtct taccgggttg gactcaagac gatagttacc ggataaggcg cagcggtcgg     1980
gctgaacggg gggttcgtgc acacagccca gcttggagcg aacgacctac accgaactga     2040
gatacctaca gcgtgagcta tgagaaagcg ccacgcttcc cgaagggaga aaggcggaca     2100
ggtatccggt aagcggcagg gtcggaacag gagagcgcac gagggagctt ccaggggggaa    2160 acgcctggta tctttatagt cctgtcgggt ttcgccacct ctgacttgag cgtcgatttt     2220
tgtgatgctc gtcagggggg cggagcctat ggaaaaacgc cagcaacgcg gcctttttac     2280
ggttcctggc cttttgctgg ccttttgctc acatgttctt tcctgcgtta tcccctgatt     2340
ctgtggataa ccgtattacc gcctttgagt gagctgatac cgctcgccgc agccgaacga     2400
ccgagcgcag cgagtcagtg agcgaggaag cggaagagcg cctgatgcgg tattttctcc     2460
ttacgcatct gtgcggtatt tcacaccgca tatggtgcac tctcagtaca atctgctctg     2520
atgccgcata gttaagccag tatacactcc gctatcgcta cgtgactggg tcatggctgc     2580
gccccgacac ccgccaacac ccgctgacgc gccctgacgg gcttgtctgc tcccggcatc     2640
cgcttacaga caagctgtga ccgtctccgg gagctgcatg tgtcagaggt tttcaccgtc     2700
atcaccgaaa cgcgcgaggc agcagatcaa ttcgcgcgcg aaggcgaagc ggcatgcata     2760
atgtgcctgt caaatggacg aagcagggat tctgcaaacc ctatgctact ccgtcaagcc     2820
gtcaattgtc tgattcgtta ccaattatga caacttgacg gctacatcat tcacttttc      2880 ttcacaaccg gcacggaact cgctcgggct ggccccggtg catttttaa atacccgcga      2940 gaaatagagt tgatcgtcaa aaccaacatt gcgaccgacg gtggcgatag gcatccgggt     3000
ggtgctcaaa agcagcttcg cctggctgat acgttggtcc tcgcgccagc ttaagacgct     3060
aatccctaac tgctggcgga aaagatgtga cagacgcgac ggcgacaagc aaacatgctg     3120
tgcgacgctg gcgatatcaa aattgctgtc tgccaggtga tcgctgatgt actgacaagc     3180
ctcgcgtacc cgattatcca tcggtggatg gagcgactcg ttaatcgctt ccatcgcccg     3240
cagtaacaat tgctcaagca gatttatcgc cagcagctcc gaatagcgcc cttcccctttg    3300 cccggcgtta atgatttgcc caaacaggtc gctgaaatgc ggctggtgcg cttcatccgg     3360
gcgaaagaac cccgtattgg caaatattga cggccagtta agccattcat gccagtaggc     3420
gcgcggacga aagtaaaccc actggtgata ccattcgcga gcctccggat gacgaccgta     3480
```

```
gtgatgaatc tctcctggcg ggaacagcaa aatatcaccc ggtcggcaaa caaattctcg    3540
tccctgattt ttcaccaccc cctgaccgcg aatggtgaga ttgagaatat aacctttcat    3600
tcccagcggt cggtcgataa aaaaatcgag ataaccgttg gcctcaatcg gcgttaaacc    3660
cgccaccaga tgggcattaa acgagtatcc cggcagcagg ggatcatttt gcgcttcagc    3720 catactttc atactcccgc cattcagaga agaaaccaat tgtccatatt gcatcagaca     3780
ttgccgtcac tgcgtctttt actggctctt ctcgctaacc aaaccggtaa ccccgcttat    3840
taaaagcatt ctgtaacaaa gcgggaccaa agccatgaca aaaacgcgta acaaaagtgt    3900
ctataatcac ggcagaaaag tccacattga ttatttgcac ggcgtcacac tttgctatgc    3960
catagcattt ttatccataa gattagcgga tcctacctga cgcttttat cgcaactctc     4020 tactgtttct ccatacccgt ttttgggct aacaggagga attaa                    4065

<210> SEQ ID NO 8
<211> LENGTH: 711
<212> TYPE: DNA
<213> ORGANISM: Artificial Sequence
<220> FEATURE:
<223> OTHER INFORMATION: Insert of VC-SAH40-4

<400> SEQUENCE: 8
atgggtaaga acattaagaa gaaccaggtg atgaacctgg ccctaactc taagctgctt      60 aaggaataca agtctcagct gattgagctg aacattgagc agttcgaggc tggcataggc    120
ctgattctgg gcgatgctta cattaggtct agggatgagg gcaagaccta ctgcatgcag    180
ttcgagtgga agaacaaggc ttacatggat cacgtgtgcc tgctgtacga tcagtgggtg    240
ctgtctcctc ctcacaagaa ggagagggtg aaccacttgg gaaacctggt gattaccctgg    300 ggcgctcaaa ccttcaagca ccaggctttc aacaagctgg ctaacctgtt cattgtgaac    360
aacaagaaga ccattcctaa caacctggtg gagaactacc tgaccccat gtctctggct    420 tactggttca tggatgatgg cggcaagtgg gattacaaca agaactctac caacaagtct    480
attgtgctga acacccagtc tttcaccttc gaggagtgg aatacctggt gaagggcctg    540
aggaacaagt tccagctgaa ctgctacgtg aagattaaca agaacaagcc tattatttac    600
attgattcta tgtcttacct gattttctac aacctgatta agccttacct gattcctcag    660
atgatgtaca agctgcctaa caccatctct tctgagacct tcctgaagtg a            711

<210> SEQ ID NO 9
<211> LENGTH: 4905
<212> TYPE: DNA
<213> ORGANISM: Artificial Sequence
<220> FEATURE:
<223> OTHER INFORMATION: Construct II
<220> FEATURE:
<221> NAME/KEY: misc_feature
<222> LOCATION: (1218)..(1227)
<223> OTHER INFORMATION: n is a, c, g, or t

<400> SEQUENCE: 9
agcgctggca gtccttgcca ttgccgggat cggggcagta acgggatggg cgatcagccc      60
gagcgcgacg cccggaagca ttgacgtgcc gcaggtgctg gcatcgacat tcagcgacca    120
ggtgccgggc agtgagggcg gcggcctggg tggcggcctg cccttcactt cggccgtcgg    180
ggcattcacg gacttcatgg cggggccggc aattttacc ttgggcattc ttggcatagt    240
ggtcgcgggt gccgtgctcg tgttcggggg tgcgataaac ccagcgaacc atttgaggtg    300
```

```
ataggtaaga ttataccgag gtatgaaaac gagaattgga cctttacaga attactctat    360
gaagcgccat atttaaaaag ctaccaagac gaagaggatg aagaggatga ggaggcagat    420
tgccttgaat atattgacaa tactgataag ataatatatc ttttatatag aagatatcgc    480
cgtatgtaag gatttcaggg ggcaaggcat aggcagcgcg cttatcaata tatctataga    540
atgggcaaag cataaaaact tgcatggact aatgcttgaa acccaggaca ataaccttat    600
agcttgtaaa ttctatcata attgggtaat gactccaact tattgatagt gttttatgtt    660
cagataatgc ccgatgactt tgtcatgcag ctccaccgat tttgagaacg acagcgactt    720
ccgtcccagc cgtgccaggt gctgcctcag attcaggtta tgccgctcaa ttcgctgcgt    780
atatcgcttg ctgattacgt gcagctttcc cttcaggcgg gattcataca gcggccagcc    840
atccgtcatc catatcacca cgtcaaaggg tgacagcagg ctcataagac gccccagcgt    900
cgccatagtg cgttcaccga atacgtgcgc aacaaccgtc ttccggagac tgtcatacgc    960
gtaaaacagc cagcgctggc gcgatttagc cccgacatag ccccactgtt cgtccatttc   1020
cgcgcagacg atgacgtcac tgcccggctg tatgcgcgag gttaccgact gcggcctgag   1080
ttttttaagt gacgtaaaat cgtgttgagg ccaacgccca taatgcgggc tgttgcccgg   1140
catccaacgc cattcatggc catatcaatg attttctggt gcgtaccggg ttgagaagcg   1200
gtgtaagtga actgcagnnn nnnnnnnaag cttgactctc ttaagggagc gtcgagtacg   1260
cgcccgggga gcccaagggc acgccctggc acccgaagct ctagtatcaa atttggcaca   1320
aaaagcaaaa ttaaaatact gataattgcc aacacaatta acatctcaat caaggtaaat   1380
gcttttttgct ttttttgcca aagctatctt ccgtgatcag agctccagct tttgttccct   1440
ttagtgaggg ttaattgcgc gcttggcgta atcatggtca tagctgtttc ctgtgtgaaa   1500
ttgttatccg ctcacaattc cacacaacat acgagccgga agcataaagt gtaaagcctg   1560
gggtgcctaa tgagtgagct aactcacatt aattgcgttg cgctcactgc ccgctttcca   1620
gtcgggaaac ctgtcgtgcc agctgataga cacagaagcc actggagcac tcaaaaaca    1680
ccatcataca ctaaatcagt aagttggcag catcacccat aattgtggtt tcaaaatcgg   1740
ctccgtcgat actatgttat acgccaactt gaaaacaac tttgaaaaag ctgttttctg    1800
gtatttaagg ttttagaatg caaggaacag tgaattggag ttcgtcttgt tataattagc   1860
ttcttggggt atctttaaat actgtagaaa agaggaagga aataataaat ggctaaaatg   1920
agaatatcac cggaattgaa aaaactgatc gaaaaatacc gctgcgtaaa agatacggaa   1980
ggaatgtctc ctgctaaggt atataagctg gtgggagaaa atgaaaacct atatttaaaa   2040
atgacggaca gccggtataa agggaccacc tatgatgtgg aacgggaaaa ggacatgatg   2100
ctatggctgg aaggaaagct gcctgttcca aaggtcctgc actttgaacg gcatgatggc   2160
tggagcaatc tgctcatgag tgaggccgat ggcgtccttt gctcggaaga gtatgaagat   2220
gaacaaagcc ctgaaaagat tatcgagctg tatgcggagt gcatcaggct ctttcactcc   2280
atcgacatat cggattgtcc ctatacgaat agcttagaca gccgcttagc cgaattggat   2340
tacttactga ataacgatct ggccgatgtg gattgcgaaa actgggaaga agacactcca   2400
tttaagatc cgcgcgagct gtatgatttt ttaaagacgg aaaagcccga agaggaactt    2460
gtcttttccc acggcgacct gggagacagc aacatctttg tgaaagatgg caaagtaagt   2520
ggctttattg atcttgggag aagcggcagg gcggacaagt ggtatgacat tgccttctgc   2580
gtccggtcga tcagggagga tatcgggaa gaacagtatg tcgagctatt ttttgactta   2640
ctggggatca agcctgattg ggagaaaata aaatattata ttttactgga tgaattgttt   2700
```

```
tagtacctag atgtggcgca acgatgccgg cgacaagcag gagcgcaccg acttcttccg   2760
catcaagtgt tttggctctc aggccgaggc ccacggcaag tatttgggca aggggtcgct   2820
ggtattcgtg cagggcaaga ttcggaatac caagtacgag aaggacggcc agacggtcta   2880
cgggaccgac ttcattgccg ataaggtgga ttatctggac accaaggcac caggcgggtc   2940
aaatcaggaa taagggcaca ttgccccggc gtgagtcggg gcaatcccgc aaggagggtg   3000
aatgaatcgg acgtttgacc ggaaggcata caggcaagaa ctgatcgacg cggggttttc   3060
cgccgaggat gccgaaacca tcgcaagccg caccgtcatg cgtgcgcccc gcgaaacctt   3120
ccagtccgtc ggctcgatgg tccagcaagc tacggccaag atcgagcgcg acagcgtgca   3180
actggctccc cctgccctgc ccgcgccatc ggccgccgtg gagcgttcgc gtcgtctcga   3240
acaggaggcg gcaggtttgg cgaagtcgat gaccatcgac acgcgaggaa ctatgacgac   3300
caagaagcga aaaccgccg gcgaggacct ggcaaaacag gtcagcgagg ccaagcaggc   3360
cgcgttgctg aaacacacga agcagcagat caaggaaatg cagctttcct tgttcgatat   3420
tgcgccgtgg ccggacacga tgcgagcgat gccaaacgac acggcccgct ctgccctgtt   3480
caccacgcgc aacaagaaaa tcccgcgcga ggcgctgcaa aacaaggtca ttttccacgt   3540
caacaaggac gtgaagatca cctacaccgg cgtcgagctg cgggccgacg atgacgaact   3600
ggtgtggcag caggtgttgg agtacgcgaa gcgcacccct atcggcgagc cgatcacctt   3660
cacgttctac gagctttgcc aggacctggg ctggtcgatc aatggccggt attacacgaa   3720
ggccgaggaa tgcctgtcgc gcctacaggc gacggcgatg ggcttcacgt ccgaccgcgt   3780
tgggcacctg gaatcggtgt cgctgctgca ccgcttccgc gtcctggacc gtggcaagaa   3840
aacgtcccgt tgccaggtcc tgatcgacga ggaaatcgtc gtgctgtttg ctggcgacca   3900
ctacacgaaa ttcatatggg agaagtaccg caagctgtcg ccgacggccc gacggatgtt   3960
cgactatttc agctcgcacc gggagccgta cccgctcaag ctggaaacct tccgcctcat   4020
gtgcggatcg gattccaccc gcgtgaagaa gtggcgcgag caggtcggcg aagcctgcga   4080
agagttgcga ggcagcggcc tggtggaaca cgcctgggtc aatgatgacc tggtgcattg   4140
caaacgctag ggccttgtgg ggtcagttcc ggctgggggt tcagcagcca gcgctttact   4200
ctagtgacgc tcaccgggct ggttgccctc gccgctgggc tggcggccgt ctatggccct   4260
gcaaacgcgc cagaaacgcc gtcgaagccg tgtgcgagac accgcggccg ccggcgttgt   4320
ggatacctcg cggaaaactt ggccctcact gacagatgag gggcggacgt tgacacttga   4380
ggggccgact caccoggcgc ggcgttgaca gatgagggggc aggctcgatt tcggccggcg   4440
acgtggagct ggccagcctc gcaaatcggc gaaaacgcct gattttacgc gagtttccca   4500
cagatgatgt ggacaagcct ggggataagt gccctgcgt attgacactt gaggggcgcg   4560
actactgaca gatgagggggc gcgatccttg acacttgagg ggcagagtgc tgacagatga   4620
ggggcgcacc tattgacatt tgaggggctg tccacaggca gaaaatccag catttgcaag   4680
ggtttccgcc cgtttttcgg ccaccgctaa cctgtctttt aacctgcttt taaaccaata   4740
tttataaacc ttgttttaa ccagggctgc gccctgtgcg cgtgaccgcg cacgccgaag   4800 ggggggtgccc cccttctcg aaccctcccg gcccgctaac gcgggcctcc catccccca   4860 ggggctgcgc ccctcggccg cgaacggcct caccccaaaa atggc                  4905
```

<210> SEQ ID NO 10
<211> LENGTH: 260
<212> TYPE: DNA

```
<213> ORGANISM: Artificial Sequence
<220> FEATURE:
<223> OTHER INFORMATION: Insert of VC-SAH6-1

<400> SEQUENCE: 10
ttgccatgtt ttacggcagt gagagcagag atagcgctga tgtccggcgg tgcttttgcc      60
gttacgcacc accccgtcag tagctgaaca ggagggacag ctggcgaaag ggggatgtgc     120
tgcaaggcga ttaagttggg taacgccagg gttttcccag tcacgacgtt gtaaaacgac     180
ggccagtgag cgcgcgtaat acgactcact ataggggcgaa ttgggtactc gagtacgcta    240
gggataacag ggtaatatag                                                  260

<210> SEQ ID NO 11
<211> LENGTH: 4580
<212> TYPE: DNA
<213> ORGANISM: Artificial Sequence
<220> FEATURE:
<223> OTHER INFORMATION: VC-SAH7-1

<400> SEQUENCE: 11
ctagtgacgc tcaccgggct ggttgccctc gccgctgggc tggcggccgt ctatggccct      60
gcaaacgcgc cagaaacgcc gtcgaagccg tgtgcgagac accgcggccg ccggcgttgt     120
ggatacctcg cggaaaactt ggccctcact gacagatgag gggcggacgt tgacacttga     180
ggggccgact caccggcgc ggcgttgaca atgaggggc aggctcgatt tcggccggcg       240
acgtggagct ggccagcctc gcaaatcggc gaaaacgcct gattttacgc gagtttccca     300
cagatgatgt ggacaagcct ggggataagt gccctgcgt attgacactt gaggggcgcg     360
actactgaca gatgagggc gcgatccttg acacttgagg ggcagagtgc tgacagatga      420
ggggcgcacc tattgacatt tgaggggctg tccacaggca gaaatccag catttgcaag      480 ggtttccgcc cgttttcgg ccaccgctaa cctgtctttt aacctgcttt taaaccaata     540
tttataaacc ttgtttttaa ccagggctgc gccctgtgcg cgtgaccgcg cacgccgaag    600
gggggtgccc ccccttctcg aaccctcccg gcccgctaac gcgggcctcc catcccccca     660
ggggctgcgc ccctcggccg cgaacggcct caccccaaaa atggcagcgc tggcagtcct     720
tgccattgcc gggatcgggg cagtaacggg atgggcgatc agcccgagcg cgacgcccgg    780
aagcattgac gtgccgcagg tgctggcatc gacattcagc gaccaggtgc cgggcagtga    840
gggcggcggc ctgggtggcg gcctgccctt cacttcggcc gtcggggcat tcacggactt    900
catggcgggg ccggcaattt ttaccttggg cattcttggc atagtggtcg cgggtgccgt    960
gctcgtgttc gggggtgcga taaacccagc gaaccatttg aggtgatagg taagattata   1020
ccgaggtatg aaaacgagaa ttggaccttt acagaattac tctatgaagc gccatattta   1080
aaaagctacc aagacgaaga ggatgaagag gatgaggagg cagattgcct tgaatatatt   1140
gacaatactg ataagataat atatctttta tatagaagat atcgccgtat gtaaggattt   1200 caggggggcaa ggcataggca gcgcgcttat caatatatct atagaatggg caaagcataa   1260
aaacttgcat ggactaatgc ttgaaaccca ggacaataac cttatagctt gtaaattcta   1320
tcataattgg gtaatgactc caacttattg atagtgtttt atgttcagat aatgcccgat   1380
gactttgtca tgcagctcca ccgattttga gaacgacagc gacttccgtc ccagccgtgc   1440
caggtgctgc ctcagattca ggttatgccg ctcaattcgc tgcgtatatc gcttgctgat   1500
tacgtgcagc tttcccttca ggcgggattc atacagcggc cagccatccg tcatccatat   1560
caccacgtca aagggtgaca gcaggctcat aagacgcccc agcgtcgcca tagtgcgttc   1620
```

```
accgaatacg tgcgcaacaa ccgtcttccg gagactgtca tacgcgtaaa acagccagcg   1680
ctggcgcgat ttagccccga catagcccca ctgttcgtcc atttccgcgc agacgatgac   1740
gtcactgccc ggctgtatgc gcgaggttac cgactgcggc ctgagttttt taagtgacgt   1800
aaaatcgtgt tgaggccaac gcccataatg cgggctgttg cccggcatcc aacgccattc   1860
atggccatat caatgatttt ctggtgcgta ccgggttgag aagcggtgta agtgaactgc   1920
agttgccatg ttttacggca gtgagagcag agatagcgct gatgtccggc ggtgcttttg   1980
ccgttacgca ccaccccgtc agtagctgaa caggagggac agctgataga cacagaagcc   2040
actggagcac ctcaaaaaca ccatcataca ctaaatcagt aagttggcag catcacccat   2100
aattgtggtt tcaaaatcgg ctccgtcgat actatgttat acgccaactt tgaaaacaac   2160
tttgaaaaag ctgttttctg gtatttaagg ttttagaatg caaggaacag tgaattggag   2220
ttcgtcttgt tataattagc ttcttggggt atctttaaat actgtagaaa agaggaagga   2280
aataataaat ggctaaaatg agaatatcac cggaattgaa aaaactgatc gaaaaatacc   2340
gctgcgtaaa agatacggaa ggaatgtctc ctgctaaggt atataagctg gtgggagaaa   2400
atgaaaacct atatttaaaa atgacggaca gccggtataa agggaccacc tatgatgtgg   2460
aacgggaaaa ggacatgatg ctatggctgg aaggaaagct gcctgttcca aaggtcctgc   2520
actttgaacg gcatgatggc tggagcaatc tgctcatgag tgaggccgat ggcgtccttt   2580
gctcggaaga gtatgaagat gaacaaagcc ctgaaaagat tatcgagctg tatgcggagt   2640
gcatcaggct ctttcactcc atcgacatat cggattgtcc ctatacgaat agcttagaca   2700
gccgcttagc cgaattggat tacttactga ataacgatct ggccgatgtg gattgcgaaa   2760
actgggaaga agacactcca tttaaagatc gcgcgagct gtatgatttt ttaaagacgg   2820
aaaagcccga agaggaactt gtcttttccc acggcgacct gggagacagc aacatctttg   2880
tgaaagatgg caaagtaagt ggctttattg atcttgggag aagcggcagg cggacaagt   2940
ggtatgacat tgccttctgc gtccggtcga tcagggagga tatcggggaa gaacagtatg   3000
tcgagctatt ttttgactta ctggggatca agcctgattg ggagaaaata aatattata   3060
ttttactgga tgaattgttt tagtacctag atgtggcgca acgatgccgg cgacaagcag   3120
gagcgcaccg acttcttccg catcaagtgt tttggctctc aggccgaggc ccacggcaag   3180
tatttgggca aggggtcgct ggtattcgtg cagggcaaga ttcggaatac caagtacgag   3240
aaggacggcc agacggtcta cggaccgac ttcattgccg ataaggtgga ttatctggac   3300
accaaggcac caggcgggtc aaatcaggaa taagggcaca ttgccccggc gtgagtcggg   3360
gcaatcccgc aaggagggtg aatgaatcgg acgtttgacc ggaaggcata caggcaagaa   3420
ctgatcgacg cggggttttc cgccgaggat gccgaaacca tcgcaagccg caccgtcatg   3480
cgtgcgcccc gcgaaaacctt ccagtccgtc ggctcgatgg tccagcaagc tacggccaag   3540
atcgagcgcg acagcgtgca actggctccc cctgccctgc ccgcgccatc ggccgccgtg   3600
gagcgttcgc gtcgtctcga acaggaggcg gcaggtttgg cgaagtcgat gaccatcgac   3660
acgcgaggaa ctatgacgac caagaagcga aaaccgccg gcgaggacct ggcaaaacag   3720
gtcagcgagg ccaagcaggc gcgcgttgctg aaacacacga agcagcagat caaggaaatg   3780
cagcttttcct tgttcgatat tgcgccgtgg ccggacacga tgcgagcgat gccaaacgac   3840
acggcccgct ctgccctgtt caccacgcgc aacaagaaaa tccgcgcgcga ggcgctgcaa   3900
aacaaggtca ttttccacgt caacaaggac gtgaagatca cctacaccgg cgtcgagctg   3960
```

| | |
|---|---|
| cgggccgacg atgacgaact ggtgtggcag caggtgttgg agtacgcgaa gcgcacccct | 4020 |
| atcggcgagc cgatcacctt cacgttctac gagctttgcc aggacctggg ctggtcgatc | 4080 |
| aatggccggt attacacgaa ggccgaggaa tgcctgtcgc gcctacaggc gacggcgatg | 4140 |
| ggcttcacgt ccgaccgcgt tgggcacctg gaatcggtgt cgctgctgca ccgcttccgc | 4200 |
| gtcctggacc gtggcaagaa aacgtcccgt tgccaggtcc tgatcgacga ggaaatcgtc | 4260 |
| gtgctgtttg ctggcgacca ctacacgaaa ttcatatggg agaagtaccg caagctgtcg | 4320 |
| ccgacggccc gacggatgtt cgactatttc agctcgcacc gggagccgta cccgctcaag | 4380 |
| ctggaaacct tccgcctcat gtgcggatcg gattccaccc gcgtgaagaa gtggcgcgag | 4440 |
| caggtcggcg aagcctgcga agagttgcga ggcagcggcc tggtggaaca cgcctgggtc | 4500 |
| aatgatgacc tggtgcattg caaacgctag ggccttgtgg ggtcagttcc ggctgggggt | 4560 |
| tcagcagcca gcgctttact | 4580 |

<210> SEQ ID NO 12
<211> LENGTH: 5221
<212> TYPE: DNA
<213> ORGANISM: Artificial Sequence
<220> FEATURE:
<223> OTHER INFORMATION: Construct III
<220> FEATURE:
<221> NAME/KEY: misc_feature
<222> LOCATION: (1557)..(1566)
<223> OTHER INFORMATION: n is a, c, g, or t

<400> SEQUENCE: 12

| | |
|---|---|
| agcgctggca gtccttgcca ttgccgggat cggggcagta acgggatggg cgatcagccc | 60 |
| gagcgcgacg cccggaagca ttgacgtgcc gcaggtgctg gcatcgacat tcagcgacca | 120 |
| ggtgccgggc agtgagggcg gcggcctggg tggcggcctg cccttcactt cggccgtcgg | 180 |
| ggcattcacg gacttcatgg cggggccggc aattttttacc ttgggcattc ttggcatagt | 240 |
| ggtcgcgggt gccgtgctcg tgttcggggg tgcgataaac ccagcgaacc atttgaggtg | 300 |
| ataggtaaga ttataccgag gtatgaaaac gagaattgga cctttacaga attactctat | 360 |
| gaagcgccat atttaaaaag ctaccaagac gaagaggatg aagaggatga ggaggcagat | 420 |
| tgccttgaat atattgacaa tactgataag ataatatatc ttttatatag aagatatcgc | 480 |
| cgtatgtaag gatttcaggg ggcaaggcat aggcagcgcg cttatcaata tatctataga | 540 |
| atgggcaaag cataaaaact tgcatggact aatgcttgaa acccaggaca ataaccttat | 600 |
| agcttgtaaa ttctatcata attgggtaat gactccaact tattgatagt gttttatgtt | 660 |
| cagataatgc ccgatgactt tgtcatgcag ctccaccgat tttgagaacg acagcgactt | 720 |
| ccgtcccagc cgtgccaggt gctgcctcag attcaggtta tgccgctcaa ttcgctgcgt | 780 |
| atatcgcttg ctgattacgt gcagctttcc cttcaggcgg gattcataca gcggccagcc | 840 |
| atccgtcatc catatcacca cgtcaaaggg tgacagcagg ctcataagac gccccagcgt | 900 |
| cgccatagtg cgttcaccga atacgtgcgc aacaaccgtc ttccggagac tgtcatacgc | 960 |
| gtggttacag tcttgcgcga catgcgtcac cacggtgata tcgtccaccc aggtgttcgg | 1020 |
| cgtggtgtag agcattacgc tgcgatggat tccggcatag ttaaagaaat catggaagta | 1080 |
| agactgcttt ttcttgccgt tttcgtcggt aatcaccatt cccggcggga tagtctgcca | 1140 |
| gttcagttcg ttgttcacac aaacggtgat acgtacactt ttcccggcaa taacatacgg | 1200 |
| cgtgacatcg gcttcaaatg gcgtatagcc gccctgatgc tccatcactt cctgattatt | 1260 |
| gacccacact ttgccgtaat gagtgaccgc atcgaaacgc agcacgatac gctggcctgc | 1320 |

| | |
|---|---|
| ccaacctttc ggtataaaga cttcgcgctg ataccagacg ttgcccgcat aattacgaat | 1380 |
| atctgcatcg gcgaactgat cgttaaaact gcctggcaca gcaattgccc ggctttcttg | 1440 |
| taacgcgctt tcccaccaac gctgatcaat tccacagttt tcgcggtcca gactgaatgc | 1500 |
| ccacaggccg tcgagttttt tgatttcacg ggttgggggtt tctacaggac tctagannnn | 1560 |
| nnnnnngcgg ccgctggcac cacctgccag tcaacagacg cgtaaaacag ccagcgctgg | 1620 |
| cgcgatttag ccccgacata gccccactgt tcgtccattt ccgcgcagac gatgacgtca | 1680 |
| ctgcccggct gtatgcgcga ggttaccgac tgcggcctga gttttttaag tgacgtaaaa | 1740 |
| tcgtgttgag gccaacgccc ataatgcggg ctgttgcccg gcatccaacg ccattcatgg | 1800 |
| ccatatcaat gattttctgg tgcgtaccgg gttgagaagc ggtgtaagtg aactgcagtt | 1860 |
| gccatgtttt acggcagtga gagcagagat agcgctgatg tccggcggtg cttttgccgt | 1920 |
| tacgcaccac cccgtcagta gctgaacagg agggacagct gatagacaca gaagccactg | 1980 |
| gagcacctca aaacaccat catacactaa atcagtaagt tggcagcatc acccataatt | 2040 |
| gtggtttcaa atcggctcc gtcgatacta tgttatacgc caactttgaa aacaactttg | 2100 |
| aaaaagctgt tttctggtat ttaaggtttt agaatgcaag gaacagtgaa ttggagttcg | 2160 |
| tcttgttata attagcttct tggggtatct ttaaatactg tagaaaagag gaaggaaata | 2220 |
| ataaatggct aaaatgagaa tatcaccgga attgaaaaaa ctgatcgaaa ataccgctg | 2280 |
| cgtaaaagat acggaaggaa tgtctcctgc taaggtatat aagctggtgg gagaaaatga | 2340 |
| aaacctatat ttaaaaatga cggacagccg gtataaaggg gaccacctatg atgtggaacg | 2400 |
| ggaaaaggac atgatgctat ggctggaagg aaagctgcct gttccaaagg tcctgcactt | 2460 |
| tgaacggcat gatggctgga gcaatctgct catgagtgag gccgatggcg tcctttgctc | 2520 |
| ggaagagtat gaagatgaac aaagccctga aaagattatc gagctgtatg cggagtgcat | 2580 |
| caggctcttt cactccatcg acatatcgga ttgtccctat acgaatagct tagacagccg | 2640 |
| cttagccgaa ttggattact tactgaataa cgatctggcc gatgtggatt gcgaaaactg | 2700 |
| ggaagaagac actccattta agatccgcg cgagctgtat gattttttaa agacggaaaa | 2760 |
| gcccgaagag gaacttgtct tttcccacgg cgacctggga gacagcaaca tctttgtgaa | 2820 |
| agatggcaaa gtaagtggct ttattgatct tgggagaagc ggcagggcgg acaagtggta | 2880 |
| tgacattgcc ttctgcgtcc ggtcgatcag ggaggatatc ggggaagaac agtatgtcga | 2940 |
| gctattttt gacttactgg ggatcaagcc tgattgggag aaaataaaat attatatttt | 3000 |
| actgatgaa ttgttttagt acctagatgt ggcgcaacga tgccggcgac aagcaggagc | 3060 |
| gcaccgactt cttccgcatc aagtgttttg gctctcaggc cgaggccac ggcaagtatt | 3120 |
| tgggcaaggg gtcgctggta ttcgtgcagg caagattcg gaataccaag tacgagaagg | 3180 |
| acggccagac ggtctacggg accgacttca ttgccgataa ggtggattat ctggacacca | 3240 |
| aggcaccagg cggtcaaat caggaataag ggcacattgc cccggcgtga gtcgggcaa | 3300 |
| tcccgcaagg agggtgaatg aatcggacgt ttgaccggaa ggcatacagg caagaactga | 3360 |
| tcgacgcggg gttttccgcc gaggatgccg aaaccatcgc aagccgcacc gtcatgcgtg | 3420 |
| cgccccgcga aaccttccag tccgtcggct cgatggtcca gcaagctacg ccaagatcg | 3480 |
| agcgcgacag cgtgcaactg gctcccctg ccctgcccgc gccatcggcc gccgtggagc | 3540 |
| gttcgcgtcg tctcgaacag gaggcggcag gtttggcgaa gtcgatgacc atcgacacgc | 3600 |
| gaggaactat gacgaccaag aagcgaaaaa ccgccggcga ggacctggca aaacaggtca | 3660 |

```
gcgaggccaa gcaggccgcg ttgctgaaac acacgaagca gcagatcaag gaaatgcagc    3720
tttccttgtt cgatattgcg ccgtggccgg acacgatgcg agcgatgcca aacgacacgg    3780
cccgctctgc cctgttcacc acgcgcaaca agaaaatccc gcgcgaggcg ctgcaaaaca    3840
aggtcatttt ccacgtcaac aaggacgtga agatcaccta caccggcgtc gagctgcggg    3900
ccgacgatga cgaactggtg tggcagcagg tgttggagta cgcgaagcgc acccctatcg    3960
gcgagccgat caccttcacg ttctacgagc tttgccagga cctgggctgg tcgatcaatg    4020
gccggtatta cacgaaggcc gaggaatgcc tgtcgcgcct acaggcgacg gcgatgggct    4080
tcacgtccga ccgcgttggg cacctggaat cggtgtcgct gctgcaccgc ttccgcgtcc    4140
tggaccgtgg caagaaaacg tcccgttgcc aggtcctgat cgacgaggaa atcgtcgtgc    4200
tgtttgctgg cgaccactac acgaaaattca tatgggagaa gtaccgcaag ctgtcgccga    4260
cggcccgacg gatgttcgac tatttcagct cgcaccggga gccgtacccg ctcaagctgg    4320
aaaccttccg cctcatgtgc ggatcggatt ccacccgcgt gaagaagtgg cgcgagcagg    4380
tcggcgaagc ctgcgaagag ttgcgaggca gcggcctggt ggaacacgcc tgggtcaatg    4440
atgacctggt gcattgcaaa cgctagggcc ttgtggggtc agttccggct gggggttcag    4500
cagccagcgc tttactctag tgacgctcac cgggctggtt gccctcgccg ctgggctggc    4560
ggccgtctat ggccctgcaa acgcgccaga acgccgtcg aagccgtgtg cgagacaccg    4620
cggccgccgc cgttgtggat acctcgcgga aaacttggcc ctcactgaca gatgaggggc    4680
ggacgttgac acttgagggg ccgactcacc cggcgcggcg ttgacagatg aggggcaggc    4740
tcgatttcgg ccggcgacgt ggagctgcc agcctcgcaa atcggcgaaa acgcctgatt    4800
ttacgcgagt ttcccacaga tgatgtggac aagcctgggg ataagtgccc tgcggtattg    4860
acacttgagg ggcgcgacta ctgacagatg aggggcgcga tccttgacac ttgaggggca    4920
gagtgctgac agatgagggg cgcacctatt gacatttgag gggctgtcca caggcagaaa    4980
atccagcatt tgcaagggtt tccgcccgtt tttcggccac cgctaacctg tcttttaacc    5040
tgcttttaaa ccaatatttta taaaccttgt ttttaaccag ggctgcgccc tgtgcgcgtg    5100
accgcgcacg ccgaaggggg gtgccccccc ttctcgaacc ctcccggccc gctaacgcgg    5160
gcctcccatc ccccaggggg ctgcgcccct cggccgcgaa cggcctcacc ccaaaaatgg    5220
c                                                                   5221
```

<210> SEQ ID NO 13
<211> LENGTH: 8885
<212> TYPE: DNA
<213> ORGANISM: Artificial Sequence
<220> FEATURE:
<223> OTHER INFORMATION: Construct IV
<220> FEATURE:
<221> NAME/KEY: misc_feature
<222> LOCATION: (3)..(12)
<223> OTHER INFORMATION: n is a, c, g, or t

<400> SEQUENCE: 13

```
ccnnnnnnnn nnttaattaa cgaagagcaa gagctcgaat tccccgatc gttcaaacat      60 ttggcaataa agtttcttaa gattgaatcc tgttgccggt cttgcgatga ttatcatata    120
atttctgttg aattacgtta agcatgtaat aattaacatg taatgcatga cgttatttat    180
gagatgggtt tttatgatta gagtcccgca attatacatt taatacgcga tagaaaacaa    240
aatatagcgc gcaaactagg ataaattatc gcgcgcggtg tcatctatgt tactagatcg    300
ggaattggca tgcaagcttg gcactggccg tcgttttaca acgtcgtgac tgggaaaacc    360
```

-continued

```
ctggcgttac ccaacttaat cgccttgcag cacatccccc tttcgccagc tggcgtaata    420
gcgaagaggc ccgcaccgat cgcccttccc aacagttgcg cagcctgaat ggcgaatgct    480
agagcagctt gagcttggat cagattgtcg tttcccgcct tcagtttaaa ctatcagtgt    540
ttgacaggat atattggcgg gtaaacctaa gagaaaagag cgtttattag aataatcgga    600
tatttaaaag ggcgtgaaaa ggtttatccg ttcgtccatt tgtatgtgca tgccaaccac    660
agggttcccc tcgggatcaa agtactttga tccaaccccct ccgctgctat agtgcagtcg    720
gcttctgacg ttcagtgcag ccgtcttctg aaaacgacat gtcgcacaag tcctaagtta    780
cgcgacaggc tgccgccctg ccctttttcct ggcgttttct tgtcgcgtgt tttagtcgca    840
taaagtagaa tacttgcgac tagaaccgga gacattacgc catgaacaag agcgccgccg    900
ctggcctgct gggctatgcc cgcgtcagca ccgacgacca ggacttgacc aaccaacggg    960
ccgaactgca cgcggccggc tgcaccaagc tgttttccga agatcaccc ggcaccaggc   1020 gcgaccgccc ggagctggcc aggatgcttg accacctacg ccctggcgac gttgtgacag   1080
tgaccaggct agaccgcctg gcccgcagca cccgcgacct actggacatt gccgagcgca   1140
tccaggaggc cggcgcgggc ctgcgtagcc tggcagagcc gtgggccgac accaccacgc   1200
cggccggccg catggtgttg accgtgttcg ccggcattgc cgagttcgag cgttccctaa   1260
tcatcgaccg cacccggagc gggcgcgagg ccgccaaggc ccgaggcgtg aagtttggcc   1320
cccgccctac cctcaccccg gcacagatcg cgcacgcccg cgagctgatc gaccaggaag   1380
gccgcaccgt gaaagaggcg gctgcactgc ttggcgtgca tcgctcgacc ctgtaccgcg   1440
cacttgagcg cagcgaggaa gtgacgccca ccgaggccag gcggcgcggt gccttccgtg   1500
aggacgcatt gaccgaggcc gacgcctggc cggccgccga gaatgaacgc caagaggaac   1560
aagcatgaaa ccgcaccagg acggccagga cgaaccgttt tcattaccg aagagatcga   1620 ggcggagatg atcgcggccg ggtacgtgtt cgagccgccc gcgcacgtct caaccgtgcg   1680
gctgcatgaa atcctggccg gtttgtctga tgccaagctg gcggcctggc cggccagctt   1740
ggccgctgaa gaaaccgagc gccgccgtct aaaaaggtga tgtgtatttg agtaaaacag   1800
cttgcgtcat gcggtcgctg cgtatatgat gcgatgagta aataaacaaa tacgcaaggg   1860
gaacgcatga aggttatcgc tgtacttaac cagaaaggcg ggtcaggcaa gacgaccatc   1920
gcaacccatc tagcccgcgc cctgcaactc gccggggccg atgttctgtt agtcgattcc   1980
gatccccagg gcagtgcccg cgattgggcg ccgtgcggg aagatcaacc gctaaccgtt   2040
gtcggcatcg accgcccgac gattgaccgc gacgtgaagg ccatcggccg gcgcgacttc   2100
gtagtgatcg acggagcgcc ccaggcggcg gacttggctg tgtccgcgat caaggcagcc   2160
gacttcgtgc tgattccggt gcagccaagc ccttacgaca tatgggccac cgccgacctg   2220
gtggagctgg ttaagcagcg cattgaggtc acggatggaa ggctacaagc ggcctttgtc   2280
gtgtcgcggc gatcaaagg cacgcgcatc ggcggtgagg ttgccgaggc gctgccggg   2340 tacgagctgc ccattcttga gtcccgtatc acgcagcgcg tgagctaccc aggcactgcc   2400
gccgccggca caaccgttct tgaatcagaa cccgagggcg acgctgcccg cgaggtccag   2460
gcgctggccg ctgaaattaa atcaaaactc atttgagtta atgaggtaaa gagaaaatga   2520
gcaaaagcac aaaacacgct aagtgccggc cgtccgagcg cacgcagcagc aaggctgcaa   2580 cgttggccag cctggcagac acgccagcca tgaagcgggt caactttcag ttgccggcgg   2640
aggatcacac caagctgaag atgtacgcgg tacgccaagg caagaccatt accgagctgc   2700
```

```
tatctgaata catcgcgcag ctaccagagt aaatgagcaa atgaataaat gagtagatga    2760
attttagcgg ctaaaggagg cggcatggaa aatcaagaac aaccaggcac cgacgccgtg    2820
gaatgcccca tgtgtggagg aacgggcggt tggccaggcg taagcggctg ggttgcctgc    2880
cggccctgca atggcactgg aaccccccaag cccgaggaat cggcgtgagc ggtcgcaaac   2940
catccggccc ggtacaaatc ggcgcggcgc tgggtgatga cctggtggag aagttgaagg    3000
ccgcgcaggc cgcccagcgg caacgcatcg aggcagaagc acgccccggt gaatcgtggc    3060
aagcggccgc tgatcgaatc cgcaaagaat cccggcaacc gccggcagcc ggtgcgccgt    3120
cgattaggaa gccgcccaag ggcgacgagc aaccagattt tttcgttccg atgctctatg    3180
acgtgggcac ccgcgatagt cgcagcatca tggacgtggc cgttttccgt ctgtcgaagc    3240
gtgaccgacg agctggcgag gtgatccgct acgagcttcc agacgggcac gtagaggttt    3300
ccgcagggcc ggccggcatg ccagtgtgt gggattacga cctggtactg atggcggttt     3360
cccatctaac cgaatccatg aaccgatacc gggaagggaa gggagacaag cccggccgcg    3420
tgttccgtcc acacgttgcg gacgtactca agttctgccg gcgagccgat ggcggaaagc    3480
agaaagacga cctggtagaa acctgcattc ggttaaacac cacgcacgtt gccatgcagc    3540
gtacgaagaa ggccaagaac ggccgcctgg tgacggtatc cgagggtgaa gccttgatta    3600
gccgctacaa gatcgtaaag agcgaaaccg ggcggccgga gtacatcgag atcgagctag    3660
ctgattggat gtaccgcgag atcacagaag gcaagaaccc ggacgtgctg acggttcacc    3720
ccgattactt tttgatcgat cccggcatcg gccgttttct ctaccgcctg gcacgccgcg    3780
ccgcaggcaa ggcagaagcc agatggttgt tcaagacgat ctacgaacgc agtggcagcg    3840
ccggagagtt caagaagttc tgtttcaccg tgcgcaagct gatcgggtca aatgacctgc    3900
cggagtacga tttgaaggag gaggcggggc aggctggccc gatcctagtc atgcgctacc    3960
gcaacctgat cgagggcgaa gcatccgccg gttcctaatg tacggagcag atgctagggc    4020
aaattgccct agcaggggaa aaaggtcgaa aaggtctctt tcctgtggat agcacgtaca    4080
ttgggaaccc aaagccgtac attgggaacc ggaacccgta cattgggaac ccaaagccgt    4140
acattgggaa ccggtcacac atgtaagtga ctgatataaa agagaaaaaa ggcgattttt    4200
ccgcctaaaa ctcttaaaa cttattaaaa ctcttaaaac ccgcctggcc tgtgcataac     4260
tgtctggcca gcgcacagcc gaagagctgc aaaaagcgcc tacccttcgg tcgctgcgct    4320
ccctacgccc cgccgcttcg cgtcggccta tcgcggccgc tggccgctca aaaatggctg    4380
gcctacggcc aggcaatcta ccagggcgcg acaagccgc cgtcgcca ctcgaccgcc       4440
ggcgcccaca tcaaggcacc ctgcctcgcg cgtttcggtg atgacggtga aaacctctga    4500
cacatgcagc tcccggagac ggtcacagct tgtctgtaag cggatgccgg gagcagacaa    4560
gcccgtcagg gcgcgtcagc gggtgttggc gggtgtcggg gcgcagccat gacccagtca    4620
cgtagcgata gcggagtgta tactggctta actatgcggc atcagagcag attgtactga    4680
gagtgcacca tatgcggtgt gaaataccgc acagatgcgt aaggagaaaa taccgcatca    4740
ggcgctcttc cgcttcctcg ctcactgact cgctgcgctc ggtcgttcgg ctgcggcgag    4800
cggtatcagc tcactcaaag gcggtaatac ggttatccac agaatcaggg gataacgcag    4860
gaaagaacat gtgagcaaaa ggccagcaaa aggccaggaa ccgtaaaaag gccgcgttgc    4920
tggcgttttt ccataggctc cgcccccctg acgagcatca aaaaatcga cgctcaagtc     4980
agaggtggcg aaacccgaca ggactataaa gataccaggc gtttccccct ggaagctccc    5040
tcgtgcgctc tcctgttccg accctgccgc ttaccggata cctgtccgcc tttctccctt    5100
```

```
cgggaagcgt ggcgctttct catagctcac gctgtaggta tctcagttcg gtgtaggtcg   5160
ttcgctccaa gctgggctgt gtgcacgaac cccccgttca gcccgaccgc tgcgccttat   5220
ccggtaacta tcgtcttgag tccaacccgg taagacacga cttatcgcca ctggcagcag   5280
ccactggtaa caggattagc agagcgaggt atgtaggcgg tgctacagag ttcttgaagt   5340
ggtggcctaa ctacggctac actagaagga cagtatttgg tatctgcgct ctgctgaagc   5400
cagttacctt cggaaaaaga gttggtagct cttgatccgg caaacaaacc accgctggta   5460
gcggtggttt ttttgtttgc aagcagcaga ttacgcgcag aaaaaaagga tctcaagaag   5520
atcctttgat cttttctacg gggtctgacg ctcagtggaa cgaaaactca cgttaaggga   5580
ttttggtcat gcattctagg tactaaaaca attcatccag taaaatataa tattttattt   5640
tctcccaatc aggcttgatc cccagtaagt caaaaaatag ctcgacatac tgttcttccc   5700
cgatatcctc cctgatcgac cggacgcaga aggcaatgtc ataccacttg tccgccctgc   5760
cgcttctccc aagatcaata aagccactta ctttgccatc tttcacaaag atgttgctgt   5820
ctcccaggtc gccgtgggaa aagacaagtt cctcttcggg cttttccgtc tttaaaaaat   5880
catacagctc gcgcggatct ttaaatggag tgtcttcttc ccagttttcg caatccacat   5940
cggccagatc gttattcagt aagtaatcca attcggctaa gcggctgtct aagctattcg   6000 tatgggaca atccgatatg tcgatggagt gaaagagcct gatgcactcc gcatacagct   6060
cgataatctt ttcagggctt tgttcatctt catactcttc cgagcaaagg acgccatcgg   6120
cctcactcat gagcagattg ctccagccat catgccgttc aaagtgcagg acctttggaa   6180
caggcagctt tccttccagc catagcatca tgtccttttc ccgttccaca tcataggtgg   6240 tcccttttata ccggctgtcc gtcatttta aatataggtt ttcatttct cccaccagct   6300 tatataccttt agcaggagac attccttccg tatcttttac gcagcggtat ttttcgatca   6360
gttttttcaa ttccggtgat attctcattt tagccattta ttatttcctt cctcttttct   6420
acagtattta aagataccccc aagaagctaa ttataacaag acgaactcca attcactgtt   6480
ccttgcattc taaaaccctta aataccagaa aacagctttt tcaaagttgt tttcaaagtt   6540
ggcgtataac atagtatcga cggagccgat tttgaaaccg cggtgatcac aggcagcaac   6600
gctctgtcat cgttacaatc aacatgctac cctccgcgag atcatccgtg tttcaaaccc   6660
ggcagcttag ttgccgttct tccgaatagc atcggtaaca tgagcaaagt ctgccgcctt   6720
acaacggctc tcccgctgac gccgtcccgg actgatgggc tgcctgtatc gagtggtgat   6780
tttgtgccga gctgccggtc ggggagctgt tggctggctg gtggcaggat atattgtggt   6840
gtaaacaaat tgacgcttag acaacttaat aacacattgc ggacgttttt aatgtactga   6900
attaacgccg aattaagctt ggacaatcag taaattgaac ggagaatatt attcataaaa   6960
atacgatagt aacgggtgat atattcatta gaatgaaccg aaaccggcgg taaggatctg   7020
agctacacat gctcaggttt tttacaacgt gcacaacaga attgaaagca atatcatgc    7080 gatcataggc gtctcgcata tctcattaaa gcagggcatg ccggtcgagt caaatctcgg   7140
tgacgggcag gaccggacgg ggcggtaccg gcaggctgaa gtccagctgc cagaaaccca   7200
cgtcatgcca gttcccgtgc ttgaagccgg ccgcccgcga catgccgcgg ggggcatatc   7260
cgagcgcctc gtgcatgcgc acgctcgggt cgttgggcag cccgatgaca gcgaccacgc   7320
tcttgaagcc ctgtgcctcc agggacttca gcaggtgggt gtagagcgtg agcccagtc    7380 ccgtccgctg gtggcggggg gagacgtaca cggtcgactc ggccgtccag tcgtaggcgt   7440
```

| | |
|---|---|
| tgcgtgcctt ccaggggccc gcgtaggcga tgccggcgac ctcgccgtcc acctcggcga | 7500 |
| cgagccaggg atagcgctcc cgcagacgga cgaggtcgtc cgtccactcc tgcggttcct | 7560 |
| gcggctcggt acggaagttg accgtgcttg tctcgatgta gtggttgacg atggtgcaga | 7620 |
| ccgccggcat gtccgcctcg gtggcacggc ggatgtcggc cgggcgtcgt tctgggctca | 7680 |
| tggtagactc gacggatcca cgtgtggaag atatgaattt ttttgagaaa ctagataaga | 7740 |
| ttaatgaata tcggtgtttt ggttttttct tgtggccgtc tttgtttata ttgagatttt | 7800 |
| tcaaatcagt gcgcaagacg tgacgtaagt atccgagtca gttttatttt ttctactaat | 7860 |
| ttggtcgaag ctttgggcgg atcctctaga attcgaatcc aaaaattacg gatatgaata | 7920 |
| taggcatatc cgtatccgaa ttatccgttt gacagctagc aacgattgta caattgcttc | 7980 |
| tttaaaaaag gaagaaagaa agaaagaaaa gaatcaacat cagcgttaac aaacggcccc | 8040 |
| gttacggccc aaacggtcat atagagtaac ggcgttaagc gttgaaagac tcctatcgaa | 8100 |
| atacgtaacc gcaaacgtgt catagtcaga tcccctcttc cttcaccgcc tcaaacacaa | 8160 |
| aaataatctt ctacagccta tatatacaac ccccccttct atctctcctt tctcacaatt | 8220 |
| catcatcttt ctttctctac ccccaatttt aagaaatcct ctcttctcct cttcattttc | 8280 |
| aaggtaaatc tctctctctc tctctctctc tgttattcct tgttttaatt aggtatgtat | 8340 |
| tattgctagt ttgttaatct gcttatctta tgtatgcctt atgtgaatat ctttatcttg | 8400 |
| ttcatctcat ccgtttagaa gctataaatt tgttgatttg actgtgtatc tacacgtggt | 8460 |
| tatgtttata tctaatcaga tatgaatttc ttcatattgt tgcgtttgtg tgtaccaatc | 8520 |
| cgaaatcgtt gatttttttc atttaatcgt gtagctaatt gtacgtatac atatggatct | 8580 |
| acgtatcaat tgttcatctg tttgtgtttg tatgtataca gatctgaaaa catcacttct | 8640 |
| ctcatctgat tgtgttgtta catacataga tatagatctg ttatatcatt ttttttatta | 8700 |
| attgtgtata tatatatgtg catagatctg gattacatga ttgtgattat ttacatgatt | 8760 |
| ttgttatta cgtatgtata tatgtagatc tggactttt ggagtgttg acttgattgt | 8820 |
| atttgtgtgt gtatatgtgt gttctgatct tgatatgtta tgtatgtgca gcccggggtg | 8880 |
| ctctt | 8885 |

```
<210> SEQ ID NO 14
<211> LENGTH: 10934
<212> TYPE: DNA
<213> ORGANISM: Artificial Sequence
<220> FEATURE:
<223> OTHER INFORMATION: Construct V
<220> FEATURE:
<221> NAME/KEY: misc_feature
<222> LOCATION: (612)..(621)
<223> OTHER INFORMATION: n is a, c, g, or t

<400> SEQUENCE: 14
```

| | |
|---|---|
| gtagaaaccc caacccgtga aatcaaaaaa ctcgacggcc tgtgggcatt cagtctggat | 60 |
| cgcgaaaact gtggaattga tcagcgttgg tgggaaagcg cgttacaaga aagccgggca | 120 |
| attgctgtgc caggcagttt taacgatcag ttcgccgatg cagatattcg taattatgcg | 180 |
| ggcaacgtct ggtatcagcg cgaagtcttt ataccgaaag gttgggcagg ccagcgtatc | 240 |
| gtgctgcgtt tcgatgcggt cactcattac ggcaaagtgt gggtcaataa tcaggaagtg | 300 |
| atggagcatc agggcggcta tacgccattt gaagccgatg tcacgccgta tgttattgcc | 360 |
| gggaaaagtg tacgtatcac cgtttgtgtg aacaacgaac tgaactggca gactatcccg | 420 |
| ccgggaatgg tgattaccga cgaaaacggc aagaaaaagc agtcttactt ccatgatttc | 480 |

```
tttaactatg ccggaatcca tcgcagcgta atgctctaca ccacgccgaa cacctgggtg      540
gacgatatca ccgtggtgac gcatgtcgcg caagactgta accacgcgtc tgttgactgg      600
caggtggtgc cnnnnnnnnn nctagagtcc tgtagaaacc ccaacccgtg aaatcaaaaa      660
actcgacggc ctgtgggcat tcagtctgga ccgcgaaaac tgtggaattg atcagcgttg      720
gtgggaaagc gcgttacaag aaagccgggc aattgctgtg ccaggcagtt ttaacgatca      780
gttcgccgat gcagatattc gtaattatgc gggcaacgtc tggtatcagc gcgaagtctt      840
tataccgaaa ggttgggcag gccagcgtat cgtgctgcgt ttcgatgcgg tcactcatta      900
cggcaaagtg tgggtcaata atcaggaagt gatggagcat cagggcggct atacgccatt      960
tgaagccgat gtcacgccgt atgttattgc cgggaaaagt gtacgtatca ccgtttgtgt     1020
gaacaacgaa ctgaactggc agactatccc gccgggaatg gtgattaccg acgaaaacgg     1080
caagaaaaag cagtcttact tccatgattt ctttaactat gccggaatcc atcgcagcgt     1140
aatgctctac accacgccga acacctgggt ggacgatatc accgtggtga cgcatgtcgc     1200
gcaagactgt aaccacgcgt ctgttgactg gcaggtggtg gccaatggtg atgtcagcgt     1260
tgaactgcgt gatgcggatc aacaggtggt tgcaactgga caaggcacta gcgggacttt     1320
gcaagtggtg aatccgcacc tctggcaacc gggtgaaggt tatctctatg aactgtgcgt     1380
cacagccaaa agccagacag agtgtgatat ctacccgctt cgcgtcggca tccggtcagt     1440
ggcagtgaag ggcgaacagt tcctgattaa ccacaaaccg ttctacttta ctggctttgg     1500
tcgtcatgaa gatgcggact tgcgtggcaa aggattcgat aacgtgctga tggtgcacga     1560
ccacgcatta atggactgga ttggggccaa ctcctaccgt acctcgcatt acccttacgc     1620
tgaagagatg ctcgactggg cagatgaaca tggcatcgtg gtgattgatg aaactgctgc     1680
tgtcggcttt aacctctctt taggcattgg tttcgaagcg ggcaacaagc cgaaagaact     1740
gtacagcgaa gaggcagtca acggggaaac tcagcaagcg cacttacagg cgattaaaga     1800
gctgatagcg cgtgacaaaa accacccaag cgtggtgatg tggagtattg ccaacgaacc     1860
ggatacccgt ccgcaaggtg cacgggaata tttcgcgcca ctggcggaag caacgcgtaa     1920
actcgacccg acgcgtccga tcacctgcgt caatgtaatg ttctgcgacg ctcacaccga     1980
taccatcagc gatctctttg atgtgctgtg cctgaaccgt tattacggat ggtatgtcca     2040
aagcggcgat ttggaagcgg cagagaaggt actggaaaaa gaacttctgg cctggcagga     2100
gaaactgcat cagccgatta tcatcaccga atacggcgtg gatacgttag ccgggctgca     2160
ctcaatgtac accgacatgt ggagtgaaga gtatcagtgt gcatggctgg atatgtatca     2220
ccgcgtcttt gatcgcgtca gcgccgtcgt cggtgaacag gtatggaatt cgccgatttt     2280
tgcgacctcg caaggcatat tgcgcgttgg cggtaacaag aaagggatct tcactcgcga     2340
ccgcaaaccg aagtcggcgg cttttctgct gcaaaaacgc tggactggca tgaacttcgg     2400
tgaaaaaccg cagcagggag gcaaacaatg aatcaacaac tctcctggcg caccatcgtc     2460
ggctacagcc tcgggaattg ctaccgagct cgaatttccc cgatcgttca acatttggc      2520 aataaagttt cttaagattg aatcctgttg ccggacttgc gatgattatc atataatttc     2580
tgttgaatta cgttaagcat gtaataatta acatgtaatg catgacgtta tttatgagat     2640 gggttttat gattagagtc ccgcaattat acatttaata cgcgatagaa acaaaatat      2700 agcgcgcaaa ctaggataaa ttatcgcgcg cggtgtcatc tatgttacta gatcggaata     2760
agcttggcgt aatcatggtc atagctgttt cctactagat ctgattgtcg tttcccgcct     2820
```

```
tcagtttaaa ctatcagtgt tgacaggat atattggcgg gtaaacctaa gagaaaagag     2880
cgtttattag aataatcgga tatttaaaag ggcgtgaaaa ggtttatccg ttcgtccatt     2940
tgtatgtcca tggaacgcag tggcggtttt catggcttgt tatgactgtt tttttggggt     3000
acagtctatg cctcgggcat ccaagcagca agcgcgttac gccgtgggtc gatgtttgat     3060
gttatggagc agcaacgatg ttacgcagca gggcagtcgc cctaaaacaa agttaaacat     3120
catgggggaa gcggtgatcg ccgaagtatc gactcaacta tcagaggtag ttggcgtcat     3180
cgagcgccat ctcgaaccga cgttgctggc cgtacatttg tacggctccg cagtggatgg     3240
cggcctgaag ccacacagtg atattgattt gctggttacg gtgaccgtaa ggcttgatga     3300
aacaacgcgg cgagctttga tcaacgacct tttggaaact tcggcttccc ctggagagag     3360
cgagattctc cgcgctgtag aagtcaccat tgttgtgcac gacgacatca ttccgtggcg     3420
ttatccagct aagcgcgaac tgcaatttgg agaatggcag cgcaatgaca ttcttgcagg     3480
tatcttcgag ccagccacga tcgacattga tctggctatc ttgctgacaa agcaagaga     3540 acatagcgtt gccttggtag gtccagcggc ggaggaactc tttgatccgg ttcctgaaca     3600
ggatctattt gaggcgctaa atgaaaacctt aacgctatgg aactcgccgc ccgactgggc     3660
tggcgatgag cgaaatgtag tgcttacgtt gtcccgcatt tggtacagcg cagtaaccgg     3720
caaaatcgcg ccgaaggatg tcgctgccga ctgggcaatg agcgcctgc cggcccagta     3780 tcagcccgtc atacttgaag ctagacaggc ttatcttgga caagaagaag atcgcttggc     3840
ctcgcgcgca gatcagttgg aagaatttgt ccactacgtg aaaggcgaga tcaccaaggt     3900
agtcggcaaa taatgtctag ctagaaattc gttcaagccg acgccgcttc gcggcgcggc     3960
ttaactcaag cgttagatgc actaagcaca taattgctca cagccaaact atcaggtcaa     4020
gtctgctttt attattttta agcgtgcata ataagccta cacaaattgg gagatatatc     4080
atgcatgacc aaaatcccctt aacgtgagtt tcgttccac tgagcgtcag accccgtaga     4140
aaagatcaaa ggatcttctt gagatccttt ttttctgcgc gtaatctgct gcttgcaaac     4200
aaaaaaacca ccgctaccag cggtggtttg tttgccggat caagagctac caactctttt     4260
tccgaaggta actggcttca gcagagcgca gataccaaat actgtccttc tagtgtagcc     4320
gtagttaggc caccacttca agaactctgt agcaccgcct acatacctcg ctctgctaat     4380
cctgttacca gtggctgctg ccagtggcga taagtcgtgt cttaccgggt tggactcaag     4440
acgatagtta ccggataagg cgcagcggtc gggctgaacg gggggttcgt gcacacagcc     4500
cagcttggag cgaacgacct acaccgaact gagatacccta cagcgtgagc tatgagaaag     4560
cgccacgctt cccgaaggga gaaaggcgga caggtatccg gtaagcggca gggtcggaac     4620
aggagagcgc acgagggagc ttccagggg aaacgcctgg tatctttata gtcctgtcgg     4680
gtttcgccac ctctgacttg agcgtcgatt tttgtgatgc tcgtcagggg ggcggagcct     4740
atggaaaaac gccagcaacg cggcctttt acggttcctg gccttttgct ggccttttgc     4800
tcacatgttc tttcctgcgt tatcccctga ttctgtggat aaccgtatta ccgcctttga     4860
gtgagctgat accgctcgcc gcagccgaac gaccgagcgc agcgagtcag tgagcgagga     4920
agcggaagag cgcctgatgc ggtatttctt ccttacgcat ctgtgcggta tttcacaccg     4980
catatggtgc actctcagta caatctgctc tgatgccgca tagttaagcc agtatacact     5040
ccgctatcgc tacgtgactg gtcatggct gcgccccgac accgccaac acccgctgac     5100 gcgccctgac gggcttgtct gctcccggca tccgcttaca gacaagctgt gaccgtctcc     5160
gggagctgca tgtgtcagag gttttcaccg tcatcaccga aacgcgcgag gcagggtgcc     5220
```

```
ttgatgtggg cgccggcggt cgagtggcga cggcgcggct tgtccgcgcc ctggtagatt   5280
gcctggccgt aggccagcca tttttgagcg gccagcggcc gcgataggcc gacgcgaagc   5340
ggcggggcgt agggagcgca gcgaccgaag ggtaggcgct ttttgcagct cttcggctgt   5400
gcgctggcca gacagttatg cacaggccag gcgggtttta agagttttaa taagttttaa   5460
agagttttag gcggaaaaat cgccttttt ctcttttata tcagtcactt acatgtgtga    5520
ccggttccca atgtacggct ttgggttccc aatgtacggg ttccggttcc caatgtacgg   5580
ctttgggttc ccaatgtacg tgctatccac aggaaagaga cctttcgac cttttcccc     5640 tgctagggca atttgcccta gcatctgctc cgtacattag gaaccggcgg atgcttcgcc   5700
ctcgatcagg ttgcggtagc gcatgactag gatcgggcca gcctgccccg cctcctcctt   5760
caaatcgtac tccggcaggt catttgaccc gatcagcttg cgcacggtga aacagaactt   5820
cttgaactct ccggcgctgc cactgcgttc gtagatcgtc ttgaacaacc atctggcttc   5880
tgccttgcct gcgcgcggc gtgccaggcg gtagagaaaa cggccgatgc cgggatcgat    5940
caaaaagtaa tcggggtgaa ccgtcagcac gtccgggttc ttgccttctg tgatctcgcg   6000
gtacatccaa tcagctagct cgatctcgat gtactccggc cgcccggttt cgctcttac    6060 gatcttgtag cggctaatca aggcttcacc ctcggatacc gtcaccaggc ggccgttctt   6120
ggccttcttc gtacgctgca tgcaacgtg cgtggtgttt aaccgaatgc aggtttctac    6180
caggtcgtct ttctgctttc cgccatcggc tcgccggcag aacttgagta cgtccgcaac   6240
gtgtggacgg aacacgcggc cgggcttgtc tcccttccct tcccggtatc ggttcatgga   6300
ttcggttaga tgggaaaccg ccatcagtac caggtcgtaa tcccacacac tggccatgcc   6360
ggccggccct gcggaaacct ctacgtgccc gtctggaagc tcgtagcgga tcacctcgcc   6420
agctcgtcgg tcacgcttcg acagacggaa aacggccacg tccatgatgc tgcgactatc   6480
gcgggtgccc acgtcataga gcatcggaac gaaaaaatct ggttgctcgt cgcccttggg   6540
cggcttccta atcgacggcg caccggctgc cggcggttgc cgggattctt tgcggattcg   6600
atcagcggcc gcttgccacg attcaccggg gcgtgcttct gcctcgatgc gttgccgctg   6660
ggcggcctgc gcggccttca acttctccac caggtcatca cccagcgccg cgccgatttg   6720
taccgggccg gatggtttgc gaccgctcac gccgattcct cgggcttggg ggttccagtg   6780
ccattgcagg gccggcagac aacccagccg cttacgcctg gccaaccgcc cgttcctcca   6840
cacatggggc attccacggc gtcggtgcct ggttgttctt gattttccat gccgcctcct   6900
ttagccgcta aaattcatct actcatttat tcatttgctc atttactctg gtagctgcgc   6960
gatgtattca gatagcagct cggtaatggt cttgccttgg cgtaccgcgt acatcttcag   7020
cttggtgtga tcctccgccg gcaactgaaa gttgacccgc ttcatggctg gcgtgtctgc   7080
caggctggcc aacgttgcag ccttgctgct gcgtgcgctc ggacggccgg cacttagcgt   7140
gtttgtgctt ttgctcattt tctctttacc tcattaactc aaatgagttt tgatttaatt   7200
tcagcggcca gcgcctggac ctcgcgggca gcgtcgccct cgggttctga ttcaagaacg   7260
gttgtgccgg cggcggcagt gcctgggtag ctcacgcgct gcgtgatacg ggactcaaga   7320
atgggcagct cgtacccggc cagcgcctcg gcaacctcac cgccgatgcg cgtgcctttg   7380
atcgcccgcg acacgacaaa ggccgcttgt agccttccat ccgtgacctc aatgcgctgc   7440
ttaaccagct ccaccaggtc ggcggtgcc catatgtcgt aagggcttgg ctgcaccgga   7500
atcagcacga agtcggctgc cttgatcgcg gacacagcca agtccgccgc ctggggcgct   7560
```

```
ccgtcgatca ctacgaagtc gcgccggccg atggccttca cgtcgcggtc aatcgtcggg    7620
cggtcgatgc cgacaacggt tagcggttga tcttcccgca cggccgccca atcgcgggca    7680
ctgccctggg gatcggaatc gactaacaga acatcggccc cggcgagttg cagggcgcgg    7740
gctagatggg ttgcgatggt cgtcttgcct gacccgcctt tctggttaag tacagcgata    7800
accttcatgc gttcccttg cgtatttgtt tatttactca tcgcatcata tacgcagcga    7860
ccgcatgacg caagctgttt tactcaaata cacatcacct ttttagacgg cggcgctcgg    7920
tttcttcagc ggccaagctg gccggccagg ccgccagctt ggcatcagac aaaccggcca    7980
ggatttcatg cagccgcacg gttgagacgt gcgcgggcgg ctcgaacacg tacccggccg    8040
cgatcatctc cgcctcgatc tcttcggtaa tgaaaaacgg ttcgtcctgg ccgtcctggt    8100
gcggtttcat gcttgttcct cttggcgttc attctcggcg gccgccaggg cgtcggcctc    8160
ggtcaatgcg tcctcacgga aggcaccgcg ccgcctggcc tcggtgggcg tcacttcctc    8220
gctgcgctca agtgcgcggt acagggtcga gcgatgcacg ccaagcagtg cagccgcctc    8280
tttcacggtg cggccttcct ggtcgatcag ctcgcgggcg tgcgcgatct gtgccggggt    8340
gagggtaggg cggggccaa acttcacgcc tcgggccttg gcggcctcgc gcccgctccg    8400
ggtgcggtcg atgattaggg aacgctcgaa ctcggcaatg ccggcgaaca cggtcaacac    8460
catgcggccg ccggcgtgg tggtaacgcg tggtgatttt tgtgccgagct gccggtcggg    8520
gagctgttgg ctggctggtg gcaggatata ttgtggtgta aacaaattga cgcttagaca    8580
acttaataac acattgcgga cgtctttaat gtactgaatt aacatccgtt tgatacttgt    8640
ctaaaattgg ctgatttcga gtgcatctat gcataaaaac aatctaatga caattattac    8700
caagcaggat cctgtcaaac actgatagtt taaactgaag gcgggaaacg acaatctgat    8760
catgagcgga gaattaaggg agtcacgtta tgaccccgc cgatgacgcg ggacaagccg    8820
ttttacgttt ggaactgaca gaaccgcaac gttgaaggag ccactcagcc gcgggtttct    8880
ggagtttaat gagctaagca catacgtcag aaaccattat tgcgcgttca aaagtcgcct    8940
aaggtcacta tcagctagca aatatttctt gtcaaaaatg ctccactgac gttccataaa    9000
ttcccctcgg tatccaatta gagtctcata ttcactctca atccaaataa tctgcaccgg    9060
atctggatcg tttcgcatga ttgaacaaga tggattgcac gcaggttctc cggccgcttg    9120
ggtggagagg ctattcggct atgactgggc acaacagaca atcggctgct ctgatgccgc    9180
cgtgttccgg ctgtcagcgc agggggcgccc ggttcttttt gtcaagaccg acctgtccgg    9240
tgccctgaat gaactgcagg acgaggcagc gcggctatcg tggctggcca cgacgggcgt    9300
tccttgcgca gctgtgctcg acgttgtcac tgaagcggga agggactggc tgctattggg    9360
cgaagtgccg gggcaggatc tcctgtcatc tcaccttgct cctgccgaga agtatccat    9420
catggctgat gcaatgcggc ggctgcatac gcttgatccg gctacctgcc cattcgacca    9480
ccaagcgaaa catcgcatcg agcgagcacg tactcggatg gaagccggtc ttgtcgatca    9540
ggatgatctg gacgaagagc atcaggggct cgcgccagcc gaactgttcg ccaggctcaa    9600
ggcgcgcatg cccgacggcg aggatctcgt cgtgacccat ggcgatgcct gcttgccgaa    9660
tatcatggtg gaaaatggcc gcttttctgg attcatcgac tgtggccggc tgggtgtggc    9720
ggaccgctat caggacatag cgttggctac ccgtgatatt gctgaagagc ttggcggcga    9780
atgggctgac cgcttcctcg tgctttacgg tatcgccgct cccgattcgc agcgcatcgc    9840
cttctatcgc cttcttgacg agttcttctg agcgggaccc aagctctaga tcttgctgcg    9900
ttcggatatt ttcgtggagt tcccgccaca gacccggatg atccccgatc gttcaaacat    9960
```

-continued

```
ttggcaataa agtttcttaa gattgaatcc tgttgccggt cttgcgatga ttatcatata    10020
atttctgttg aattacgtta agcatgtaat aattaacatg taatgcatga cgttatttat    10080
gagatgggtt tttatgatta gagtcccgca attatacatt taatacgcga tagaaaacaa    10140
aatatagcgc gcaaactagg ataaattatc gcgcgcggtg tcatctatgt tactagatcg    10200
ggcctcctgt caagctctga gtcgttgtaa aacgacggcc agtgaattga gctcggtacc    10260
gagtcaaaga ttcaaataga ggacctaaca gaactcgccg taaagactgg cgaacagttc    10320
atacagagtc tcttacgact caatgacaag aagaaaatct tcgtcaacat ggtggagcac    10380
gacacgcttg tctactccaa aaatatcaaa gatacagtct cagaagacca aagggcaatt    10440 gagactttc aacaagggt aatatccgga aacctcctcg gattccattg cccagctatc    10500
tgtcacttta ttgtgaagat agtggaaaag gaaggtggct cctacaaatg ccatcattgc    10560
gataaaggaa aggccatcgt tgaagatgcc tctgccgaca gtggtcccaa agatggaccc    10620
ccacccacga ggagcatcgt ggaaaaagaa gacgttccaa ccacgtcttc aaagcaagtg    10680
gattgatgtg atatctccac tgacgtaagg gatgacgcac aatcccacta tccttcgcaa    10740
gaccctctcc tctatataagg aagttcattt catttggaga ggacagggta cgtacctaga    10800
atacaaagaa gaggaagaag aaacctctac agaagaaagt gatggatccc cgggatcatc    10860
tacttctgaa gactcagact cagactaagc aggtgacgaa cgtcaccaat cccaattcga    10920
tctacatccg tcct                                                       10934
```

<210> SEQ ID NO 15
<211> LENGTH: 235
<212> TYPE: PRT
<213> ORGANISM: Saccharomyces cerevisiae

<400> SEQUENCE: 15

```
Met Lys Asn Ile Lys Lys Asn Gln Val Met Asn Thr Gly Pro Asn Ser
1               5                   10                  15

Lys Leu Leu Lys Glu Tyr Lys Ser Gln Leu Ile Glu Leu Asn Ile Glu
            20                  25                  30

Gln Phe Glu Ala Gly Ile Gly Leu Ile Leu Gly Asp Ala Tyr Ile Arg
        35                  40                  45

Ser Arg Asp Glu Gly Lys Thr Tyr Cys Met Gln Phe Glu Trp Lys Asn
    50                  55                  60

Lys Ala Tyr Met Asp His Val Cys Leu Leu Tyr Asp Gln Trp Val Leu
65                  70                  75                  80

Ser Pro Pro His Lys Lys Glu Arg Val Asn His Leu Gly Asn Leu Val
                85                  90                  95

Ile Thr Trp Gly Ala Gln Thr Phe Lys His Gln Ala Phe Asn Lys Leu
            100                 105                 110

Ala Asn Leu Phe Ile Val Asn Asn Lys Lys Thr Ile Pro Asn Asn Leu
        115                 120                 125

Val Glu Asn Tyr Leu Thr Pro Met Ser Thr Ala Tyr Trp Phe Met Asp
    130                 135                 140

Asp Gly Gly Lys Trp Asp Tyr Asn Lys Asn Ser Thr Asn Lys Ser Ile
145                 150                 155                 160

Val Leu Asn Thr Gln Ser Phe Thr Phe Glu Glu Val Glu Tyr Leu Val
                165                 170                 175

Lys Gly Leu Arg Asn Lys Phe Gln Leu Asn Cys Tyr Val Lys Ile Asn
            180                 185                 190
```

```
Lys Asn Lys Pro Ile Ile Tyr Ile Asp Ser Met Ser Tyr Thr Ile Phe
            195                 200                 205

Tyr Asn Leu Ile Lys Pro Tyr Leu Ile Pro Gln Met Met Tyr Lys Thr
            210                 215                 220

Pro Asn Thr Ile Ser Ser Glu Thr Phe Leu Lys
225                 230                 235

<210> SEQ ID NO 16
<211> LENGTH: 238
<212> TYPE: PRT
<213> ORGANISM: Zygosaccharomyces bisporus

<400> SEQUENCE: 16

Met Lys Phe Ile Lys Lys Glu Gln Ile Lys Asn Leu Gly Pro Asn Ser
1               5                   10                  15

Lys Leu Leu Lys Gln Tyr Lys Ser Gln Leu Thr Asn Leu Thr Ser Glu
            20                  25                  30

Gln Leu Glu Ile Gly Val Gly Leu Leu Leu Gly Asp Ala Tyr Ile Arg
        35                  40                  45

Ser Arg Asp Asn Gly Lys Thr Asn Cys Ile Gln Phe Glu Trp Lys Asn
50                  55                  60

Lys Ala Tyr Ile Asp His Ile Cys Leu Lys Phe Asp Glu Trp Val Leu
65                  70                  75                  80

Ser Pro Pro His Lys Met Arg Ile Asn His Leu Gly Asn Glu Val
            85                  90                  95

Ile Thr Trp Gly Ala Gln Thr Phe Lys His Glu Ala Phe Asn Glu Leu
            100                 105                 110

Ser Lys Leu Phe Ile Ile Asn Asn Lys Lys His Ile Ile Asn Asn Leu
            115                 120                 125

Ile Glu Asp Tyr Val Thr Pro Lys Ser Leu Ala Tyr Trp Phe Met Asp
        130                 135                 140

Asp Gly Gly Lys Trp Asp Tyr Asn Lys Gly Ser Met Asn Lys Ser Ile
145                 150                 155                 160

Val Leu Asn Thr Gln Cys Phe Thr Ile Asp Glu Val Asn Ser Leu Ile
                165                 170                 175

Asn Gly Leu Asn Thr Lys Phe Lys Leu Asn Cys Ser Met Lys Phe Asn
            180                 185                 190

Lys Asn Lys Pro Ile Ile Tyr Ile Pro His Asn Ser Tyr Asn Ile Tyr
            195                 200                 205

Tyr Glu Leu Ile Ser Pro Tyr Ile Ile Thr Glu Met Arg Tyr Lys Leu
            210                 215                 220

Pro Ser Tyr Glu Gly Thr Ser Lys Asp Tyr Asn Lys Ile His
225                 230                 235

<210> SEQ ID NO 17
<211> LENGTH: 228
<212> TYPE: PRT
<213> ORGANISM: Lachancea thermotolerans

<400> SEQUENCE: 17

Met Thr Met Lys Tyr Ile Thr Lys Gln Gln Ile Lys Asn Leu Gly Pro
1               5                   10                  15

Asn Ser Lys Leu Leu Lys Gln Tyr Lys Ala Gln Leu Thr Arg Leu Thr
            20                  25                  30

Thr Val Gln Leu Glu Ala Gly Val Gly Leu Ile Leu Gly Asp Ala Tyr
        35                  40                  45
```

Ile Arg Ser Arg Asp Glu Gly Lys Thr Tyr Cys Met Gln Phe Glu Trp
 50                  55                  60

Lys Asn Glu Ala Tyr Ile Asn His Val Cys Lys Leu Tyr Asp Glu Trp
 65                  70                  75                  80

Val Leu Ser Ser Pro His Lys Lys Val Arg Thr Asn His Leu Gly Asn
                 85                  90                  95

Glu Val Val Thr Trp Gly Ala Gln Thr Phe Lys His Lys Ala Phe Asn
            100                 105                 110

Glu Leu Ala Glu Leu Phe Ile Ile Asn Asn Asn Lys His Ile Asn Pro
        115                 120                 125

Asp Leu Val Asn Gln Tyr Ile Thr Pro Arg Ser Leu Ala Tyr Trp Phe
130                 135                 140

Met Asp Asp Gly Gly Lys Trp Asp Tyr Asn Thr Asn Ser Asn Asn Lys
145                 150                 155                 160

Ser Ile Val Leu Asn Thr Gln Gly Phe Ser Ile Gln Glu Val Gln Tyr
                165                 170                 175

Leu Ile Asp Gly Leu Asn Ile Lys Phe Asn Leu Asn Cys Ile Met Lys
            180                 185                 190

Phe Asn Lys Asn Lys Pro Ile Ile Phe Ile Pro Ser Asp Asn Tyr Lys
        195                 200                 205

His Tyr Tyr Asp Leu Ile Ile Pro Tyr Ile Ile Pro Glu Met Lys Tyr
210                 215                 220

Lys Leu Pro Thr
225

<210> SEQ ID NO 18
<211> LENGTH: 230
<212> TYPE: PRT
<213> ORGANISM: Pichia canadensis

<400> SEQUENCE: 18

Met Lys Lys Gln Ile Ile Asn Lys Lys Asp Leu Leu Gly Leu Gly Pro
 1               5                  10                  15

Asn Ser Lys Leu Ile Lys Asp Tyr Lys Lys Gln Trp Thr Thr Leu Ser
            20                  25                  30

Lys Ile Gln Glu Glu Thr Leu Ile Gly Asn Ile Leu Gly Asp Val Tyr
        35                  40                  45

Ile Lys Lys Leu Lys Arg Asn Lys His Phe Leu Leu Gln Phe Glu Trp
 50                  55                  60

Lys Asn Lys Ala Tyr Ile Glu His Ile Val Arg Val Phe Asp Glu Tyr
 65                  70                  75                  80

Val Ile Ser Pro Pro Thr Leu Tyr Glu Arg Lys Asn His Leu Gly Asn
                 85                  90                  95

Lys Val Ile Thr Trp Arg Ala Gln Thr Phe Glu His Lys Ala Phe Asp
            100                 105                 110

Lys Leu Gly Tyr Tyr Phe Met Glu Asn His Lys Lys Ile Ile Lys Pro
        115                 120                 125

Asp Leu Val Leu Asn Tyr Ile Thr Glu Arg Ser Leu Ala Tyr Trp Phe
130                 135                 140

Met Asp Asp Gly Gly Lys Trp Asp Tyr Asn Lys Lys Thr Lys Asn Lys
145                 150                 155                 160

Ser Leu Val Leu His Thr Gln Gly Phe Lys Lys Glu Val Glu Ile
                165                 170                 175

Leu Ile Asn Asp Leu Asn Ile Lys Phe Asn Leu Asn Cys Ser Ile Lys
            180                 185                 190

Phe Asn Lys Asn Lys Pro Ile Ile Tyr Ile Pro Asn Lys Asp Tyr Glu
        195                 200                 205

Leu Phe Tyr Asn Leu Val Asn Pro Tyr Ile Ile Pro Glu Met Lys Tyr
    210                 215                 220

Lys Leu Leu Phe Asn Val
225             230

<210> SEQ ID NO 19
<211> LENGTH: 34
<212> TYPE: PRT
<213> ORGANISM: Artificial Sequence
<220> FEATURE:
<223> OTHER INFORMATION: TALL Repeat 34

<400> SEQUENCE: 19

Leu Thr Pro Glu Gln Val Val Ala Ile Ala Ser Asn Gly Gly Gly Lys
1               5                   10                  15

Gln Ala Leu Glu Thr Val Gln Arg Leu Leu Pro Val Leu Cys Gln Ala
            20                  25                  30

His Gly

<210> SEQ ID NO 20
<211> LENGTH: 35
<212> TYPE: PRT
<213> ORGANISM: Artificial Sequence
<220> FEATURE:
<223> OTHER INFORMATION: Tall repeat 35

<400> SEQUENCE: 20

Leu Thr Pro Glu Gln Val Val Ala Ile Ala Ser Asn Gly Gly Gly Lys
1               5                   10                  15

Gln Ala Leu Glu Thr Val Gln Arg Leu Leu Pro Val Leu Cys Gln Ala
            20                  25                  30

Pro His Asp
        35

<210> SEQ ID NO 21
<211> LENGTH: 693
<212> TYPE: DNA
<213> ORGANISM: Artificial Sequence
<220> FEATURE:
<223> OTHER INFORMATION: N terminal shortened I-SceI

<400> SEQUENCE: 21
atgggacagg tgatgaacct gggccctaac tctaagctgc ttaaggaata caagtctcag     60
ctgattgagc tgaacattga gcagttcgag gctggcatag cctgattct gggcgatgct    120 tacattaggt ctaggatga gggcaagacc tactgcatgc agttcgagtg gaagaacaag    180
gcttacatgg atcacgtgtg cctgctgtac gatcagtggg tgctgtctcc tcctcacaag    240
aaggagaggg tgaaccactt gggaaacctg gtgattacct ggggcgctca aaccttcaag    300
caccaggctt tcaacaagct ggctaacctg ttcattgtga acaacaagaa gaccattcct    360
aacaacctgg tggagaacta cctgaccect atgtctctgg cttactggtt catggatgat    420
ggcggcaagt gggattacaa caagaactct accaacaagt ctattgtgct gaacacccag    480
tctttcacct tcgaggaggt ggaatacctg gtgaagggcc tgaggaacaa gttccagctg    540
aactgctacg tgaagattaa caagaacaag cctattattt acattgattc tatgtcttac    600 ctgatttttct acaacctgat taagccttac ctgattcctc agatgatgta caagctgcct    660
aacaccatct cttctgagac cttcctgaag tga                             693

<210> SEQ ID NO 22
<211> LENGTH: 666
<212> TYPE: DNA
<213> ORGANISM: Artificial Sequence
<220> FEATURE:
<223> OTHER INFORMATION: N- and C- terminal shortened I-SceI

<400> SEQUENCE: 22

```
atgggacagg tgatgaacct gggccctaac tctaagctgc ttaaggaata caagtctcag      60
ctgattgagc tgaacattga gcagttcgag gctggcatag gcctgattct gggcgatgct     120
tacattaggt ctagggatga gggcaagacc tactgcatgc agttcgagtg gaagaacaag     180
gcttacatgg atcacgtgtg cctgctgtac gatcagtggg tgctgtctcc tcctcacaag     240
aaggagaggg tgaaccactt gggaaacctg gtgattacct ggggcgctca aaccttcaag     300
caccaggctt tcaacaagct ggctaacctg ttcattgtga acaacaagaa gaccattcct     360
aacaacctgg tggagaacta cctgacccct atgtctctgg cttactggtt catggatgat     420
ggcggcaagt gggattacaa caagaactct accaacaagt ctattgtgct gaacacccag     480
tctttcacct cgaggaggt ggaatacctg gtgaagggcc tgaggaacaa gttccagctg     540
aactgctacg tgaagattaa caagaacaag cctattattt acattgattc tatgtcttac     600
ctgattttct acaacctgat taagccttac ctgattcctc agatgatgta caagctgcct     660
aactga                                                                666
```

<210> SEQ ID NO 23
<211> LENGTH: 8411
<212> TYPE: DNA
<213> ORGANISM: Artificial Sequence
<220> FEATURE:
<223> OTHER INFORMATION: Plasmid sequence

<400> SEQUENCE: 23

```
ttcttttgtt tatggttgtc tgtcagcatt tgacttgcag tttcatgctc atagtcatat      60
acgttattct aggcttttt gaatatctta ttactttttt cgtaatacaa ttttataatt     120
ttatcaaagt tatacaacta taactaaaat tagggttttc tacaaaacaa aaaaatcttc     180
taattttttt tgttgtagcc agtttactcg taagttacaa aaaaatacaa atgaacccac     240
atgtattatg cgtttaacta ggattaccat gtactttcat gtactcaatt caccctatac     300
tcttttttt tttttttcta gttccaccca atctataaaa ttctgtccat ttgaccaaat     360
tcaattaatt tctgtaattg cgatttaaaa ttaatattac atgttcacta tttctcgatt     420
tgagggaacc cgagttaaa tatgataaaa atgttaccc atcactacaa atatgttata     480
gtttatactt aatagtggtg ttttggga taattgatga attaagtaaa catgattctt     540
cttatgaagt tgattgagtg attattgtat gtaaacctat gtgattgatg ttattggttg     600
attgagtgat tattgtatta gtatgtaagc aaagatgatt gttcttatga ggtaatttgt     660
tactcattca tccttttgca tatgagaaat tgtgttagcg tacgcaaaac aatagagaac     720
ataaaagata tgtgtattta tttaaggtga cttttgttaa tgatattgta gtatctatac     780
atttatatat aacttgttga atttgagtat aagctatcag gatccggggg atcctctaga     840
gtcgaggtac ccaactttc tatacaaagt tgatagcttg gcgtaatcga tagcttggcg     900
taatcatggt catagctgtt tcctactaga tctgattgtc gttcccgcc ttcagtttaa     960
actatcagtg tttgacagga tatattggcg ggtaaaccta agagaaaaga gcgttatta    1020
```

```
gaataatcgg atatttaaaa gggcgtgaaa aggtttatcc gttcgtccat ttgtatgtcc    1080
atggaacgca gtggcggttt tcatggcttg ttatgactgt tttttggg  tacagtctat    1140 gcctcgggca tccaagcagc aagcgcgtta cgccgtgggt cgatgtttga tgttatggag   1200
cagcaacgat gttacgcagc agggcagtcg ccctaaaaca aagttaaaca tcatggggga   1260
agcggtgatc gccgaagtat cgactcaact atcagaggta gttggcgtca tcgagcgcca   1320
tctcgaaccg acgttgctgg ccgtacattt gtacggctcc gcagtggatg gcggcctgaa   1380
gccacacagt gatattgatt tgctggttac ggtgaccgta aggcttgatg aaacaacgcg   1440
gcgagctttg atcaacgacc ttttggaaac ttcggcttcc cctggagaga gcgagattct   1500
ccgcgctgta gaagtcacca ttgttgtgca cgacgacatc attccgtggc gttatccagc   1560
taagcgcgaa ctgcaatttg gagaatggca gcgcaatgac attcttgcag gtatcttcga   1620
gccagccacg atcgacattg atctggctat cttgctgaca aaagcaagag aacatagcgt   1680
tgccttggta ggtccagcgg cggaggaact ctttgatccg gttcctgaac aggatctatt   1740
tgaggcgcta aatgaaacct taacgctatg gaactcgccg cccgactggg ctggcgatga   1800
gcgaaatgta gtgcttacgt tgtcccgcat ttggtacagc gcagtaaccg gcaaaatcgc   1860
gccgaaggat gtcgctgccg actgggcaat ggagcgcctg ccggcccagt atcagcccgt   1920
catacttgaa gctagacagg cttatcttgg acaagaagaa gatcgcttgg cctcgcgcgc   1980
agatcagttg gaagaatttg tccactacgt gaaaggcgag atcaccaagg tagtcggcaa   2040
ataatgtcta gctagaaatt cgttcaagcc gacgccgctt cgcggcgcgg cttaactcaa   2100
gcgttagatg cactaagcac ataattgctc acagccaaac tatcaggtca agtctgcttt   2160 tattatttt  aagcgtgcat aataagcct  acacaaattg ggagatatat catgcatgac   2220
caaaatccct aacgtgagt  tttcgttcca ctgagcgtca dccccgtag aaaagatcaa   2280 aggatcttct tgagatcctt ttttttctgcg cgtaatctgc tgcttgcaaa caaaaaaacc   2340
accgctacca gcggtggttt gtttgccgga tcaagagcta ccaactcttt ttccgaaggt   2400
aactggcttc agcagagcgc agataccaaa tactgtcctt ctagtgtagc cgtagttagg   2460
ccaccacttc aagaactctg tagcaccgcc tacatacctc gctctgctaa tcctgttacc   2520
agtggctgct gccagtggcg ataagtcgtg tcttaccggg ttggactcaa gacgatagtt   2580
accggataag gcgcagcggt cgggctgaac ggggggttcg tgcacacagc ccagcttgga   2640
gcgaacgacc tacaccgaac tgagatacct acagcgtgag ctatgagaaa gcgccacgct   2700
tcccgaaggg agaaaggcgg acaggtatcc ggtaagcggc agggtcggaa caggagagcg   2760
cacgagggag cttccagggg gaaacgcctg gtatctttat agtcctgtcg gtttcgcca    2820 cctctgactt gagcgtcgat ttttgtgatg ctcgtcaggg gggcggagcc tatggaaaaa   2880
cgccagcaac gcggcctttt tacggttcct ggccttttgc tggccttttg ctcacatgtt   2940
ctttcctgcg ttatccctg  attctgtgga taaccgtatt accgcctttg agtgagctga   3000
taccgctcgc cgcagccgaa cgaccgagcg cagcgagtca gtgagcgagg aagcggaaga   3060
gcgcctgatg cggtatttt  tccttacgca tctgtgcggt atttcacacc gcatatggtg   3120
cactctcagt acaatctgct ctgatgccgc atagttaagc cagtatacac tccgctatcg   3180
ctacgtgact gggtcatggc tgcgccccga cacccgccaa cacccgctga cgcgccctga   3240
cgggcttgtc tgctcccggc atccgcttac agacaagctg tgaccgtctc cgggagctgc   3300
atgtgtcaga ggttttcacc gtcatcaccg aaacgcgcga ggcagggtgc cttgatgtgg   3360
```

```
gcgccggcgg tcgagtggcg acggcgcggc ttgtccgcgc cctggtagat tgcctggccg   3420
taggccagcc atttttgagc ggccagcggc cgcgataggc cgacgcgaag cggcggggcg   3480
tagggagcgc agcgaccgaa gggtaggcgc tttttgcagc tcttcggctg tgcgctggcc   3540
agacagttat gcacaggcca ggcgggtttt aagagtttta ataagtttta aagagtttta   3600
ggcggaaaaa tcgccttttt tctctttttat atcagtcact tacatgtgtg accggttccc   3660
aatgtacggc tttgggttcc caatgtacgg gttccggttc ccaatgtacg gcttggggtt   3720
cccaatgtac gtgctatcca caggaaagag accttttcga cctttttccc ctgctagggc   3780
aatttgccct agcatctgct ccgtacatta ggaaccggcg gatgcttcgc cctcgatcag   3840
gttgcggtag cgcatgacta ggatcgggcc agcctgcccc gcctcctcct tcaaatcgta   3900
ctccggcagg tcatttgacc cgatcagctt gcgcacggtg aaacagaact tcttgaactc   3960
tccggcgctg ccactgcgtt cgtagatcgt cttgaacaac catctggctt ctgccttgcc   4020
tgcggcgcgg cgtgccaggc ggtagagaaa acggccgatg ccgggatcga tcaaaaagta   4080
atcggggtga accgtcagca cgtccgggtt cttgccttct gtgatctcgc ggtacatcca   4140
atcagctagc tcgatctcga tgtactccgg ccgcccggtt cgctctttta cgatcttgta   4200
gcggctaatc aaggcttcac cctcggatac cgtcaccagg cggccgttct tggccttctt   4260
cgtacgctgc atggcaacgt gcgtggtgtt taaccgaatg caggtttcta ccaggtcgtc   4320
tttctgcttt ccgccatcgg ctcgccggca gaacttgagt acgtccgcaa cgtgtggacg   4380
gaacacgcgg ccgggcttgt ctcccttccc ttcccggtat cggttcatgg attcggttag   4440
atgggaaacc gccatcagta ccaggtcgta atcccacaca ctggccatgc cggccggccc   4500
tgcggaaacc tctacgtgcc cgtctggaag ctcgtagcgg atcacctcgc cagctcgtcg   4560
gtcacgcttc gacagacgga aaacggccac gtccatgatg ctgcgactat cgcgggtgcc   4620
cacgtcatag agcatcggaa cgaaaaaatc tggttgctcg tcgcccttgg gcggcttcct   4680
aatcgacggc gcaccggctg ccggcggttg ccgggattct ttgcggattc gatcagcggc   4740
cgcttgccac gattcaccgg ggcgtgcttc tgcctcgatg cgttgccgct gggcggcctg   4800
cgcggccttc aacttctcca ccaggtcatc acccagcgcc gcgccgattt gtaccgggcc   4860
ggatggtttg cgaccgctca cgccgattcc tcgggcttgg gggtccagt gccattgcag   4920 ggccggcaga caacccagcc gcttacgcct ggccaaccgc ccgttcctcc acacatgggg   4980
cattccacgg cgtcggtgcc tggttgttct tgattttcca tgccgcctcc tttagccgct   5040
aaaattcatc tactcattta ttcatttgct catttactct ggtagctgcg cgatgtattc   5100
agatagcagc tcggtaatgg tcttgccttg gcgtaccgcg tacatcttca gcttggtgtg   5160
atcctccgcc ggcaactgaa agttgacccg cttcatggct ggcgtgtctg ccaggctggc   5220
caacgttgca gccttgctgc tgcgtgcgct cggacggccg gcacttagcg tgtttgtgct   5280
tttgctcatt ttctctttac ctcattaact caaatgagtt ttgatttaat ttcagcggcc   5340
agcgcctgga cctcgcgggc agcgtcgccc tcgggttctg attcaagaac ggttgtgccg   5400
gcggcggcag tgcctgggta gctcacgcgc tgcgtgatac gggactcaag aatgggcagc   5460
tcgtacccgg ccagcgcctc ggcaacctca ccgccgatgc gcgtgccttt gatcgcccgc   5520
gacacgacaa aggccgcttg tagccttcca tccgtgacct caatgcgctg cttaaccagc   5580
tccaccaggt cggcggtggc ccatatgtcg taagggcttg gctgcaccgg aatcagcacg   5640
aagtcggctg ccttgatcgc ggacacagcc aagtccgccg cctggggcgc tccgtcgatc   5700
actacgaagt cgcgccggcc gatggccttc acgtcgcggt caatcgtcgg gcggtcgatg   5760
```

```
ccgacaacgg ttagcggttg atcttcccgc acggccgccc aatcgcgggc actgccctgg    5820
ggatcggaat cgactaacag aacatcggcc ccggcgagtt gcagggcgcg ggctagatgg    5880
gttgcgatgg tcgtcttgcc tgacccgcct ttctggttaa gtacagcgat aaccttcatg    5940
cgttcccctt gcgtatttgt ttatttactc atcgcatcat atacgcagcg accgcatgac    6000
gcaagctgtt ttactcaaat acacatcacc ttttagacg cggcgctcg gtttcttcag      6060 cggccaagct ggccggccag gccgccagct tggcatcaga caaaccggcc aggatttcat    6120
gcagccgcac ggttgagacg tgcgcgggcg gctcgaacac gtacccggcc gcgatcatct    6180
ccgcctcgat ctcttcggta atgaaaaacg gttcgtcctg gccgtcctgg tgcggtttca    6240
tgcttgttcc tcttggcgtt cattctcggc ggccgccagg gcgtcggcct cggtcaatgc    6300
gtcctcacgg aaggcaccgc gccgcctggc ctcggtgggc gtcacttcct cgctgcgctc    6360
aagtgcgcgg tacagggtcg agcgatgcac gccaagcagt gcagccgcct ctttcacggt    6420
gcggccttcc tggtcgatca gctcgcgggc gtgcgcgatc tgtgccgggg tgagggtagg    6480
gcggggccca aacttcacgc ctcgggcctt ggcggcctcg cgcccgctcc gggtgcggtc    6540
gatgattagg gaacgctcga actcggcaat gccggcgaac acggtcaaca ccatgcggcc    6600
ggccggcgtg gtggtaacgc gtggtgattt tgtgccgagc tgccggtcgg ggagctgttg    6660
gctggctggt ggcaggatat attgtggtgt aaacaaattg acgcttagac aacttaataa    6720
cacattgcgg acgtctttaa tgtactgaat taacatccgt ttgatacttg tctaaaattg    6780
gctgatttcg agtgcatcta tgcataaaaa caatctaatg acaattatta ccaagcagag    6840
cttgacagga ggcccgatct agtaacatag atgacaccgc gcgcgataat ttatcctagt    6900
ttgcgcgcta tattttgttt tctatcgcgt attaaatgta taattgcggg actctaatca    6960
taaaaaccca tctcataaat aacgtcatgc attacatgtt aattattaca tgcttaacgt    7020
aattcaacag aaattatatg ataatcatcg caagaccggc aacaggattc aatcttaaga    7080
aactttattg ccaaatgttt gaacgatcgg ggatcatccg ggtctgtggc gggaactcca    7140
cgaaaatatc cgaacgcagc aagatctaga gcttgggtcc cgctcagaag aactcgtcaa    7200
gaaggcgata gaaggcgatg cgctgcgaat cgggagcggc gataccgtaa agcacgagga    7260
agcggtcagc ccattcgccg ccaagctctt cagcaatatc acgggtagcc aacgctatgt    7320
cctgatagcg gtccgccaca cccagccggc cacagtcgat gaatccagaa aagcggccat    7380
tttccaccat gatattcggc aagcaggcat cgccatgggt cacgacgaga tcctcgccgt    7440
cgggcatgcg cgccttgagc ctggcgaaca gttcggctgg cgcgagcccc tgatgctctt    7500
cgtccagatc atcctgatcg acaagaccgg cttccatccg agtacgtgct cgctcgatgc    7560
gatgtttcgc ttggtggtcg aatgggcagg tagccggatc aagcgtatgc agccgccgca    7620
ttgcatcagc catgatggat actttctcgg caggagcaag gtgagatgac aggagatcct    7680
gccccggcac ttcgcccaat agcagccagt cccttcccgc ttcagtgaca acgtcgagca    7740
cagctgcgca aggaacgccc gtcgtggcca gccacgatag ccgcgctgcc tcgtcctgca    7800
gttcattcag ggcaccggac aggtcggtct tgacaaaaag aaccgggcgc ccctgcgctg    7860
acagccggaa cacggcggca tcagagcagc cgattgtctg ttgtgcccag tcatagccga    7920
atagcctctc cacccaagcg gccggagaac ctgcgtgcaa tccatcttgt tcaatcatgc    7980
gaaacgatcc agatccggtg cagattattt ggattgagag tgaatatgag actctaattg    8040
gataccgagg ggaatttatg aacgtcagt ggagcatttt tgacaagaaa tatttgctag    8100
```

| | |
|---|---|
| ctgatagtga ccttaggcga cttttgaacg cgcaataatg gtttctgacg tatgtgctta | 8160 |
| gctcattaaa ctccagaaac ccgcggctga gtggctcctt caacgttgcg gttctgtcag | 8220 |
| ttccaaacgt aaaacggctt gtcccgcgtc atcggcgggg gtcataacgt gactccctta | 8280 |
| attctccgct catgatcaga ttgtcgtttc ccgccttcag tttaaactat cagtgtttga | 8340 |
| caggatcctg agtcgttgta aaacgacggc cagtgaatta ccggccagt gaattatcaa | 8400 |
| ctatgtataa t | 8411 |

<210> SEQ ID NO 24
<211> LENGTH: 10765
<212> TYPE: DNA
<213> ORGANISM: Artificial Sequence
<220> FEATURE:
<223> OTHER INFORMATION: Plasmid sequence

<400> SEQUENCE: 24

| | |
|---|---|
| cgcagtggcg gttttcatgg cttgttatga ctgtttttt ggggtacagt ctatgcctcg | 60 |
| ggcatccaag cagcaagcgc gttacgccgt gggtcgatgt ttgatgttat ggagcagcaa | 120 |
| cgatgttacg cagcagggca gtcgccctaa acaaagtta aacatcatgg gggaagcggt | 180 |
| gatcgccgaa gtatcgactc aactatcaga ggtagttggc gtcatcgagc gccatctcga | 240 |
| accgacgttg ctggccgtac atttgtacgg ctccgcagtg gatggcggcc tgaagccaca | 300 |
| cagtgatatt gatttgctgg ttacggtgac cgtaaggctt gatgaaacaa cgcggcgagc | 360 |
| tttgatcaac gaccttttgg aaacttcggc ttcccctgga gagagcgaga ttctccgcgc | 420 |
| tgtagaagtc accattgttg tgcacgacga catcattccg tggcgttatc cagctaagcg | 480 |
| cgaactgcaa tttggagaat ggcagcgcaa tgacattctt gcaggtatct tcgagccagc | 540 |
| cacgatcgac attgatctgg ctatcttgct gacaaaagca agagaacata gcgttgcctt | 600 |
| ggtaggtcca gcggcggagg aactctttga tccggttcct gaacaggatc tatttgaggc | 660 |
| gctaaatgaa accttaacgc tatggaactc gccgcccgac tgggctggcg atgagcgaaa | 720 |
| tgtagtgctt acgttgtccc gcatttggta cagcgcagta accggcaaaa tcgcgccgaa | 780 |
| ggatgtcgct gccgactggg caatggagcg cctgccggcc cagtatcagc ccgtcatact | 840 |
| tgaagctaga caggcttatc ttggacaaga agaagatcgc ttggcctcgc gcgcagatca | 900 |
| gttggaagaa tttgtccact acgtgaaagg cgagatcacc aaggtagtcg gcaaataatg | 960 |
| tctagctaga aattcgttca agccgacgcc gcttcgcggc gcggcttaac tcaagcgtta | 1020 |
| gatgcactaa gcacataatt gctcacagcc aaactatcag gtcaagtctg cttttattat | 1080 |
| ttttaagcgt gcataataag ccctacacaa attgggagat atatcatgca tgaccaaaat | 1140 |
| cccttaacgt gagttttcgt tccactgagc gtcagacccc gtagaaaaga tcaaaggatc | 1200 |
| ttcttgagat cctttttttc tgcgcgtaat ctgctgcttg caaacaaaaa aaccaccgct | 1260 |
| accagcggtg gtttgtttgc cggatcaaga gctaccaact ctttttccga aggtaactgg | 1320 |
| cttcagcaga gcgcagatac caaatactgt ccttctagtg tagccgtagt taggccacca | 1380 |
| cttcaagaac tctgtagcac cgcctacata cctcgctctg ctaatcctgt taccagtggc | 1440 |
| tgctgccagt ggcgataagt cgtgtcttac cgggttggac tcaagacgat agttaccgga | 1500 |
| taaggcgcag cggtcgggct gaacggggg ttcgtgcaca gcccagct tggagcgaac | 1560 |
| gacctacacc gaactgagat acctacagcg tgagctatga gaaagcgcca cgcttcccga | 1620 |
| agggagaaag gcggacaggt atccggtaag cggcagggtc ggaacaggag agcgcacgag | 1680 |
| ggagcttcca gggggaaacg cctggtatct ttatagtcct gtcgggtttc gccacctctg | 1740 |

```
acttgagcgt cgattttgt gatgctcgtc aggggggcgg agcctatgga aaaacgccag    1800
caacgcggcc ttttacggt tcctggcctt ttgctggcct tttgctcaca tgttctttcc    1860
tgcgttatcc cctgattctg tggataaccg tattaccgcc tttgagtgag ctgataccgc    1920
tcgccgcagc cgaacgaccg agcgcagcga gtcagtgagc gaggaagcgg aagagcgcct    1980
gatgcggtat tttctcctta cgcatctgtg cggtatttca caccgcatat ggtgcactct    2040
cagtacaatc tgctctgatg ccgcatagtt aagccagtat acactccgct atcgctacgt    2100
gactgggtca tggctgcgcc ccgacacccg ccaacacccg ctgacgcgcc ctgacgggct    2160
tgtctgctcc cggcatccgc ttacagacaa gctgtgaccg tctccgggag ctgcatgtgt    2220
cagaggtttt caccgtcatc accgaaacgc gcgaggcagg gtgccttgat gtgggcgccg    2280
gcggtcgagt ggcgacggcg cggcttgtcc gcgccctggt agattgcctg gccgtaggcc    2340
agccattttt gagcggccag cggccgcgat aggccgacgc gaagcggcgg ggcgtaggga    2400
gcgcagcgac cgaagggtag cgcttttttg cagctcttcg gctgtgcgct ggccagacag    2460
ttatgcacag gccaggcggg ttttaagagt tttaataagt tttaagagt tttaggcgga    2520 aaaatcgcct tttttctctt ttatatcagt cacttacatg tgtgaccggt tcccaatgta    2580
cggctttggg ttcccaatgt acgggttccg gttcccaatg tacggctttg ggttcccaat    2640
gtacgtgcta ccacaggaa agagacccttt tcgacctttt tcccctgcta gggcaatttg    2700
ccctagcatc tgctccgtac attaggaacc ggcggatgct tcgccctcga tcaggttgcg    2760
gtagcgcatg actaggatcg ggccagcctg ccccgcctcc tccttcaaat cgtactccgg    2820
caggtcattt gacccgatca gcttgcgcac ggtgaaacag aacttcttga actctccggc    2880
gctgccactg cgttcgtaga tcgtcttgaa caaccatctg gcttctgcct tgcctgcggc    2940
gcggcgtgcc aggcggtaga aaaacggcc gatgccggga tcgatcaaaa agtaatcggg    3000
gtgaaccgtc agcacgtccg ggttcttgcc ttctgtgatc tcgcggtaca tccaatcagc    3060
tagctcgatc tcgatgtact ccggccgccc ggtttcgctc tttacgatct tgtagcggct    3120
aatcaaggct tcaccctcgg ataccgtcac caggcggccg ttcttggcct tcttcgtacg    3180
ctgcatggca acgtgcgtgg tgtttaaccg aatgcaggtt tctaccaggt cgtctttctg    3240
ctttccgcca tcggctcgcc ggcagaactt gagtacgtcc gcaacgtgtg gacggaacac    3300
gcggccgggc ttgtctccct tcccttcccg gtatcggttc atggattcgg ttagatggga    3360
aaccgccatc agtaccaggt cgtaatccca cacactggcc atgccggccg ccctgcgga    3420 aacctctacg tgcccgtctg gaagctcgta gcggatcacc tcgccagctc gtcggtcacg    3480
cttcgacaga cggaaaacgg ccacgtccat gatgctgcga ctatcgcggg tgcccacgtc    3540
atagagcatc ggaacgaaaa aatctggttg ctcgtcgccc ttgggcggct tcctaatcga    3600
cggcgcaccg gctgccggcg gttgccggga ttctttgcgg attcgatcag cggccgcttg    3660
ccacgattca ccggggcgtg cttctgcctc gatgcgttgc cgctgggcgg cctgcgcggc    3720
cttcaacttc tccaccaggt catcacccag cgccgcgccg atttgtaccg gccggatgg    3780 tttgcgaccg ctcacgccga ttcctcgggc ttgggggttc cagtgccatt gcagggccgg    3840
cagacaaccc agccgcttac gcctggccaa ccgcccgttc tcccacacat ggggcattcc    3900
acggcgtcgg tgcctggttg ttcttgattt tccatgccgc ctcctttagc cgctaaaatt    3960
catctactca tttattcatt tgctcattta ctctggtagc tgcgcgatgt attcagatag    4020
cagctcggta atggtcttgc cttggcgtac cgcgtacatc ttcagcttgg tgtgatcctc    4080
```

```
cgccggcaac tgaaagttga cccgcttcat ggctggcgtg tctgccaggc tggccaacgt    4140
tgcagccttg ctgctgcgtg cgctcggacg gccggcactt agcgtgtttg tgcttttgct    4200
cattttctct ttacctcatt aactcaaatg agttttgatt taatttcagc ggccagcgcc    4260
tggacctcgc gggcagcgtc gccctcgggt tctgattcaa gaacggttgt gccggcggcg    4320
gcagtgcctg ggtagctcac gcgctgcgtg atacgggact caagaatggg cagctcgtac    4380
ccggccagcg cctcggcaac ctcaccgccg atgcgcgtgc ctttgatcgc ccgcgacacg    4440
acaaaggccg cttgtagcct tccatccgtg acctcaatgc gctgcttaac cagctccacc    4500
aggtcggcgg tggcccatat gtcgtaaggg cttggctgca ccggaatcag cacgaagtcg    4560
gctgccttga tcgcggacac agccaagtcc gccgcctggg gcgctccgtc gatcactacg    4620
aagtcgcgcc ggccgatggc cttcacgtcg cggtcaatcg tcgggcggtc gatgccgaca    4680
acggttagcg gttgatcttc ccgcacgccg gcccaatcgc gggcactgcc ctggggatcg    4740
gaatcgacta acagaacatc ggccccggcg agttgcaggg cgcgggctag atgggttgcg    4800
atggtcgtct tgcctgaccc gccttttctgg ttaagtacag cgataacctt catgcgttcc    4860
ccttgcgtat ttgtttattt actcatcgca tcatatacgc agcgaccgca tgacgcaagc    4920
tgttttactc aaatacacat caccttttta gacggcggcg ctcggtttct tcagcggcca    4980
agctggccgg ccaggccgcc agcttggcat cagacaaacc ggccaggatt tcatgcagcc    5040
gcacggttga gacgtgcgcg ggcggctcga acacgtaccc ggccgcgatc atctccgcct    5100
cgatctcttc ggtaatgaaa aacggttcgt cctggccgtc ctggtgcggt ttcatgcttg    5160
ttcctcttgg cgttcattct cggcggccgc cagggcgtcg gcctcggtca atgcgtcctc    5220
acggaaggca ccgcgccgcc tggcctcggt gggcgtcact tcctcgctgc gctcaagtgc    5280
gcggtacagg gtcgagcgat gcacgccaag cagtgcagcc gcctctttca cggtgcggcc    5340
ttcctggtcg atcagctcgc gggcgtgcgc gatctgtgcc ggggtgaggg tagggcgggg    5400
gccaaacttc acgcctcggg ccttggcggc ctcgcgcccg ctccgggtgc ggtcgatgat    5460
tagggaacgc tcgaactcgg caatgccggc gaacacggtc aacaccatgc ggccggccgg    5520
cgtggtggta acgcgtggtg attttgtgcc gagctgccgg tcggggagct gttggctggc    5580
tggtggcagg atatattgtg gtgtaaacaa attgacgctt agacaactta ataacacatt    5640
gcggacgtct ttaatgtact gaattaacat ccgtttgata cttgtctaaa attggctgat    5700
ttcgagtgca tctatgcata aaaacaatct aatgacaatt attaccaagc aggatcctgt    5760 caaaacactga tagtttaaac tgaaggcggg aaacgacaat ctgatcatga gcggagaatt    5820
aagggagtca cgttatgacc cccgccgatg acgcgggaca agccgtttta cgtttggaac    5880
tgacagaacc gcaacgttga aggagccact cagccgcggg tttctggagt ttaatgagct    5940
aagcacatac gtcagaaacc attattgcgc gttcaaaagt cgcctaaggt cactatcagc    6000
tagcaaatat ttcttgtcaa aaatgctcca ctgacgttcc ataaattccc ctcggtatcc    6060
aattagagtc tcatattcac tctcaatcca ataatctcg acatgtctcc ggagaggaga    6120
ccagttgaga ttaggccagc tacagcagcc gatatggccg cggtttgtga catcgttaac    6180
cattacattg agacgtctac agtgaacttt aggacagagc cacaaacacc acaagagtgg    6240
attgatgacc tagagaggtt gcaagataga taccccttggt tggttgctga ggttgagggt    6300
gttgtggctg gtattgctta cgctgggccc tggaaggcta ggaacgctta cgattggaca    6360
gttgagagta ctgtttacgt gtcacatagg catcaaaggt tgggcctagg atctacattg    6420
tacacacatt tgcttaagtc tatggaggcg caaggtttta agtctgtggt tgctgttata    6480
```

```
ggccttccaa acgatccatc tgttaggttg catgaggctt tgggatacac agcgcggggt    6540
acattgcgcg cggctggata caagcatggt ggatggcatg atgttggttt ttggcaaagg    6600
gattttgagt tgccagctcc tccaaggcca gttaggccag ttacccagat ctgagtcgat    6660
cgaccgatct tgctgcgttc ggatattttc gtggagttcc cgccacagac ccggatgatc    6720
cccgatcgtt caaacatttg gcaataaagt ttcttaagat tgaatcctgt tgccggtctt    6780
gcgatgatta tcatataatt tctgttgaat tacgttaagc atgtaataat taacatgtaa    6840
tgcatgacgt tatttatgag atgggttttt atgattagag tcccgcaatt atacatttaa    6900
tacgcgatag aaaacaaaat atagcgcgca aactaggata aattatcgcg cgcggtgtca    6960
tctatgttac tagatcgggc ctcctgtcaa gctggctgag tcgttgtaaa acgacggcca    7020
gtgaattcga gctcggtacc gagtcaaaga ttcaaataga ggacctaaca gaactcgccg    7080
taaagactgg cgaacagttc atacagagtc tcttacgact caatgacaag aagaaaatct    7140
tcgtcaacat ggtggagcac gacacgcttg tctactccaa aaatatcaaa gatacagtct    7200
cagaagacca aggggcaatt gagacttttc aacaaagggt aatatccgga aacctcctcg    7260
gattccattg cccagctatc tgtcacttta ttgtgaagat agtggaaaag gaaggtggct    7320
cctacaaatg ccatcattgc gataaaggaa aggccatcgt tgaagatgcc tctgccgaca    7380
gtggtcccaa agatggaccc ccacccacga ggagcatcgt ggaaaaagaa gacgttccaa    7440
ccacgtcttc aaagcaagtg gattgatgtg atatctccac tgacgtaagg gatgacgcac    7500
aatcccacta tccttcgcaa gacccttcct ctatataagg aagttcattt catttggaga    7560
ggacagggta cgtacctaga atacaaagaa gaggaagaag aaacctctac agaagaaagt    7620
gatggatccc cgggatcatc tacttctgaa gactcagact cagactaagc aggtgacgaa    7680
cgtcaccaat cccaattcga tctacatccg tcctgtagaa accccaaccc gtgaaatcaa    7740
aaaactcgac ggcctgtggg cattcagtct ggatcgcgaa aactgtggaa ttgatcagcg    7800
ttggtgggaa agcgcgttac aagaaagccg ggcaattgct gtgccaggca gttttaacga    7860
tcagttcgcc gatgcagata ttcgtaatta tgcgggcaac gtctggtatc agcgcgaagt    7920
ctttataccg aaaggttggg caggccagcg tatcgtgctg cgtttcgatg cggtcactca    7980
ttacggcaaa gtgtgggtca ataatcagga agtgatggag catcagggcg gctatacgcc    8040
atttgaagcc gatgtcacgc cgtatgttat tgccggaaaa agtgtacgta tcaccgtttg    8100
tgtgaacaac gaactgaact ggcagactat cccgccggga atggtgatta ccgacgaaaa    8160
cggcaagaaa aagcagtctt acttccatga tttctttaac tatgccggaa tccatcgcag    8220
cgtaatgctc tacaccacgc cgaacacctg gtggacgat atcaccgtgg tgacgcatgt    8280
cgcgcaagac tgtaaccacg cgtctgttga ctggcaggtg gtgccagcgg ccgcctaggg    8340
ataacagggt aatagtctag tccgaaaacg ccgtgagaca tattggttac gatcctaagg    8400
tagcgaaatt cacccggtaa ctctgtgcca gctagagtcc tgtagaaacc caacccgtg    8460 aaatcaaaaa actcgacggc ctgtgggcat tcagtctgga ccgcgaaaac tgtggaattg    8520
atcagcgttg gtgggaaagc gcgttacaag aaagccgggc aattgctgtg ccaggcagtt    8580
ttaacgatca gttcgccgat gcagatattc gtaattatgc gggcaacgtc tggtatcagc    8640
gcgaagtctt tataccgaaa ggttgggcag gccagcgtat cgtgctgcgt ttcgatgcgg    8700
tcactcatta cggcaaagtg tgggtcaata atcaggaagt gatggagcat cagggcggct    8760
atacgccatt tgaagccgat gtcacgccgt atgttattgc cgggaaaagt gtacgtatca    8820
```

```
ccgtttgtgt gaacaacgaa ctgaactggc agactatccc gccgggaatg gtgattaccg    8880
acgaaaacgg caagaaaaag cagtcttact tccatgattt ctttaactat gccggaatcc    8940
atcgcagcgt aatgctctac accacgccga acacctgggt ggacgatatc accgtggtga    9000
cgcatgtcgc gcaagactgt aaccacgcgt ctgttgactg gcaggtggtg gccaatggtg    9060
atgtcagcgt tgaactgcgt gatgcggatc aacaggtggt tgcaactgga caaggcacta    9120
gcgggacttt gcaagtggtg aatccgcacc tctggcaacc gggtgaaggt tatctctatg    9180
aactgtgcgt cacagccaaa gccagacag agtgtgatat ctacccgctt cgcgtcggca    9240
tccggtcagt ggcagtgaag ggcgaacagt tcctgattaa ccacaaaccg ttctacttta    9300
ctggctttgg tcgtcatgaa gatgcggact tgcgtggcaa aggattcgat aacgtgctga    9360
tggtgcacga ccacgcatta atggactgga ttggggccaa ctcctaccgt acctcgcatt    9420
acccttacgc tgaagagatg ctcgactggg cagatgaaca tggcatcgtg gtgattgatg    9480
aaactgctgc tgtcggcttt aacctctctt taggcattgg tttcgaagcg ggcaacaagc    9540
cgaaagaact gtacagcgaa gaggcagtca acggggaaac tcagcaagcg cacttacagg    9600
cgattaaaga gctgatagcg cgtgacaaaa accacccaag cgtggtgatg tggagtattg    9660
ccaacgaacc ggatacccgt ccgcaaggtg cacgggaata tttcgcgcca ctggcggaag    9720
caacgcgtaa actcgacccg acgcgtccga tcacctgcgt caatgtaatg ttctgcgacg    9780
ctcacaccga taccatcagc gatctctttg atgtgctgtg cctgaaccgt tattacggat    9840
ggtatgtcca aagcggcgat ttggaagcgg cagagaaggt actggaaaaa gaacttctgg    9900
cctggcagga gaaactgcat cagccgatta tcatcaccga atacggcgtg gatacgttag    9960
ccgggctgca ctcaatgtac accgacatgt ggagtgaaga gtatcagtgt gcatggctgg    10020
atatgtatca ccgcgtcttt gatcgcgtca gcgccgtcgt cggtgaacag gtatggaatt    10080
tcgccgattt tgcgacctcg caaggcatat tgcgcgttgg cggtaacaag aaagggatct    10140
tcactcgcga ccgcaaaccg aagtcggcgg ctttctgct gcaaaaacgc tggactggca    10200
tgaacttcgg tgaaaaaccg cagcagggag gcaaacaatg aatcaacaac tctcctggcg    10260
caccatcgtc ggctacagcc tcgggaattg ctaccgagct cgaatttccc cgatcgttca    10320
aacatttggc aataaagttt cttaagattg aatcctgttg ccggacttgc gatgattatc    10380
atataatttc tgttgaatta cgttaagcat gtaataatta acatgtaatg catgacgtta    10440
tttatgagat gggtttttat gattagagtc ccgcaattat acatttaata cgcgatagaa    10500
aacaaaatat agcgcgcaaa ctaggataaa ttatcgcgcg cggtgtcatc tatgttacta    10560
gatcggaata agcttggcgt aatcatggtc atagctgttt cctactagat ctgattgtcg    10620
tttcccgcct tcagtttaaa ctatcagtgt ttgacaggat atattggcgg gtaaacctaa    10680
gagaaaagag cgtttattag aataatcgga tatttaaaag ggcgtgaaaa ggtttatccg    10740
ttcgtccatt tgtatgtcca tggaa                                         10765
```

<210> SEQ ID NO 25
<211> LENGTH: 15
<212> TYPE: PRT
<213> ORGANISM: Artificial Sequence
<220> FEATURE:
<223> OTHER INFORMATION: sequence motif of I-SceI

<400> SEQUENCE: 25

His Val Cys Leu Leu Tyr Asp Gln Trp Val Leu Ser Pro Pro His
1               5                   10                  15

-continued

<210> SEQ ID NO 26
<211> LENGTH: 11
<212> TYPE: PRT
<213> ORGANISM: Artificial Sequence
<220> FEATURE:
<223> OTHER INFORMATION: sequence motif of I-SceI

<400> SEQUENCE: 26

Leu Ala Tyr Trp Phe Met Asp Asp Gly Gly Lys
1               5                   10

<210> SEQ ID NO 27
<211> LENGTH: 27
<212> TYPE: PRT
<213> ORGANISM: Artificial Sequence
<220> FEATURE:
<223> OTHER INFORMATION: sequence motif of I-SceI

<400> SEQUENCE: 27

Lys Thr Ile Pro Asn Asn Leu Val Glu Asn Tyr Leu Thr Pro Met Ser
1               5                   10                  15

Leu Ala Tyr Trp Phe Met Asp Asp Gly Gly Lys
            20                  25

<210> SEQ ID NO 28
<211> LENGTH: 19
<212> TYPE: PRT
<213> ORGANISM: Artificial Sequence
<220> FEATURE:
<223> OTHER INFORMATION: sequence motif of I-SceI

<400> SEQUENCE: 28

Lys Pro Ile Ile Tyr Ile Asp Ser Met Ser Tyr Leu Ile Phe Tyr Asn
1               5                   10                  15

Leu Ile Lys

<210> SEQ ID NO 29
<211> LENGTH: 13
<212> TYPE: PRT
<213> ORGANISM: Artificial Sequence
<220> FEATURE:
<223> OTHER INFORMATION: sequence motif of I-SceI

<400> SEQUENCE: 29

Lys Leu Pro Asn Thr Ile Ser Ser Glu Thr Phe Leu Lys
1               5                   10

<210> SEQ ID NO 30
<211> LENGTH: 238
<212> TYPE: PRT
<213> ORGANISM: Artificial Sequence
<220> FEATURE:
<223> OTHER INFORMATION: I-SceI having a 5 amino acid deletion at
      C-terminus

<400> SEQUENCE: 30

Met Gly Pro Lys Lys Lys Arg Lys Val Lys Asn Ile Lys Lys Asn Gln
1               5                   10                  15

Val Met Asn Leu Gly Pro Asn Ser Lys Leu Leu Lys Glu Tyr Lys Ser
            20                  25                  30

Gln Leu Ile Glu Leu Asn Ile Glu Gln Phe Glu Ala Gly Ile Gly Leu
        35                  40                  45

Ile Leu Gly Asp Ala Tyr Ile Arg Ser Arg Asp Glu Gly Lys Thr Tyr
    50                  55                  60

```
Cys Met Gln Phe Glu Trp Lys Asn Lys Ala Tyr Met Asp His Val Cys
 65                  70                  75                  80

Leu Leu Tyr Asp Gln Trp Val Leu Ser Pro Pro His Lys Lys Glu Arg
                 85                  90                  95

Val Asn His Leu Gly Asn Leu Val Ile Thr Trp Gly Ala Gln Thr Phe
            100                 105                 110

Lys His Gln Ala Phe Asn Lys Leu Ala Asn Leu Phe Ile Val Asn Asn
            115                 120                 125

Lys Lys Thr Ile Pro Asn Asn Leu Val Glu Asn Tyr Leu Thr Pro Met
        130                 135                 140

Ser Leu Ala Tyr Trp Phe Met Asp Asp Gly Gly Lys Trp Asp Tyr Asn
145                 150                 155                 160

Lys Asn Ser Thr Asn Lys Ser Ile Val Leu Asn Thr Gln Ser Phe Thr
                165                 170                 175

Phe Glu Glu Val Glu Tyr Leu Val Lys Gly Leu Arg Asn Lys Phe Gln
            180                 185                 190

Leu Asn Cys Tyr Val Lys Ile Asn Lys Asn Lys Pro Ile Ile Tyr Ile
            195                 200                 205

Asp Ser Met Ser Tyr Leu Ile Phe Tyr Asn Leu Ile Lys Pro Tyr Leu
        210                 215                 220

Ile Pro Gln Met Met Tyr Lys Leu Pro Asn Thr Ile Ser Ser
225                 230                 235

<210> SEQ ID NO 31
<211> LENGTH: 9
<212> TYPE: PRT
<213> ORGANISM: Saccharomyces cerevisiae

<400> SEQUENCE: 31

Thr Ile Ser Ser Glu Thr Phe Leu Lys
1               5

<210> SEQ ID NO 32
<211> LENGTH: 9
<212> TYPE: PRT
<213> ORGANISM: Artificial Sequence
<220> FEATURE:
<223> OTHER INFORMATION: endonuclease motif

<400> SEQUENCE: 32

Leu Ala Gly Leu Ile Asp Ala Asp Gly
1               5

<210> SEQ ID NO 33
<211> LENGTH: 15
<212> TYPE: PRT
<213> ORGANISM: Artificial Sequence
<220> FEATURE:
<223> OTHER INFORMATION: Consensus Sequence
<220> FEATURE:
<221> NAME/KEY: misc_feature
<222> LOCATION: (4)..(4)
<223> OTHER INFORMATION: Xaa can be any amino acid
<220> FEATURE:
<221> NAME/KEY: misc_feature
<222> LOCATION: (6)..(7)
<223> OTHER INFORMATION: Xaa can be any amino acid
<220> FEATURE:
<221> NAME/KEY: misc_feature
<222> LOCATION: (9)..(11)
<223> OTHER INFORMATION: Xaa can be any amino acid

<400> SEQUENCE: 33
```

```
Ala Gln Arg Xaa Leu Xaa Xaa Ser Xaa Xaa Xaa Gln Arg Val Leu
1               5                   10                  15

<210> SEQ ID NO 34
<211> LENGTH: 8
<212> TYPE: PRT
<213> ORGANISM: Saccharomyces cerevisiae

<400> SEQUENCE: 34

Thr Ile Ser Ser Glu Thr Phe Leu
1               5

<210> SEQ ID NO 35
<211> LENGTH: 7
<212> TYPE: PRT
<213> ORGANISM: Saccharomyces cerevisiae

<400> SEQUENCE: 35

Thr Ile Ser Ser Glu Thr Phe
1               5

<210> SEQ ID NO 36
<211> LENGTH: 6
<212> TYPE: PRT
<213> ORGANISM: Saccharomyces cerevisiae

<400> SEQUENCE: 36

Thr Ile Ser Ser Glu Thr
1               5

<210> SEQ ID NO 37
<211> LENGTH: 5
<212> TYPE: PRT
<213> ORGANISM: Saccharomyces cerevisiae

<400> SEQUENCE: 37

Thr Ile Ser Ser Glu
1               5

<210> SEQ ID NO 38
<211> LENGTH: 4
<212> TYPE: PRT
<213> ORGANISM: Saccharomyces cerevisiae

<400> SEQUENCE: 38

Thr Ile Ser Ser
1

<210> SEQ ID NO 39
<211> LENGTH: 9
<212> TYPE: PRT
<213> ORGANISM: Artificial Sequence
<220> FEATURE:
<223> OTHER INFORMATION: mutated amino acid sequence from I-SceI
      nuclease

<400> SEQUENCE: 39

Thr Ile Lys Ser Glu Thr Phe Leu Lys
1               5

<210> SEQ ID NO 40
<211> LENGTH: 9
<212> TYPE: PRT
<213> ORGANISM: Artificial Sequence
<220> FEATURE:
```

```
<223> OTHER INFORMATION: mutated amino acid sequence from I-SceI
      nuclease

<400> SEQUENCE: 40

Ala Ile Ala Asn Gln Ala Phe Leu Lys
1               5

<210> SEQ ID NO 41
<211> LENGTH: 8
<212> TYPE: PRT
<213> ORGANISM: Artificial Sequence
<220> FEATURE:
<223> OTHER INFORMATION: Combination of the deletion I-SceI-1 with the
      mutant S229A

<400> SEQUENCE: 41

Thr Ile Ala Ser Glu Thr Phe Leu
1               5

<210> SEQ ID NO 42
<211> LENGTH: 25
<212> TYPE: PRT
<213> ORGANISM: Artificial Sequence
<220> FEATURE:
<223> OTHER INFORMATION: Zinc finger domain component
<220> FEATURE:
<221> NAME/KEY: misc_feature
<222> LOCATION: (2)..(3)
<223> OTHER INFORMATION: Xaa can be any amino acid
<220> FEATURE:
<221> NAME/KEY: misc_feature
<222> LOCATION: (4)..(5)
<223> OTHER INFORMATION: Xaa can be any amino acid or no amino acid
<220> FEATURE:
<221> NAME/KEY: misc_feature
<222> LOCATION: (7)..(18)
<223> OTHER INFORMATION: Xaa can be any amino acid
<220> FEATURE:
<221> NAME/KEY: misc_feature
<222> LOCATION: (20)..(22)
<223> OTHER INFORMATION: Xaa can be any amino acid
<220> FEATURE:
<221> NAME/KEY: misc_feature
<222> LOCATION: (23)..(24)
<223> OTHER INFORMATION: Xaa can be any amino acid or no amino acid

<400> SEQUENCE: 42

Cys Xaa Xaa Xaa Xaa Cys Xaa Xaa Xaa Xaa Xaa Xaa Xaa Xaa Xaa
1               5                   10                  15

Xaa Xaa His Xaa Xaa Xaa Xaa Xaa His
            20                  25

<210> SEQ ID NO 43
<211> LENGTH: 230
<212> TYPE: PRT
<213> ORGANISM: Artificial Sequence
<220> FEATURE:
<223> OTHER INFORMATION: Consensus Sequence
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (28)..(28)
<223> OTHER INFORMATION: Xaa can be any naturally occurring amino acid
<220> FEATURE:
<221> NAME/KEY: misc_feature
<222> LOCATION: (31)..(31)
<223> OTHER INFORMATION: Xaa can be any naturally occurring amino acid
<220> FEATURE:
<221> NAME/KEY: misc_feature
```

```
<222> LOCATION: (34)..(34)
<223> OTHER INFORMATION: Xaa can be any naturally occurring amino acid
<220> FEATURE:
<221> NAME/KEY: misc_feature
<222> LOCATION: (95)..(95)
<223> OTHER INFORMATION: Xaa can be any naturally occurring amino acid
<220> FEATURE:
<221> NAME/KEY: misc_feature
<222> LOCATION: (107)..(107)
<223> OTHER INFORMATION: Xaa can be any naturally occurring amino acid
<220> FEATURE:
<221> NAME/KEY: misc_feature
<222> LOCATION: (114)..(114)
<223> OTHER INFORMATION: Xaa can be any naturally occurring amino acid
<220> FEATURE:
<221> NAME/KEY: misc_feature
<222> LOCATION: (123)..(123)
<223> OTHER INFORMATION: Xaa can be any naturally occurring amino acid
<220> FEATURE:
<221> NAME/KEY: misc_feature
<222> LOCATION: (125)..(125)
<223> OTHER INFORMATION: Xaa can be any naturally occurring amino acid
<220> FEATURE:
<221> NAME/KEY: misc_feature
<222> LOCATION: (156)..(156)
<223> OTHER INFORMATION: Xaa can be any naturally occurring amino acid
<220> FEATURE:
<221> NAME/KEY: misc_feature
<222> LOCATION: (166)..(166)
<223> OTHER INFORMATION: Xaa can be any naturally occurring amino acid
<220> FEATURE:
<221> NAME/KEY: misc_feature
<222> LOCATION: (169)..(169)
<223> OTHER INFORMATION: Xaa can be any naturally occurring amino acid
<220> FEATURE:
<221> NAME/KEY: misc_feature
<222> LOCATION: (177)..(177)
<223> OTHER INFORMATION: Xaa can be any naturally occurring amino acid
<220> FEATURE:
<221> NAME/KEY: misc_feature
<222> LOCATION: (181)..(181)
<223> OTHER INFORMATION: Xaa can be any naturally occurring amino acid
<220> FEATURE:
<221> NAME/KEY: misc_feature
<222> LOCATION: (188)..(188)
<223> OTHER INFORMATION: Xaa can be any naturally occurring amino acid
<220> FEATURE:
<221> NAME/KEY: misc_feature
<222> LOCATION: (203)..(203)
<223> OTHER INFORMATION: Xaa can be any naturally occurring amino acid
<220> FEATURE:
<221> NAME/KEY: misc_feature
<222> LOCATION: (206)..(206)
<223> OTHER INFORMATION: Xaa can be any naturally occurring amino acid
<220> FEATURE:
<221> NAME/KEY: misc_feature
<222> LOCATION: (213)..(213)
<223> OTHER INFORMATION: Xaa can be any naturally occurring amino acid
<220> FEATURE:
<221> NAME/KEY: misc_feature
<222> LOCATION: (226)..(227)
<223> OTHER INFORMATION: Xaa can be any naturally occurring amino acid
<220> FEATURE:
<221> NAME/KEY: misc_feature
<222> LOCATION: (229)..(229)
<223> OTHER INFORMATION: Xaa can be any naturally occurring amino acid

<400> SEQUENCE: 43

Met Lys Xaa Ile Lys Lys Asn Gln Ile Met Asn Leu Gly Pro Asn Ser
1               5                   10                  15

Lys Leu Leu Lys Glu Tyr Lys Ser Gln Leu Thr Xaa Leu Thr Xaa Glu
            20                  25                  30

Gln Xaa Glu Ala Gly Ile Gly Leu Ile Leu Gly Asp Ala Tyr Ile Arg
        35                  40                  45

Ser Arg Asp Glu Gly Lys Thr Tyr Cys Met Gln Phe Glu Trp Lys Asn
```

```
               50                  55                  60
Lys Ala Tyr Ile Asp His Val Cys Leu Leu Tyr Asp Glu Trp Val Leu
 65                  70                  75                  80

Ser Pro Pro His Lys Lys Glu Arg Val Asn His Leu Gly Asn Xaa Val
                 85                  90                  95

Ile Thr Trp Gly Ala Gln Thr Phe Lys His Xaa Ala Phe Asn Lys Leu
            100                 105                 110

Ala Xaa Leu Phe Ile Ile Asn Asn Lys Lys Xaa Ile Xaa Asn Asn Leu
        115                 120                 125

Val Glu Asn Tyr Ile Thr Pro Arg Ser Leu Ala Tyr Trp Phe Met Asp
    130                 135                 140

Asp Gly Gly Lys Trp Asp Tyr Asn Lys Asn Ser Xaa Asn Lys Ser Ile
145                 150                 155                 160

Val Leu Asn Thr Gln Xaa Phe Thr Xaa Glu Glu Val Glu Tyr Leu Ile
                165                 170                 175

Xaa Gly Leu Asn Xaa Lys Phe Asn Leu Asn Cys Xaa Met Lys Phe Asn
            180                 185                 190

Lys Asn Lys Pro Ile Ile Tyr Ile Pro Ser Xaa Ser Tyr Xaa Ile Phe
            195                 200                 205

Tyr Asn Leu Ile Xaa Pro Tyr Ile Ile Pro Glu Met Lys Tyr Lys Leu
        210                 215                 220

Pro Xaa Xaa Ile Xaa Ser
225                 230

<210> SEQ ID NO 44
<211> LENGTH: 18
<212> TYPE: DNA
<213> ORGANISM: Artificial Sequence
<220> FEATURE:
<223> OTHER INFORMATION: DNA recognition site of I-SceI

<400> SEQUENCE: 44
ttaccctgtt atccctag                                                    18

<210> SEQ ID NO 45
<211> LENGTH: 17
<212> TYPE: DNA
<213> ORGANISM: Artificial Sequence
<220> FEATURE:
<223> OTHER INFORMATION: DNA recognition site of I-SceI

<400> SEQUENCE: 45
tagggataac agggtaa                                                     17
```